United States Patent
Zeiner et al.

(10) Patent No.: US 12,251,106 B1
(45) Date of Patent: Mar. 18, 2025

(54) COMPULSORY COMPRESSION RETAINERS FOR STAPLE CARTRIDGES WITH IMPLANTABLE ADJUNCTS

(71) Applicant: CILAG GMBH INTERNATIONAL, Zug (CH)

(72) Inventors: Mark Zeiner, Loveland, OH (US); Sarah Alexandra Scully, Cincinnati, OH (US); Michael Vendely, Lebanon, OH (US); Heather Strang, Cincinnati, OH (US); Christopher Q Seow, Cincinnati, OH (US); Madelaine Franzoni, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/505,802

(22) Filed: Nov. 9, 2023

(51) Int. Cl.
*A61B 17/072* (2006.01)
*A61B 17/00* (2006.01)
*A61B 17/068* (2006.01)

(52) U.S. Cl.
CPC ...... *A61B 17/072* (2013.01); *A61B 17/07207* (2013.01); *A61B 17/07292* (2013.01); *A61B 2017/00477* (2013.01); *A61B 17/068* (2013.01); *A61B 2017/07214* (2013.01); *A61B 2017/07271* (2013.01)

(58) Field of Classification Search
CPC . A61B 17/068; A61B 17/0644; A61B 17/072; A61B 17/07207; A61B 17/07292; A61B 17/115; A61B 2017/00473; A61B 2017/00477; A61B 2017/07214; A61B 2017/07271
USPC ..... 227/19, 176.1, 175.2, 180.1; 606/1, 139, 606/219
See application file for complete search history.

(56) References Cited

U.S. PATENT DOCUMENTS

| | | | |
|---|---|---|---|
| 9,351,730 B2 | 5/2016 | Schmid | |
| 9,629,814 B2* | 4/2017 | Widenhouse | A61K 9/70 |
| 9,724,094 B2* | 8/2017 | Baber | H02H 3/207 |
| 10,117,652 B2* | 11/2018 | Schmid | A61B 17/068 |
| 11,071,545 B2* | 7/2021 | Baber | A61B 17/00 |
| 2006/0025816 A1* | 2/2006 | Shelton, IV | A61B 17/07207 606/215 |
| 2009/0001122 A1* | 1/2009 | Prommersberger | A61B 17/072 227/176.1 |
| 2009/0078739 A1* | 3/2009 | Viola | A61B 17/07292 227/180.1 |
| 2012/0187179 A1* | 7/2012 | Gleiman | A61B 17/072 227/181.1 |
| 2012/0253298 A1* | 10/2012 | Henderson | A61B 17/0644 604/93.01 |
| 2017/0055982 A1* | 3/2017 | Zeiner | A61B 17/0682 |
| 2017/0056016 A1* | 3/2017 | Barton | A61B 17/07292 |

* cited by examiner

Primary Examiner — Scott A Smith
(74) Attorney, Agent, or Firm — TROUTMAN PEPPER LOCKE LLP

(57) ABSTRACT

Retainers and retainer systems for staple cartridges with implantable adjuncts are disclosed. The retainers and retainer systems enable a compressive force to be applied to implantable adjuncts on staple cartridges.

20 Claims, 38 Drawing Sheets

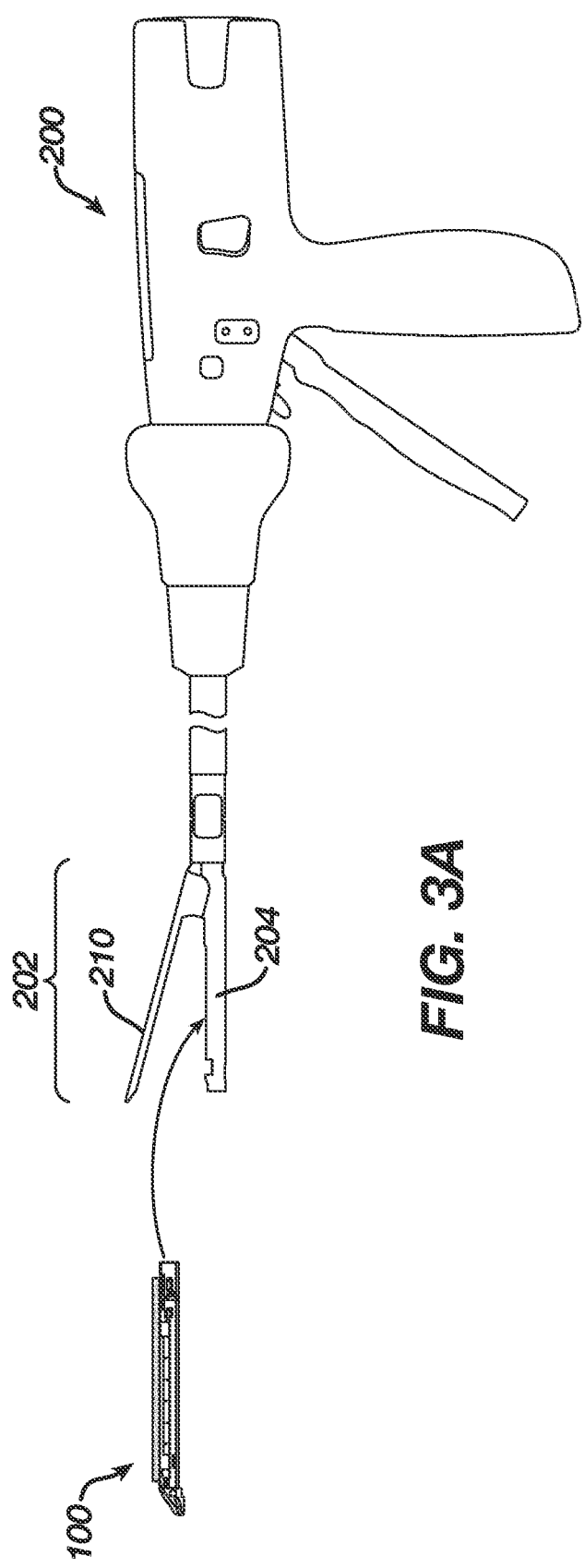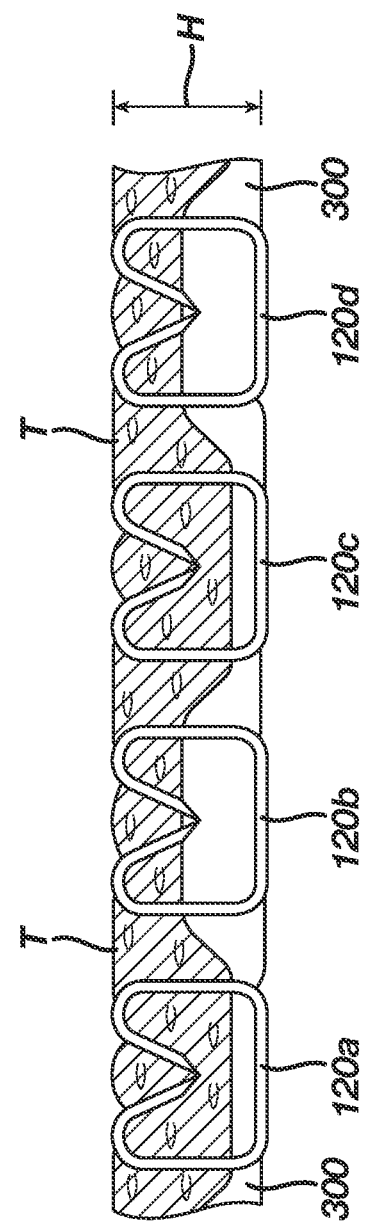
FIG. 3A
FIG. 3B

COMPULSORY COMPRESSION RETAINERS FOR STAPLE CARTRIDGES WITH IMPLANTABLE ADJUNCTS

FIELD OF INVENTION

The present disclosure generally relates to retainers and retainer systems for staple cartridges with implantable adjuncts. More specifically, the present disclosure relates to retainers and retainer systems that enable a compressive force to be applied to implantable adjuncts on staple cartridges.

BACKGROUND

Stapling is a crucial aspect of many surgical procedures, such as gastrointestinal, thoracic, and gynecological surgeries. Staple cartridges used in said stapling procedures may include an implantable adjunct on the deck of the cartridge. Care must be taken to ensure the implantable adjunct is properly adhered to the deck so that it is not dislodged from the deck during shipment or, importantly, during surgery before the adjunct is positioned at the treatment site.

SUMMARY

It is an object of the present designs to provide devices and methods to meet the above-stated needs. The designs can be for systems and devices for protecting an implantable adjunct on a staple cartridge, while also providing structure to allow compression of the adjunct to the deck of the staple cartridge before being used in surgery.

The disclosed technology includes a staple cartridge comprising an elongate body. The elongate body comprises a deck and defines a plurality of staple pockets which are each accessible via an opening defined by the deck. The staple cartridge further includes an implantable adjunct removably secured to the deck and a retainer.

The retainer is removably securable to the elongate body and is moveable through a range of motion from a first position to a second position relative to the elongate body while the retainer is secured to the elongate body.

With the retainer secured to the elongate body, the implantable adjunct is positioned intermediate the retainer and the elongate body. Furthermore, a movement of the retainer through at least a portion of the range of motion compresses the implantable adjunct against the deck of the elongate body.

The staple cartridge further includes a latch that is configured to secure the retainer to the elongate body when the retainer is in the first position and to automatically release the retainer from securement via the latch to the elongate body when the retainer is in the second position.

The disclosed technology further includes a method of causing a retainer to compress an implantable adjunct against a deck of an elongated body. The method includes actuating a retainer through a range of motion from a first position to a second position relative the elongate body while the retainer is secured to the elongate body. The method includes compressing the implantable adjunct against the deck when actuating the retainer from the first position to the second position, releasing the retainer from the elongate body, and inserting the elongate body into a channel of an end effector.

Other aspects of the present disclosure will become apparent upon reviewing the following detailed description in conjunction with the accompanying figures. Additional features or manufacturing and use steps can be included as would be appreciated and understood by a person of ordinary skill in the art.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation. It is expected that those of skill in the art can conceive of and combine elements from multiple figures to better suit the needs of the user.

FIG. 3A is a side-view schematic of a staple cartridge being loaded into a surgical instrument, according to aspects of the present disclosure.

FIG. 3B is a schematic view of an implantable adjunct stapled to tissue, according to aspects of the present disclosure.

DETAILED DESCRIPTION

Figure 1:
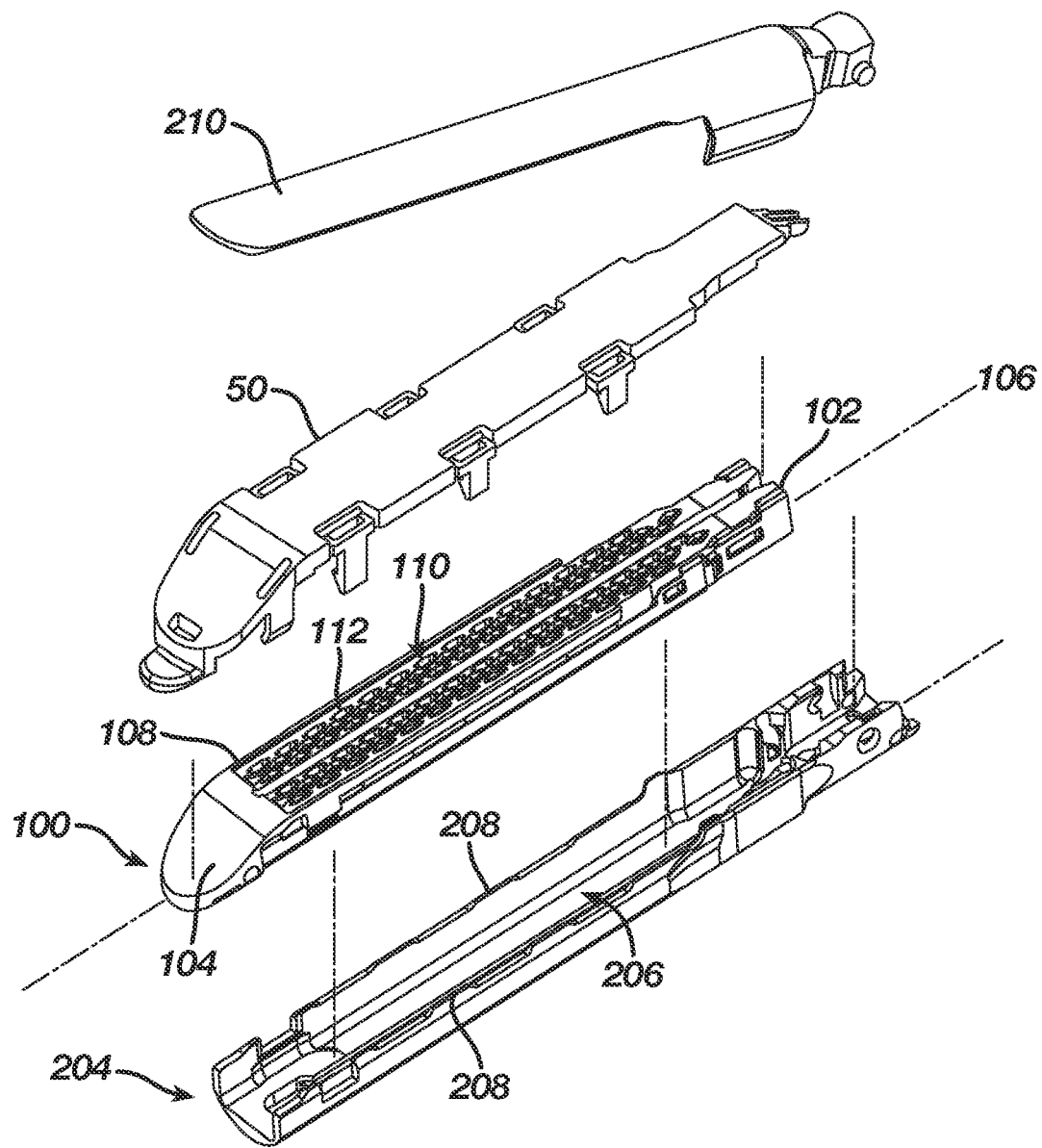
FIG. 1 is a perspective view of a replaceable staple cartridge without an adjunct.

Specific examples of the present invention are now described in detail with reference to the Figures, where identical reference numbers indicate elements which are functionally similar or identical. The examples provide solutions for staple cartridge systems that include an implantable adjunct. An implantable adjunct can be used in stapling surgery to account for differing tissue thicknesses across the length of the stapling surface. For instance, a length of tissue clamped in an end effector of a surgical instrument may be thicker at one end of the staple cartridge than at the other end. However, the staple cartridge may be loaded with staples of a single length, meaning the staples may be properly sized for the thicker section of tissue, but may be too long for the thinner section of tissue. If the staples are too long, proper compression of the tissue at the staple site may not be optimal. An implantable adjunct can account for this differing tissue thickness by providing support for the thinner sections of tissue. Where the tissue is thick, the implantable adjunct can be compressed all the way down since no additional thickness is needed to account for the staple length. Where the tissue is thin, the implantable adjunct is not as compressed, meaning the adjunct provides the additional thickness needed to account for the staple length, thereby providing proper compression in that section of the tissue.

The implantable adjunct must be properly, yet reversibly, adhered to the deck of the staple cartridge so that it does not become dislodged during shipment or, importantly, during the surgical procedure. For instance, during surgery the staple cartridge is loaded into an end effector of a cutter/stapler surgical instrument, sent through a cannula to a surgical site, traversed through and around tissue, and then positioned at the target tissue site that will be cut and stapled by the surgical instrument. If the implantable adjunct is not properly adhered to the deck of the staple cartridge, it may become dislodged from the deck during this procedure. The adjunct is adhered to the cartridge deck with an attachment material, which needs to be sticky or tacky enough to keep the adjunct adhered to the deck, but not so sticky that it is difficult to detach from the deck after the stapling procedure is completed. As such, the present retainer systems provide solutions that ensure the adjunct is properly adhered to the staple cartridge right before the staple cartridge is positioned at the treatment site. These systems provide such solutions by incorporating retainers and retainer systems that enable a temporary compressive force to be applied to implantable adjuncts on staple cartridges before they are used in surgery.

The invention is not necessarily limited to the examples described, which can be varied in construction and detail. The terms "distal" and "proximal" are used throughout this description and are meant to refer to positions and directions relative to the handle of surgical instrument 200. As such, "distal" or "distally" refer to a position distant to or a direction away from the handle of surgical instrument 200 (i.e., a direction toward a patient). Similarly, "proximal" or "proximally" refer to a position near or a direction towards the handle of surgical instrument 200 (i.e., toward an operator of the handle). Furthermore, the singular forms "a," "an," and "the" include plural referents unless the context clearly dictates otherwise. Furthermore, the use of "couple", "coupled", or similar phrases should not be construed as being limited to a certain number of components or a particular order of components unless the context clearly dictates otherwise.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g., "about 90%" may refer to the range of values from 71% to 109%.

The components described herein can be formed from biocompatible materials using manufacturing methods known to those of skill in the art. For example, and not limitation, the components described herein can be molded from a thermoplastic.

FIG. 1 provides background on how the presently described retainer systems improve upon prior designs because the presently-disclosed systems take into account an adjunct being positioned on the staple cartridge. Referring now to the figure, FIG. 1 shows an exploded view of a prior staple cartridge 100 that does not include an implantable adjunct on deck 108 thereof. In these prior examples, retainer 50 can be attached to staple cartridge 100 from proximal end 102 to distal end 104 to ensure that staples within various staple pockets 110 do not fall out of openings 112 within deck 108. Retainer 50, therefore, is merely a static device with a function of preventing staples from falling out before staple cartridge 100 is positioned within channel 206 of first jaw frame 204 of end effector 202. Retainer 50 is simply removed when staple cartridge 100 is inserted between channel rails 208 of channel 206.

Figure 2A:
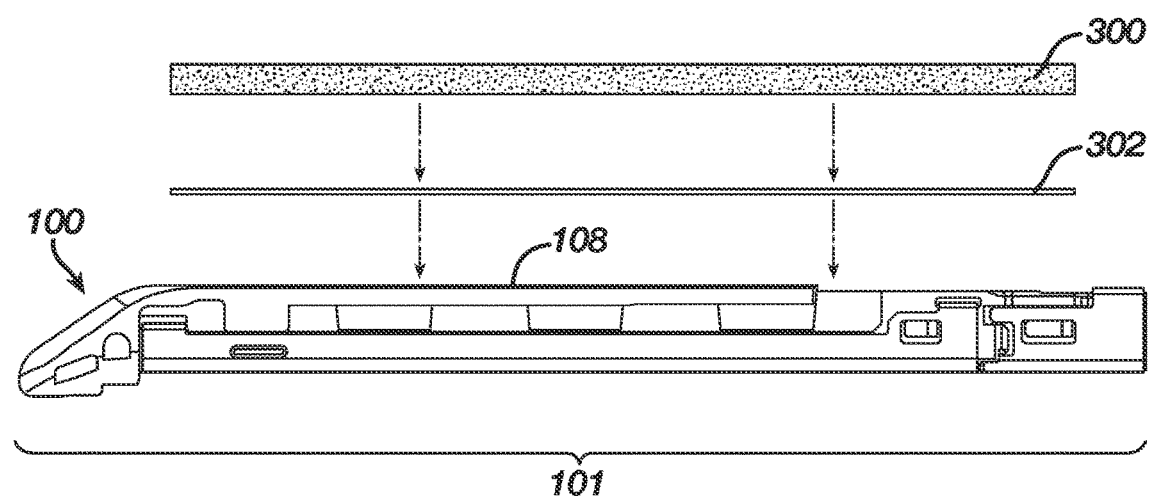
FIG. 2A is a schematic view showing a replaceable staple cartridge, an attachment material, and an implantable adjunct, according to aspects of the present disclosure.
Figure 2B:
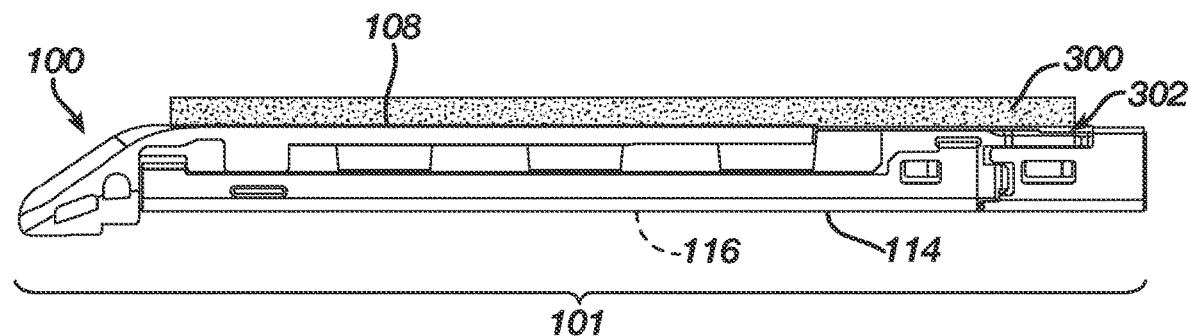
FIG. 2B is a schematic view showing the replaceable staple cartridge, attachment material, and implantable adjunct of FIG. 2A assembled, according to aspects of the present disclosure.
Figure 2C:
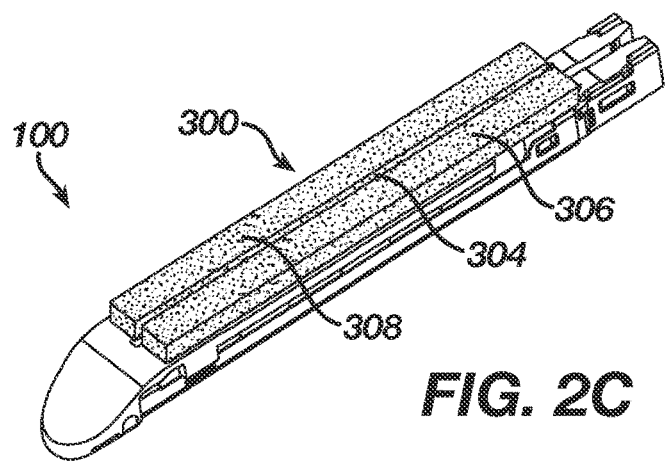
FIG. 2C is a perspective view of the assembled staple cartridge, attachment material, and implantable adjunct shown in FIG. 2B, according to aspects of the present disclosure.

FIGS. 2A-2C illustrate staple cartridges that include an implantable adjunct. As seen in the exploded view of FIG. 2A, the system includes staple cartridge 100 (which is substantially similar to the staple cartridge shown in FIG. 1) and implantable adjunct 300 which is adhered to deck 108 that is positioned along elongate body 101 of staple cartridge 100. Adjunct 300 can be adhered to staple cartridge 100 with attachment material 302. As described above, attachment material 302 can provide sufficient adhesion for adjunct 300 to remain adhered to deck 108 when being positioned at the treatment site, but the adhesion does not impair the ability of adjunct 300 from being detached from deck 108 when being implanted. In some instances, attachment material can be an adhesive, adhesive strip, double-sided tape, and the like. The attachment material 302 can be or include a pressure sensitive adhesive such that applying pressure to the adjunct 300 causes the attachment material 302 to be compressed and increases the adhesion of the attachment material 302 to the cartridge 100 and the adjunct 300. In other words, compression of the adjunct 300 against the cartridge 100 (several different methods are disclosed throughout this disclosure) increases the adhesion of the adjunct 300 to the cartridge 100 via the attachment material 302. The compression of the attachment material 302 can be less than a second and greatly increases the adhesion of the adjunct 300 to the cartridge.

FIG. 2B shows adjunct 300 adhered to deck 108 via attachment material 302. FIG. 2C is a perspective view of adjunct 300 adhered to deck 108. For background, the staples of the systems described herein are fired through adjunct 300 during the stapling procedure. In some instances, adjunct 300 can include sled groove 304 within length 350 of the adjunct. Sled groove 304 provides a path for a knife (not shown in figures) to traverse such that the knife does not need to cut through adjunct 300, thereby preserving the edge on the knife. When adjunct 300 includes sled groove 304, adjunct 300 can be considered to be separated into adjunct first side 306 and adjunct second side 308. In some examples, adjunct 300 can include laminated layers, such as a foam and/or porous material laminated with a mesh material, wherein the sled groove 304 is disposed in the foam and/or porous material but the mesh material remains intact. In other examples, adjunct 300 can include a film layer and/or a mesh layer. The film layer can comprise material commonly used with absorbable monofilament sutures and can be heat processed with a mesh layer to act as a bonding agent to hold the mesh and foam of the adjunct 300 together.

FIG. 3A is a side-view schematic of staple cartridge 100 being loaded into a surgical instrument, i.e., surgical instrument 200. Staple cartridge 100 is loaded into end effector 202 before being positioned at the treatment site. As described above, staple cartridge 100 is inserted into first jaw frame 204. Anvil 210 clamps down toward staple cartridge 100 during the stapling procedure. Once the tissue is stapled, anvil 210 opens to leave the staples and adjunct attached to the tissue. Staple cartridge 100 remains in first jaw frame 204 as surgical instrument 200 is removed from the treatment site. Although FIG. 3A shows staple cartridge 100 without a retainer attached thereto, some example retainers described herein can be configured to be inserted into first jaw frame 204 while attached to the staple cartridge 100.

As stated above, implantable adjunct 300 can account for this differing tissue thickness by providing support for the thinner sections of tissue. Where the tissue is thick, implantable adjunct 300 can be compressed all the way down since no additional thickness is needed to account for the staple length. Where the tissue is thin, the implantable adjunct 300 is not as compressed, meaning the adjunct provides the additional thickness needed to account for the staple length, thereby providing proper compression in that section of the tissue. FIG. 3B is a schematic showing the implantable adjunct 300 stapled to tissue (T) having different thickness. The individual staples 120a,b,c,d have the same height (H), so the implantable adjunct 300 fills in the space for thinner sections of tissue (i.e., the tissue (T) shown at staples 120b and 120d). For thicker sections of tissue (i.e., the tissue (T) shown at staples 120a and 120c), the implantable adjunct 300 is more compressed as the staples do not need the additional space (i.e., height) filled in by the implantable adjunct 300.

The retainers described herein can be configured to be moved through a range of motion from a first position to a second position relative to the elongate body 101. Although various examples of retainers are shown and described herein, it will be appreciated that, when each of the various retainers are moved from the first position to the second position, the retainer can compress the implantable adjunct 300 which in turn compresses the attachment material 302 and secures the implantable adjunct 300 to the deck 108. The various examples described herein can be configured to ensure a user engages the attachment material 302 so that the implantable adjunct 300 is securely attached to the deck 108 to prevent the implantable adjunct 300 from dislodging from the deck 108 during use.

Referring now to FIGS. 4A-4H, the example implementation shows a staple cartridge 100 and retainer system that can protect an adjunct during shipment of the staple cartridge and also provide a compressive force to the implantable adjunct 300. A retainer 400 can be disposed on a side of the implantable adjunct 300 opposite the staple cartridge 100. The retainer 400 can be configured to protect the implantable adjunct and staple cartridge 100 during shipment and handling prior to insertion of the staple cartridge 100 into the channel 206 of the end effector 200. The retainer 200 can be attached to a pan protector 410 and, together, the retainer 400 and the pan protector 410 can be secured around the cartridge 100 to protect the implantable adjunct 300 and the cartridge 100.

As will be described in greater detail herein, the retainer 400 and pan protector 410 can be configured such that a user must move the retainer 400 to compress the implantable adjunct 300 before the retainer 400 can be removed and the staple cartridge 100 can be inserted into the channel 206. To help remove the retainer 400 from the pan protector 410 and the cartridge 100, the retainer 400 can include a retainer lever 404 that can be pushed or pulled by a user to disengage the retainer 400 from the cartridge 100 and the pan protector.

Figure 4A:
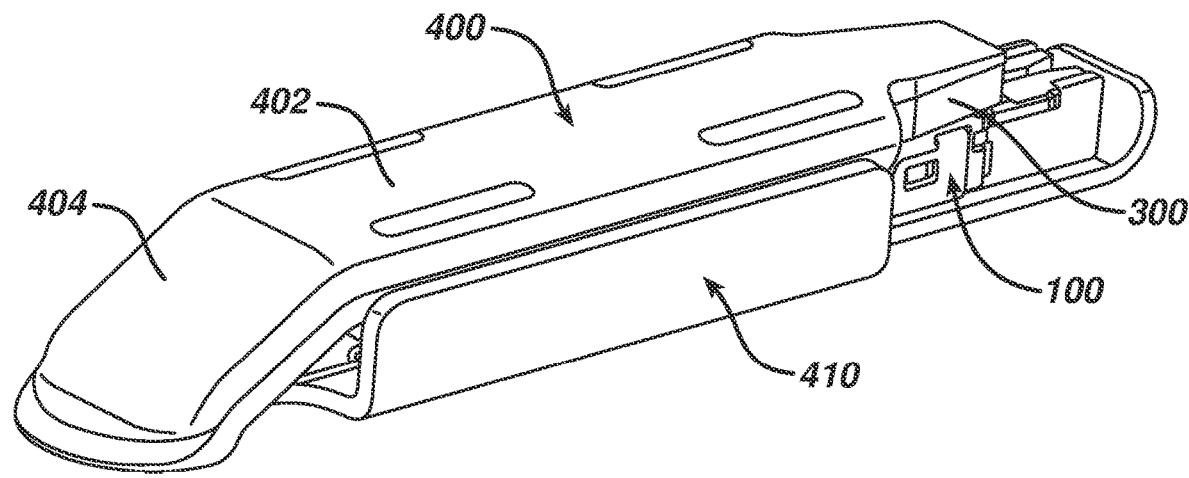
FIG. 4A is a top perspective view of an example staple cartridge retainer and a pan cover, according to aspects of the present disclosure.
Figure 4B:
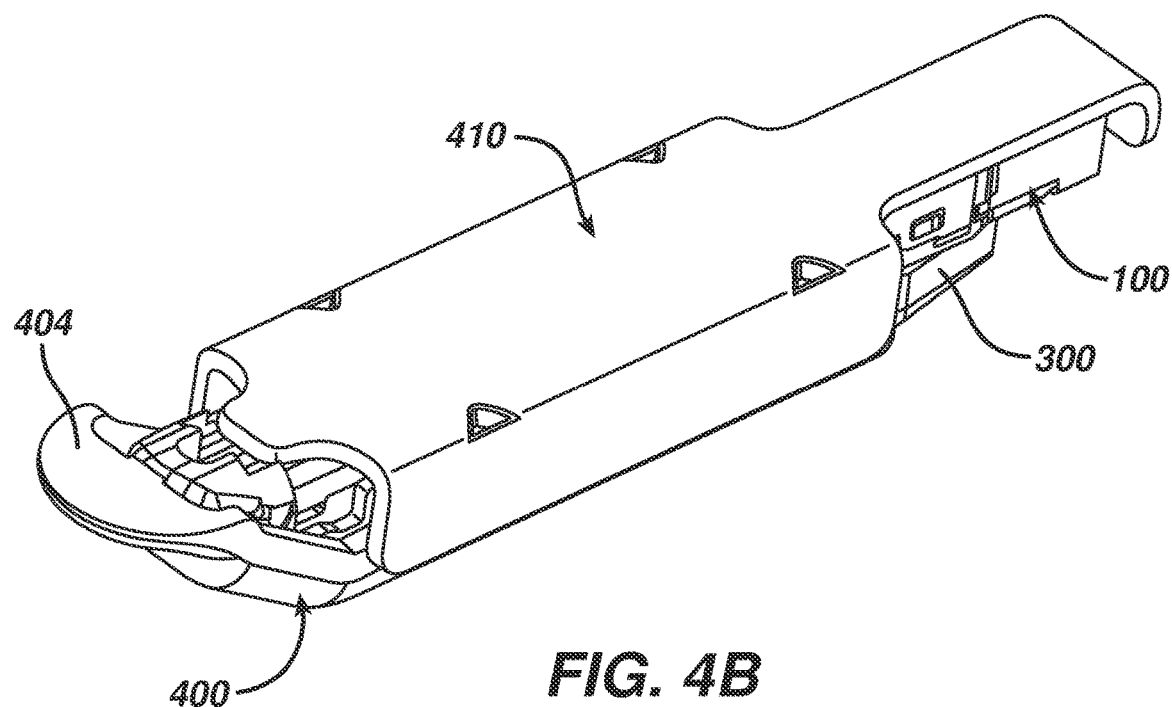
FIG. 4B is a bottom perspective view of the example staple cartridge retainer shown in FIG. 4A, according to aspects of the present disclosure.
Figure 4C:
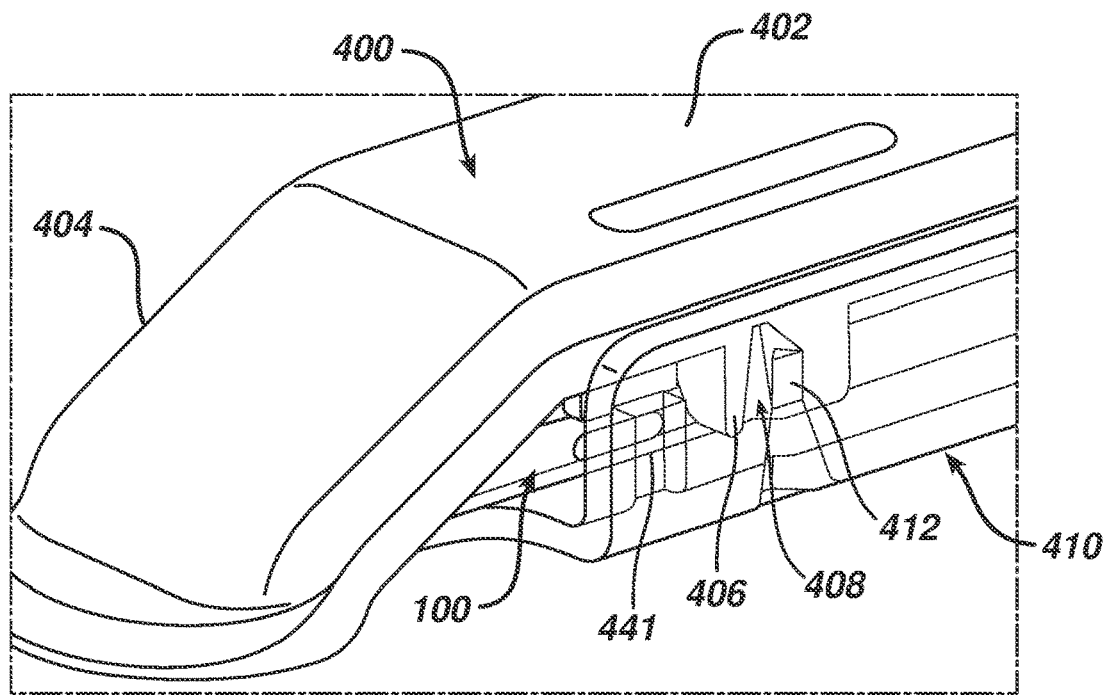
FIG. 4C is a detail view of the example staple cartridge retainer shown in FIG. 4A, according to aspects of the present disclosure.
Figure 4D:
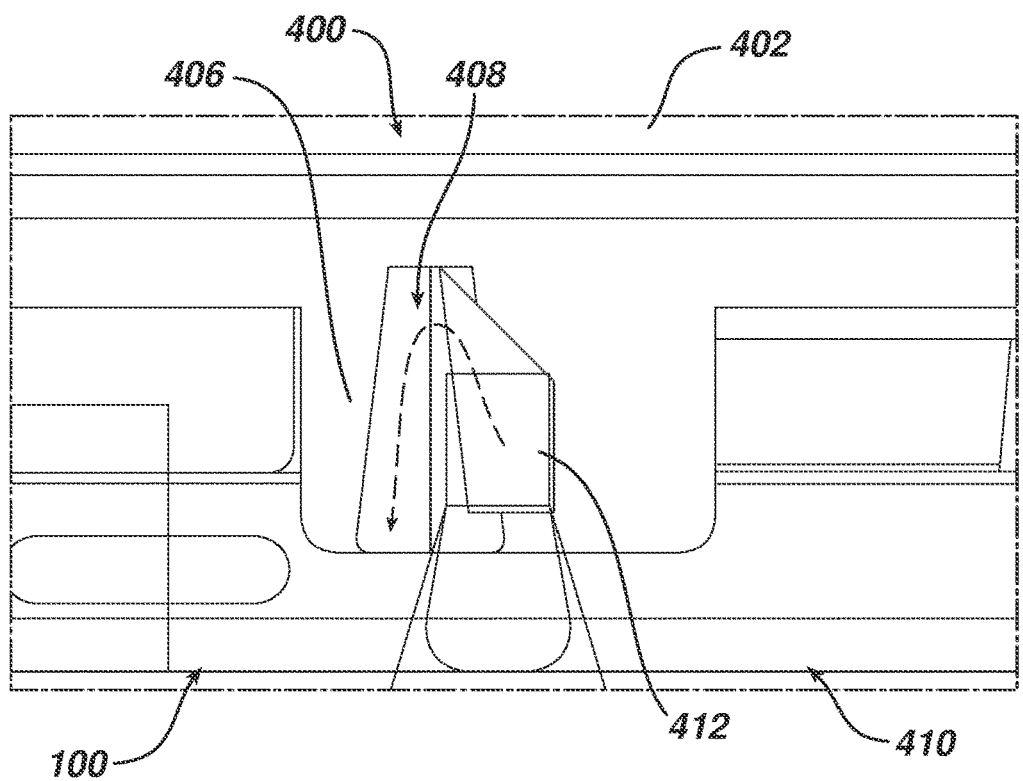
FIG. 4D is a detail view of the example staple cartridge retainer shown in FIG. 4A, according to aspects of the present disclosure.

Turning now to FIGS. 4C and 4D, the retainer can further include a retainer tab 406 that extends outwardly from the retainer body 402 toward the pan protector 410. The retainer tab 406 can define a retainer track 408 that can extend at least partially along the retainer tab 406. The retainer track 408 can be a recess formed into a side of the retainer tab 406. The pan protector 410 can further comprise a pan cover protrusion 412 that can extend inwardly and be configured to engage or otherwise slide along the retainer track 408. In other words, the pan cover protrusion 412 can extend at least partially into the retainer track 408 and the retainer track 408 and the pan cover protrusion 412 can, together, secure the retainer 400 to the pan cover 410.

As shown by the dashed arrow in FIG. 4D, the retainer track 408 can be configured such that the pan cover protrusion 412 is guided along the retainer track 408 from a securing position (as shown in FIGS. 4C and 4D) in which the retainer 400 is secured to the pan cover 410 to a release position in which the retainer 400 can be released from the pan protector 410. The retainer track 408 can include an angled edge that can cause the pan cover protrusion 412 to be moved out of the securing position when the retainer 400 is compressed toward the pan protector 410. In other words, the retainer track 408 and the pan cover protrusion 412 can be configured to keep the retainer 400 attached to the pan cover 410 unless a user compresses (e.g., pinches) the retainer 400 toward the pan cover 410 which will cause compression of the implantable adjunct 300 against the deck 108.

As the user presses on the retainer 400, the retainer 400 moves toward the pan cover 410 and the pan cover protrusion 412 slides along the retainer track 408 until the retainer 400 contacts a pan cover retainer stop 414 which prevents further movement of the retainer 400 toward the pan cover 410. The retainer tab 406 can similarly act as a stop to prevent the retainer 400 from moving closer to the pan cover 410. The pan cover retainer stop 414 and the retainer tab 406 can help to prevent over compression of the implantable adjunct 300 and the cartridge 100.

Figure 4E:
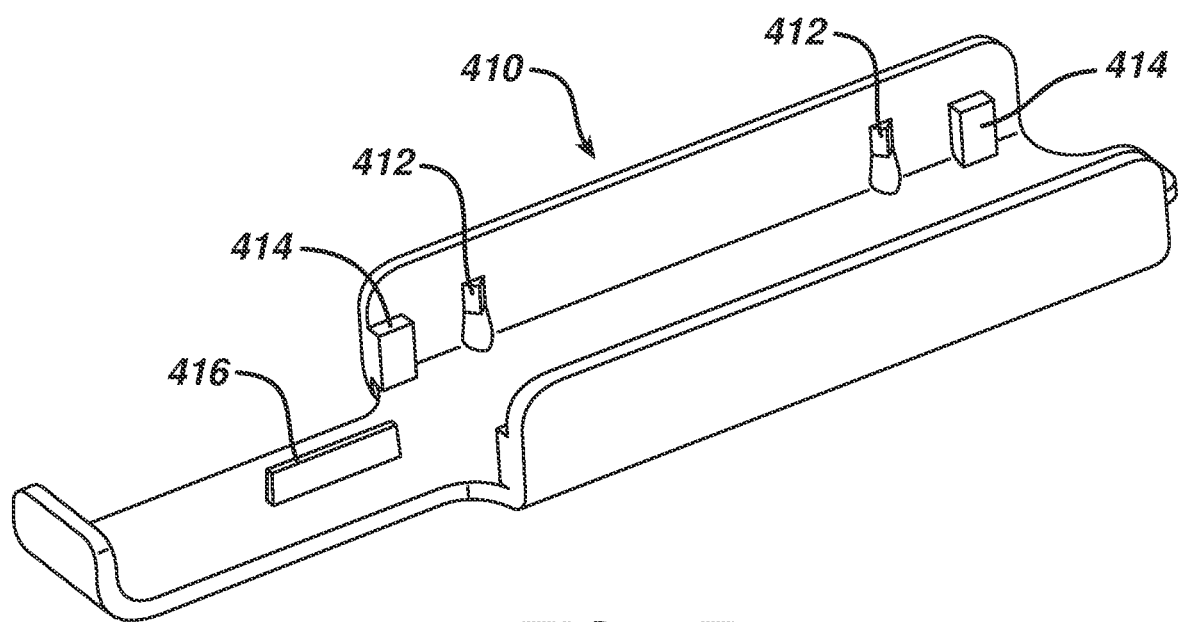
FIG. 4E is a perspective view of the pan cover shown in FIGS. 4A-4D, according to aspects of the present disclosure.
Figure 4F:
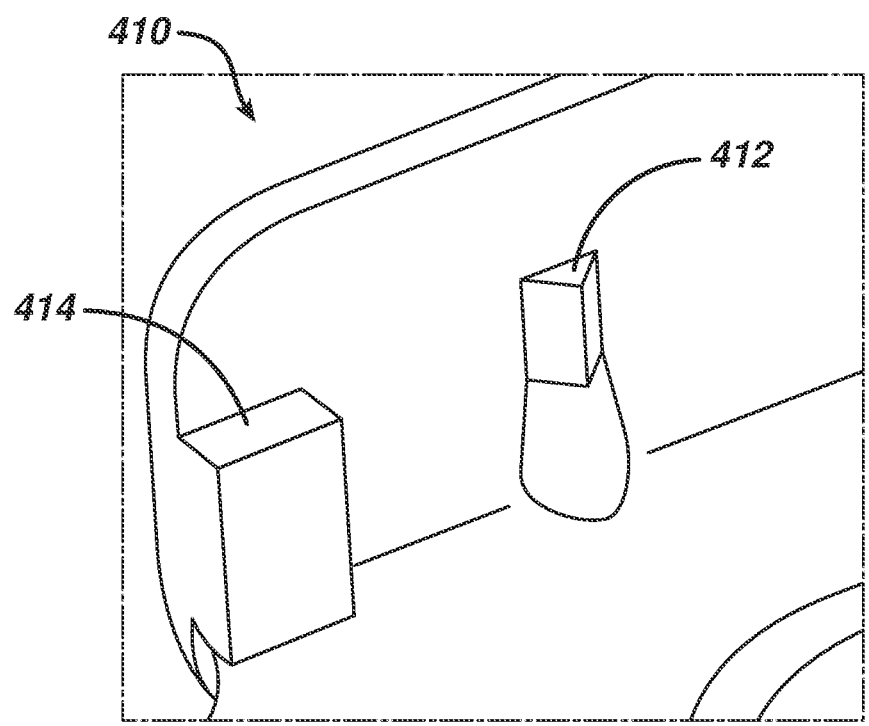
FIG. 4F is a detail view of the pan cover shown in FIGS. 4A-4E, according to aspects of the present disclosure.
Figure 4G:
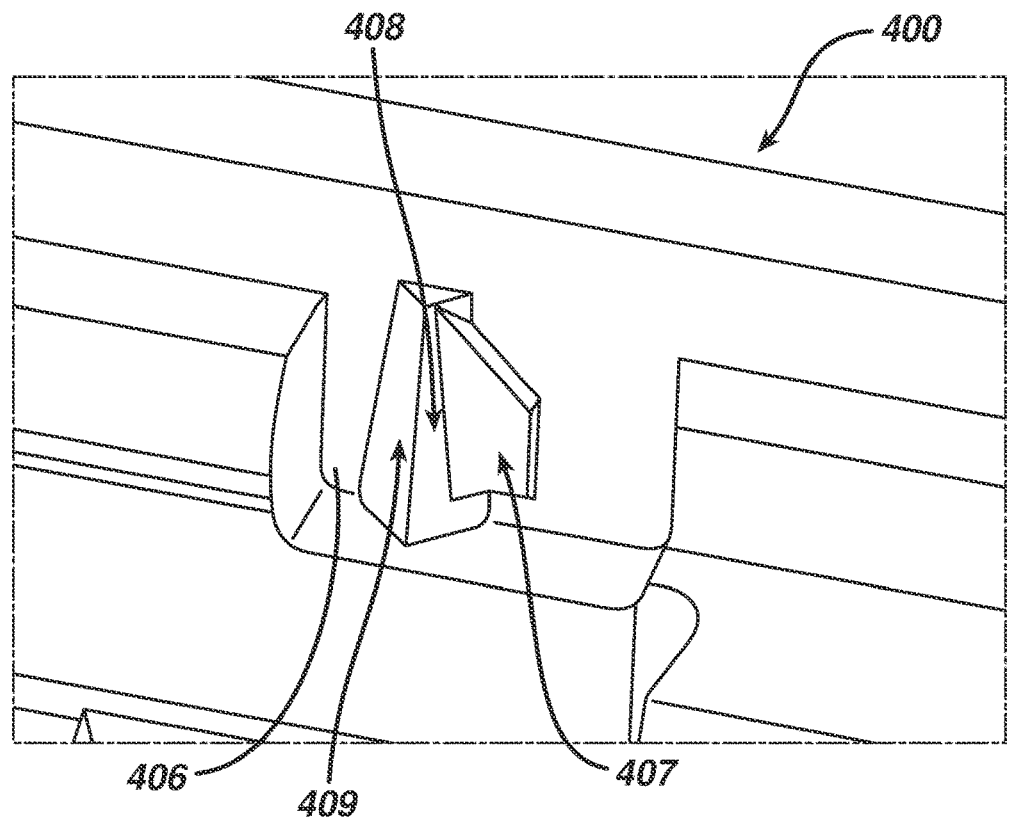
FIG. 4G is a detail view of the retainer shown in FIGS. 4A-4D with a staple cartridge removed, according to aspects of the present disclosure.
Figure 4H:
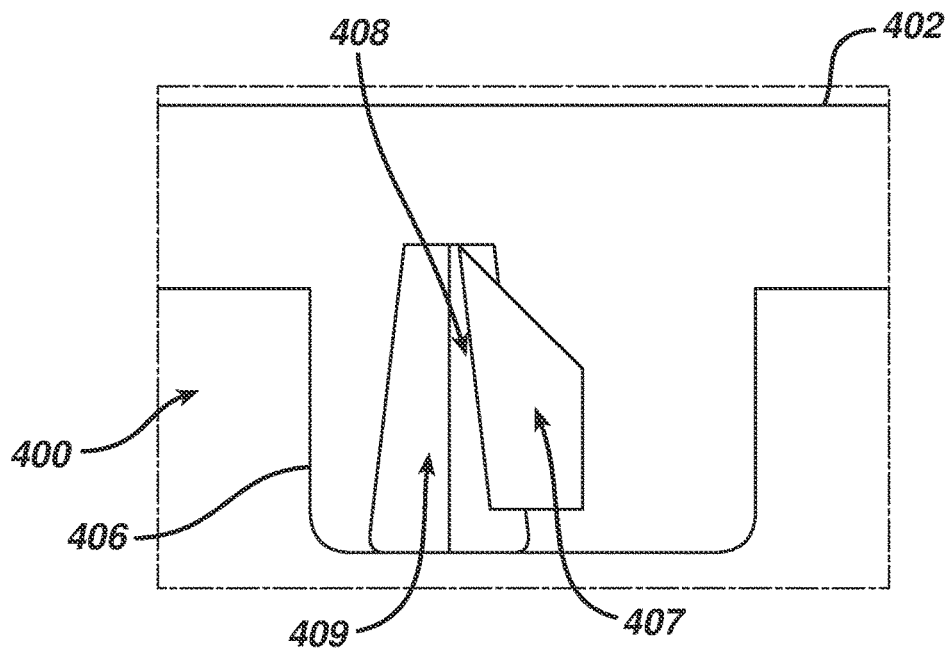
FIG. 4H is another detail view of the retainer shown in FIGS. 4A-4D with a staple cartridge removed, according to aspects of the present disclosure.

As shown in FIGS. 4G and 4H, the retainer track 408 can include a first portion 409 and a second portion 407. The first portion 407 can be configured to keep the pan cover protrusion 412 in place and, consequently, the pan cover 410 attached to the retainer 400 until the retainer 400 is moved toward the pan cover 410. As the retainer 400 is caused to over toward the pan cover 410, the pan cover protrusion 412 will slide along the first portion 407 and be guided by an angled edge toward the second portion 409. The second portion 409 can be slightly recessed compared to the first portion 407 such that the pan cover protrusion 412 will be caused to move into the second portion 409 when the retainer 400 is moved toward the pan cover 410 and prevented from returning back to the first portion 407 when the retainer 400 is moved away from the pan cover 410. The first portion 407, as an example, can include an angled edge that will cause the pan cover protrusion 412 to moved into the second portion 409. Once the pan cover protrusion 412 is moved into the second portion 409, the pan cover protrusion 412 can be kept in the recessed second portion 409 and the retainer 400 can then be removed or otherwise disconnected from the pan cover 400. Once the retainer 400 and pan cover 410 are disconnected, the retainer 400 and pan cover 410 can each be removed from the cartridge 100 and the cartridge can be inserted into the channel 206.

As shown in FIG. 4E, the pan cover 410 can include a pan cover alignment protrusion 416 that can help to align the pan cover with the cartridge 100. The pan cover alignment protrusion 416, for example, can be configured to extend inwardly into a recess, aperture, channel, or other portion of the cartridge 100 to ensure the pan cover 410 is properly aligned with the cartridge.

Although the retainer 400 is shown as being positioned between outer edges of the pan cover 410, it will be appreciated that in other examples the pan cover 410 can be positioned between outer edges of the retainer 400 such that the retainer 400 is wider than the pan cover 410.

Turning now to FIGS. 5A-5J, another example retainer 500 and pan cover 510 are shown. The cartridge 100 and the implantable adjunct 300 can be disposed between the retainer 500 and the pan cover 510 and the retainer 500 and the pan cover 510 can be pushed toward each other to cause the retainer 500 to release from the pan cover 500. Similar to the retainer 400, the retainer 500 can include a retainer body 502 and a retainer lever 504 that can be used to remove the retainer 400 from the cartridge 100.

Figure 5A:
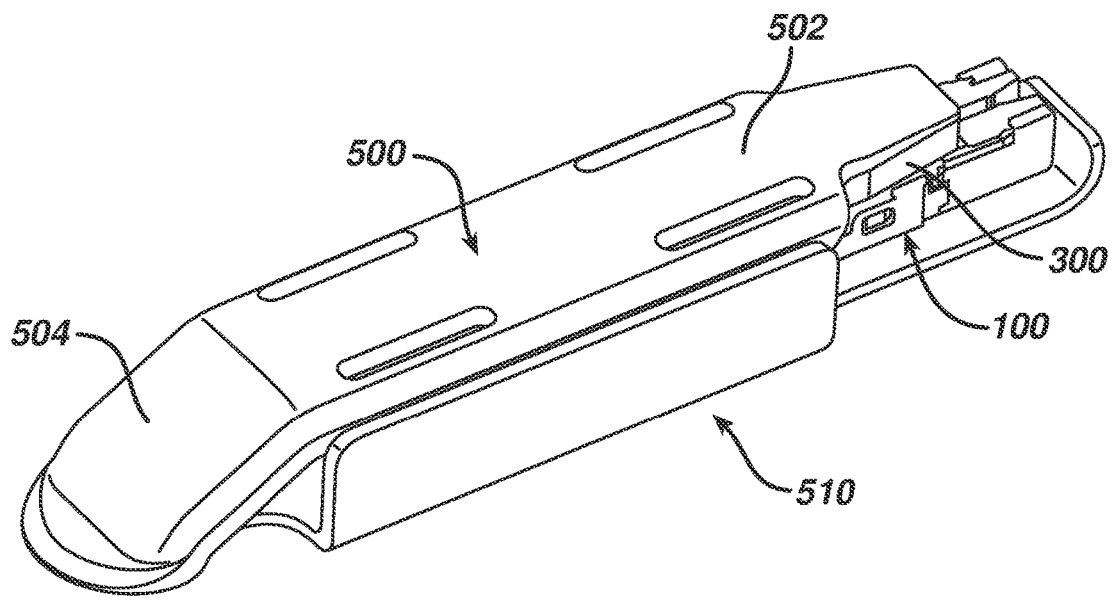
FIG. 5A is a perspective view of another staple cartridge retainer and a pan cover, according to aspects of the present disclosure.
Figure 5B:
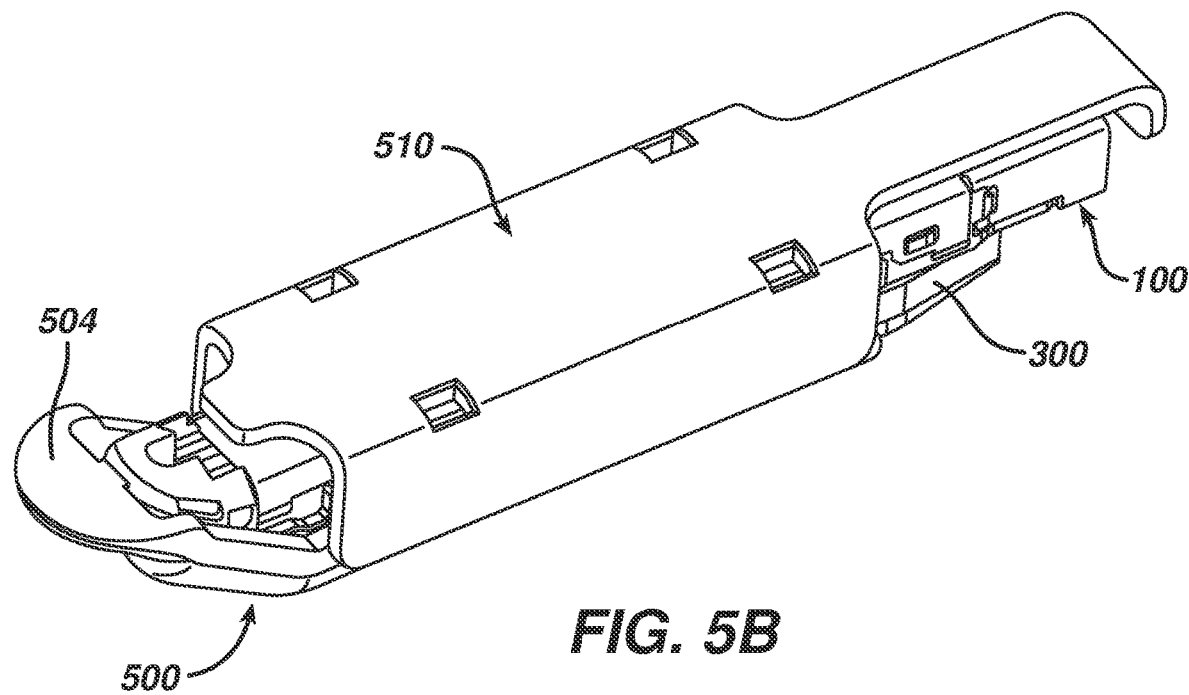
FIG. 5B is a bottom perspective view of the example staple cartridge retainer shown in FIG. 5A, according to aspects of the present disclosure.
Figure 5C:
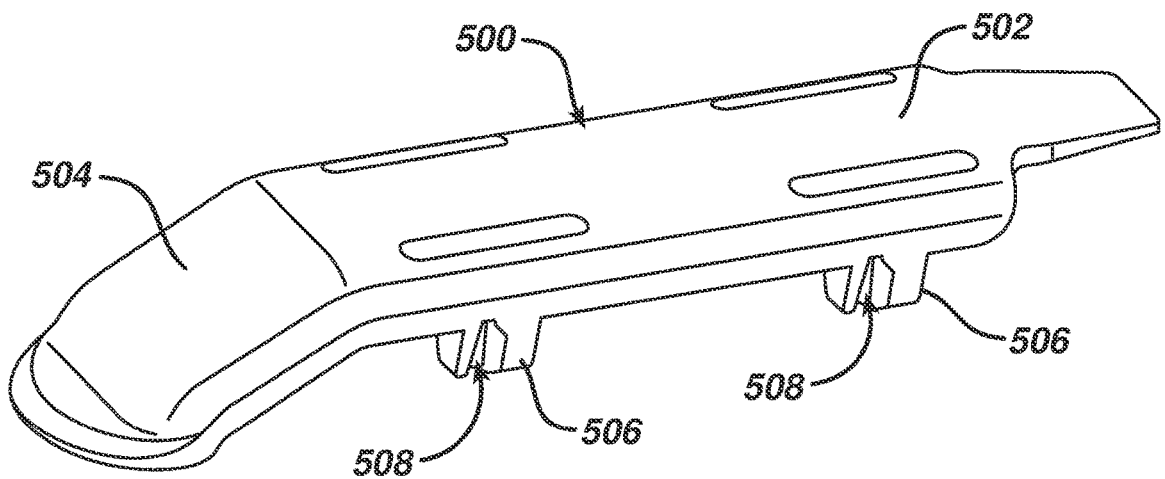
FIG. 5C is a top perspective view of the retainer shown in FIGS. 5A-5B, according to aspects of the present disclosure.
Figure 5D:
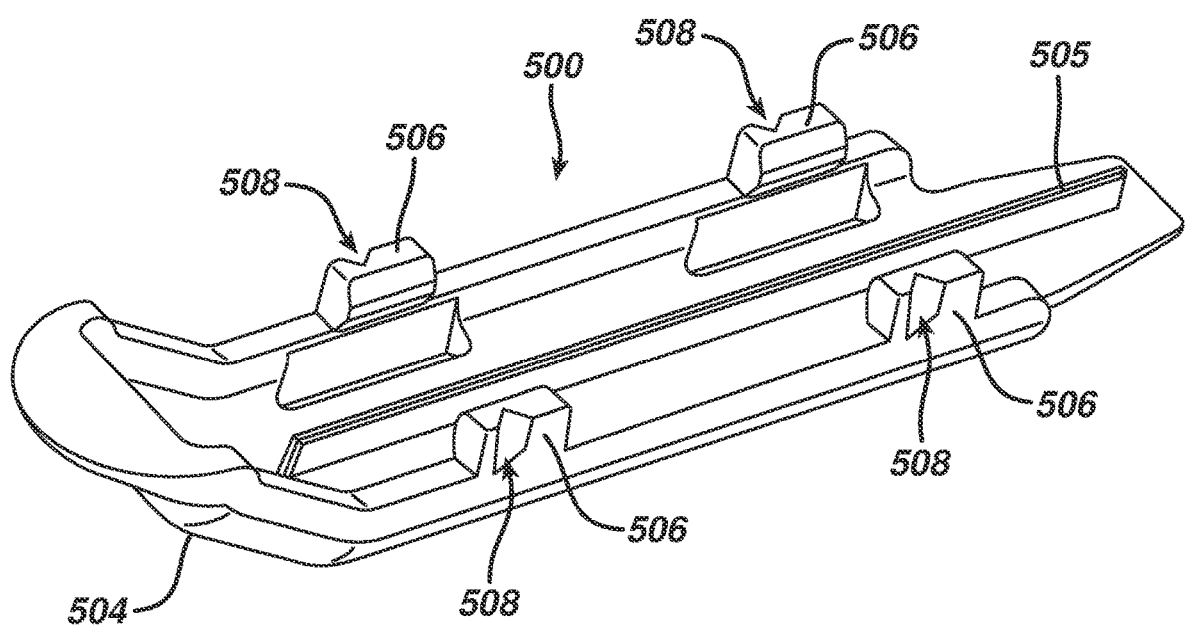
FIG. 5D is a bottom perspective view of the retainer shown in FIGS. 5A-5C, according to aspects of the present disclosure.

As shown in FIGS. 5C and 5D, the retainer 500 can be similar to the retainer 400 in that it can include a retainer tab 506 and the retainer tab 506 can include a retainer track 508. The retainer 508 (as shown in greater detail in FIG. 5H) can be substantially similar to the retainer track 408 previously described. That is, the retainer track 508 can include a first portion 507 similar to the first portion 407 and a second portion 509 similar to the second portion 409. The retainer 500, however, can further include a retainer alignment protrusion 505 that can extend outwardly from the retainer 500 toward the implantable adjunct 300 when assembled with the implantable adjunct 300. The retainer alignment protrusion 505 can be configured to extend at least partially into a channel, recess, aperture, or split in the implantable adjunct 300 to help align the retainer 500 with the implantable adjunct 300.

Figure 5E:
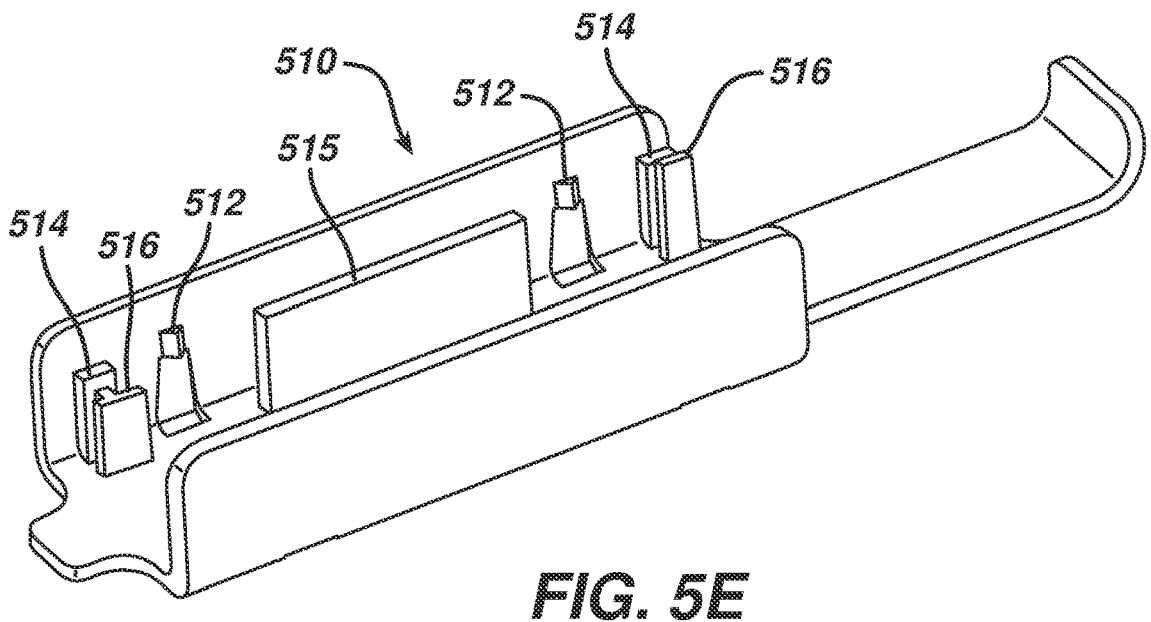
FIG. 5E is a perspective view of the pan cover shown in FIGS. 5A-5B, according to aspects of the present disclosure.
Figure 5F:
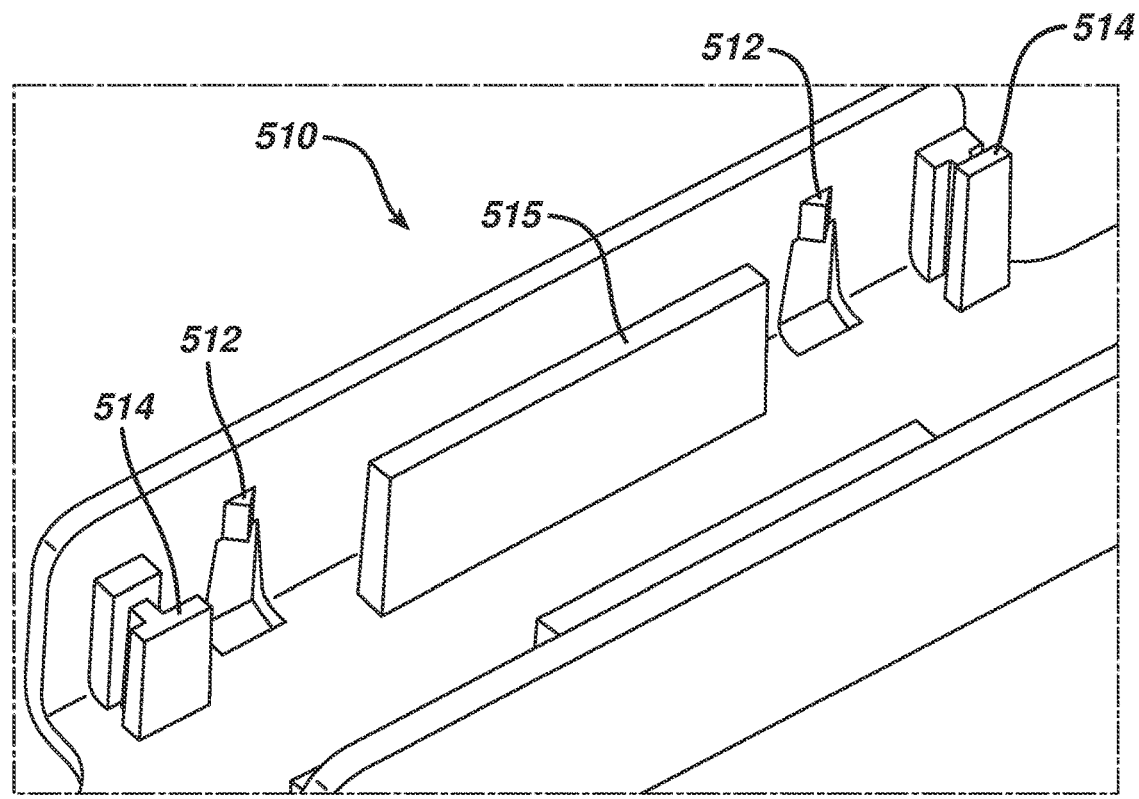
FIG. 5F is a detail view of the pan cover shown in FIGS. 5A, 5B, and 5E, according to aspects of the present disclosure.
Figure 5G:
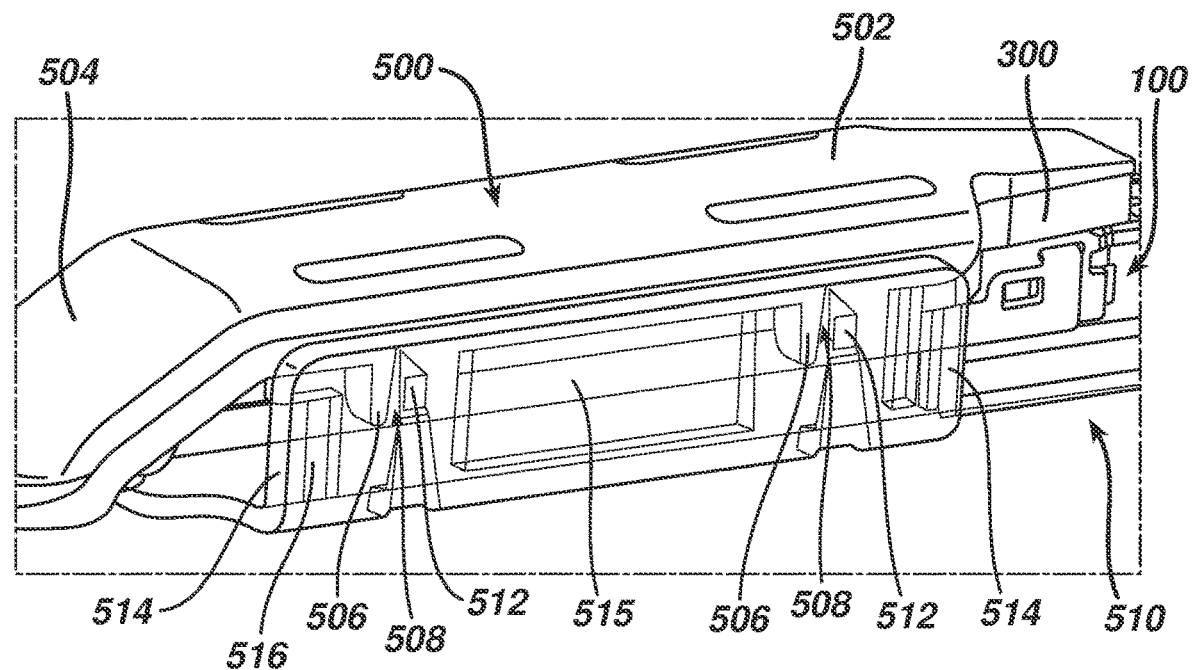
FIG. 5G is a side perspective view of the retainer and pan cover shown in FIGS. 5A-5F, according to aspects of the present disclosure.
Figure 5H:
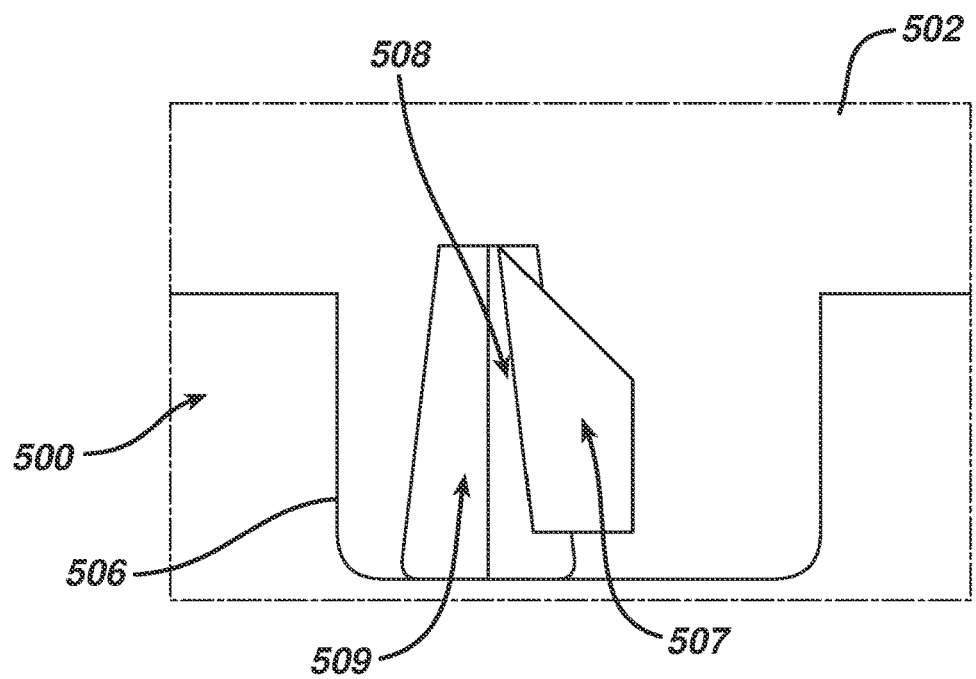
FIG. 5H is a detail view of the retainer shown in FIGS. 5A-5D, and 5G, according to aspects of the present disclosure.

As shown in FIGS. 5E and 5F, the pan cover 500 can include a pan cover protrusion 512 similar to the pan cover protrusion 412 previously described. The pan cover protrusion 512 can be configured to extend at least partially into the retainer track 508 and be configured to slide along the retainer track 508 in the same manner as described previously in relation to the retainer track 408.

Figure 5I:
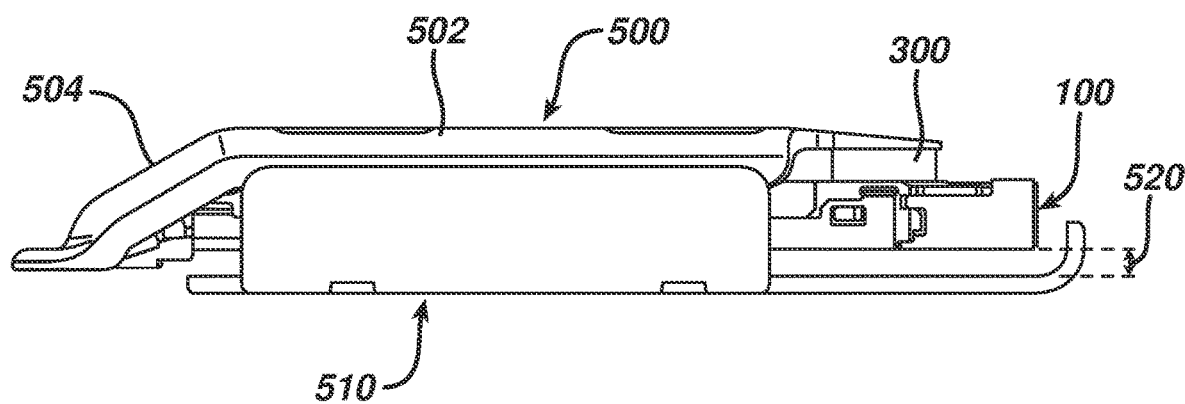
FIG. 5I is a side view of the retainer and pan cover shown in FIGS. 5A-5H, according to aspects of the present disclosure.
Figure 5J:
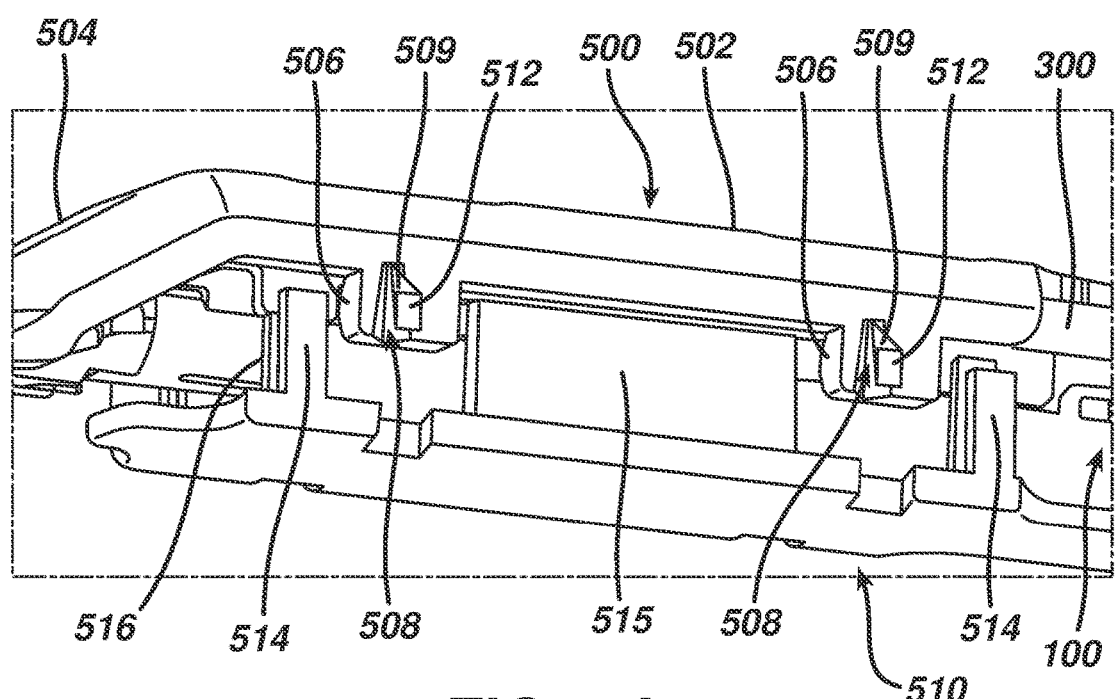
FIG. 5J is a cutaway view of the retainer and pan cover shown in FIGS. 5A-5I, according to aspects of the present disclosure.

The pan cover 510 can further include a pan cover retainer stop 514, a pan cover middle pan stop 515, and a pan cover pan stop 516. Each of the pan cover retainer stop 514, the pan cover middle pan stop 515, and the pan cover pan stop 516 can be configured to contact the retainer 500 to prevent the retainer 500 from moving further toward the pan cover 510. These features are further shown in FIG. 5G (which shows the pan cover 510 as semi-transparent), FIG. 5I, and FIG. 5J (which is cutaway view). As shown in FIG. 5I, the pan cover retainer stop 514, the pan cover middle pan stop 515, and the pan cover pan stop 516 can each be configured to stop the retainer 500 from moving closer toward the pan cover 510. In other words, the pan cover retainer stop 514, the pan cover middle pan stop 515, and the pan cover pan stop 516 can help to maintain a gap 520 between the cartridge 100 and the pan cover 510 when the retainer 500 is compressed toward the pan cover 510 and compresses the implantable adjunct 300. This can help to ensure the implantable adjunct 300 is not overly-compressed when the retainer 500 and pan cover 510 are moved toward each other.

FIGS. 6A-6J show another example of a retainer 600 and a pan cover 610 that can be used to protect an implantable adjunct 300 and cartridge 100 and to compress the implantable adjunct 300 against the deck 108, similar to examples previously described. Like the examples previously described in relation to FIGS. 4A-5J, the retainer 600 can be configured to be moved toward the pan cover 610 (e.g., pinch, compressed toward each other) to ensure the implantable adjunct 300 is properly compressed. Rather than using a retainer track (408, 508) and a pan cover protrusion (412, 512), as previously described, however, the example shown in FIGS. 6A-6J includes a hook 914 configured to latch around at least a portion of the retainer 600 as will be described in greater detail herein.

Figure 6A:
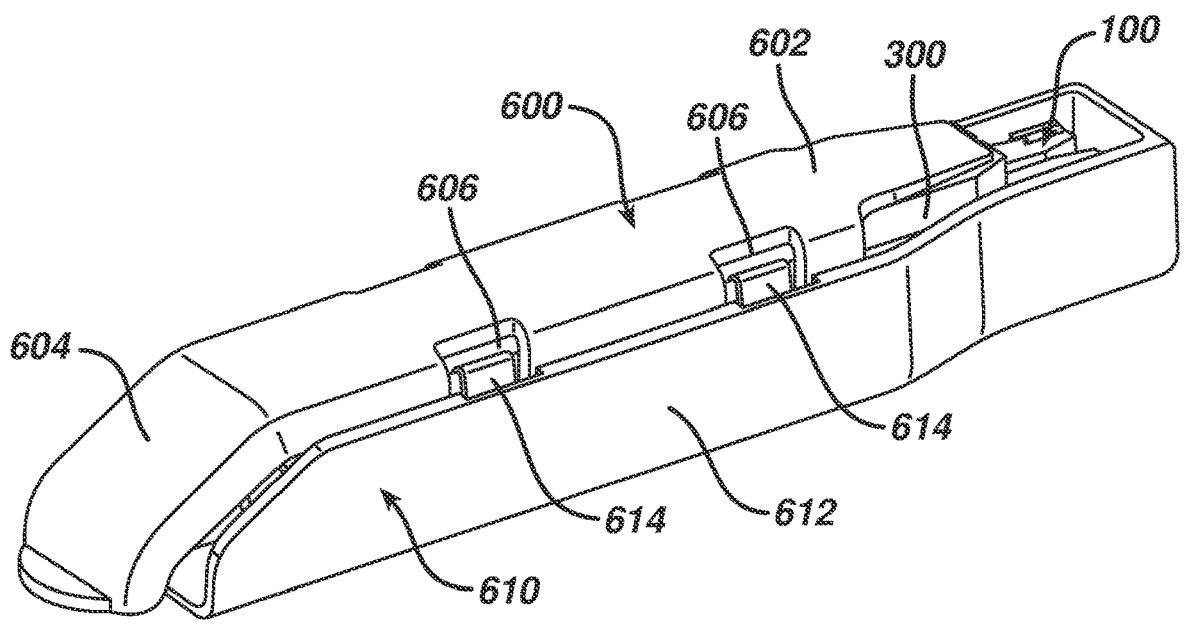
FIG. 6A is a top perspective view of another staple cartridge retainer and a pan cover, according to aspects of the present disclosure.
Figure 6B:
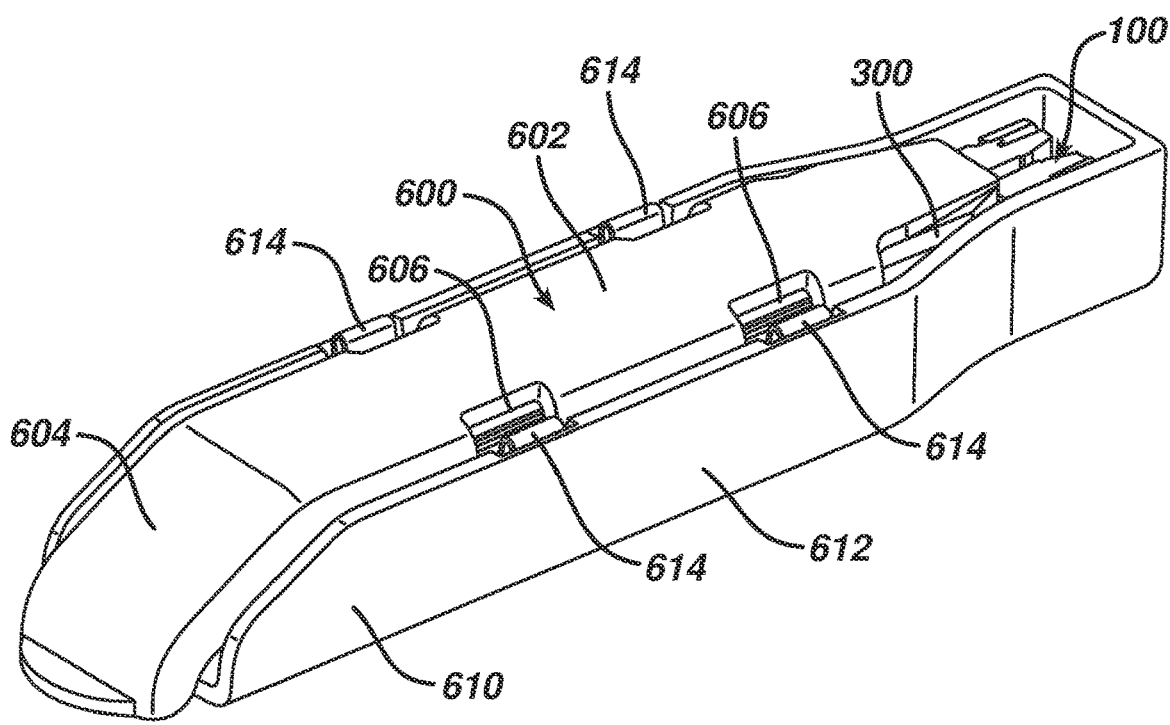
FIG. 6B is a bottom perspective view of the example staple cartridge retainer and pan cover shown in FIG. 6A, according to aspects of the present disclosure.
Figure 6C:
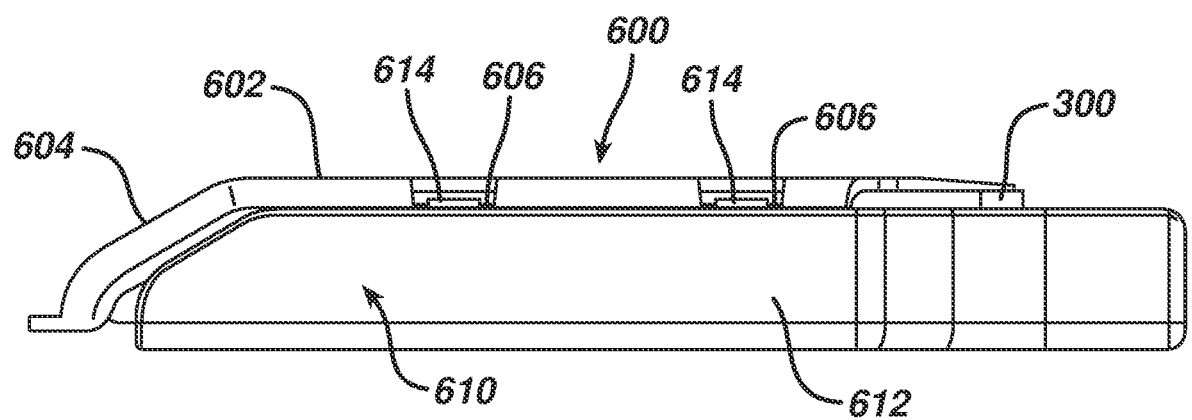
FIG. 6C is a side view of the example staple cartridge retainer and pan cover shown in FIGS. 6A and 6B, according to aspects of the present disclosure.

As shown in FIGS. 6A, 6B, and 6C, the retainer 600 includes a retainer body 602 and a retainer lever 604. The retainer lever 604 can be used to remove the retainer 600 from the cartridge 100. The pan cover 610 can include pan cover raised edges 612 that can extend upwardly toward the retainer 600. In some examples, the pan cover raised edges 612 can extend far enough toward the retainer 600 such that the implantable adjunct 300 and the cartridge 100 can be protected or inaccessible unless the retainer 600 and/or pan cover 610 are removed.

FIG. 6A illustrates the retainer 600 and pan cover 610 in an uncompressed state while FIG. 6B illustrates the retainer 600 and pan cover 610 in a compressed state (e.g., the retainer 600 has been moved toward the pan cover 610. As shown in FIG. 6A, the hooks 614 can be configured to latch onto the retainer 600 to keep the retainer 600 secured to the pan cover 610. When the retainer 600 is moved toward the pan cover 610, however, the hooks 614 can be configured to spring outwardly to disengage with the retainer 600 and permit removal of the retainer 600 from the pan cover 610.

Figure 6D:
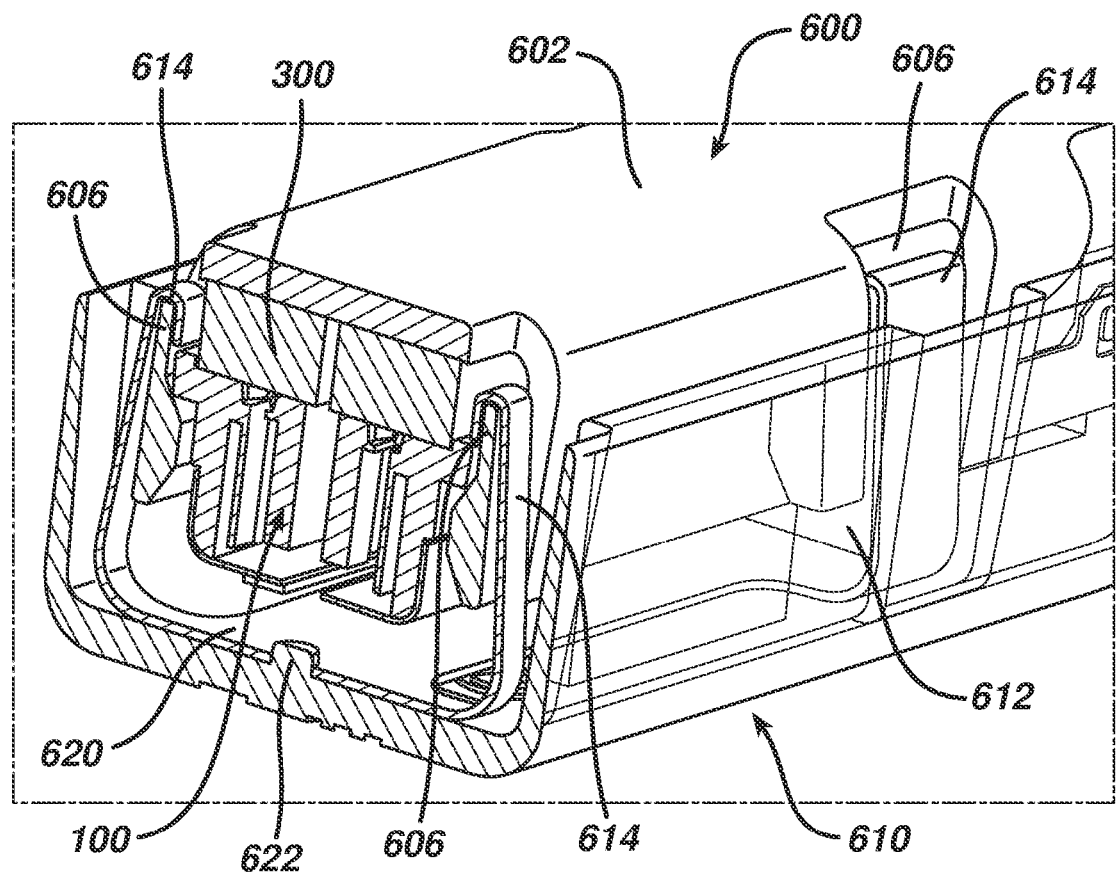
FIG. 6D is a cutaway view of the staple cartridge retainer and pan cover shown in FIGS. 6A-6C, according to aspects of the present disclosure.
Figure 6E:
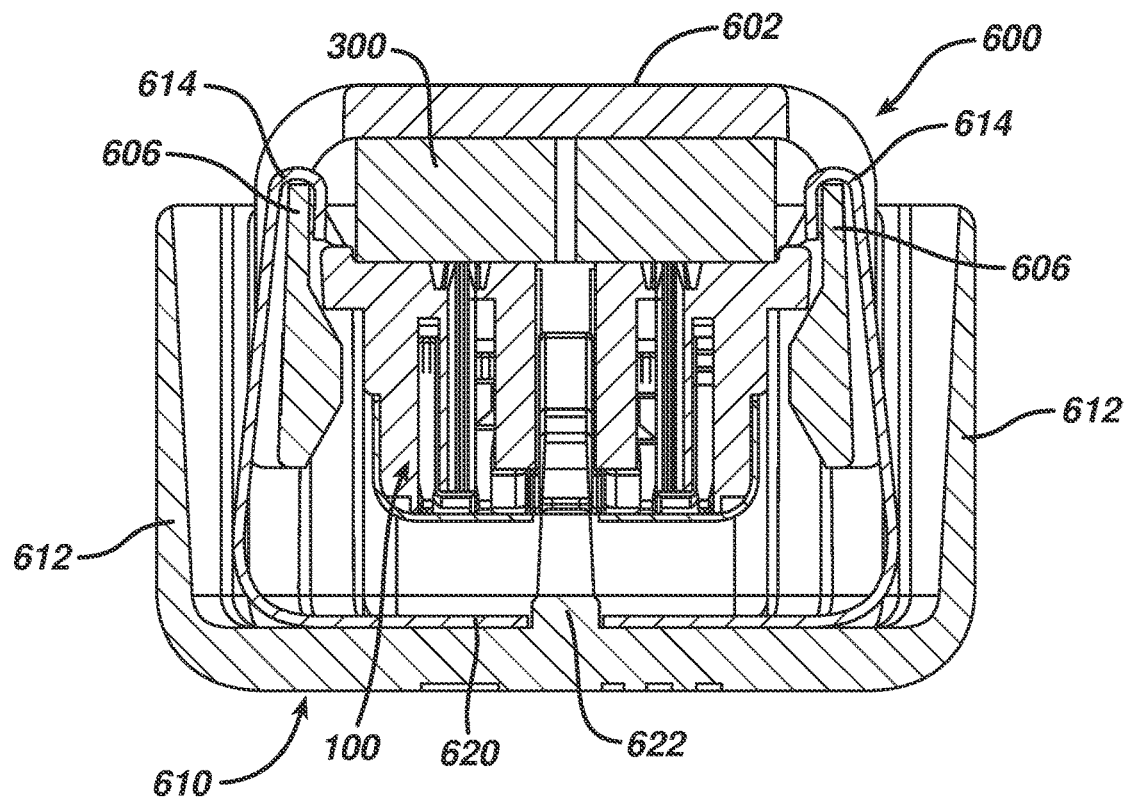
FIG. 6E is a cutaway view of the staple cartridge retainer and pan cover shown in FIGS. 6A-6D in a first position, according to aspects of the present disclosure.
Figure 6F:
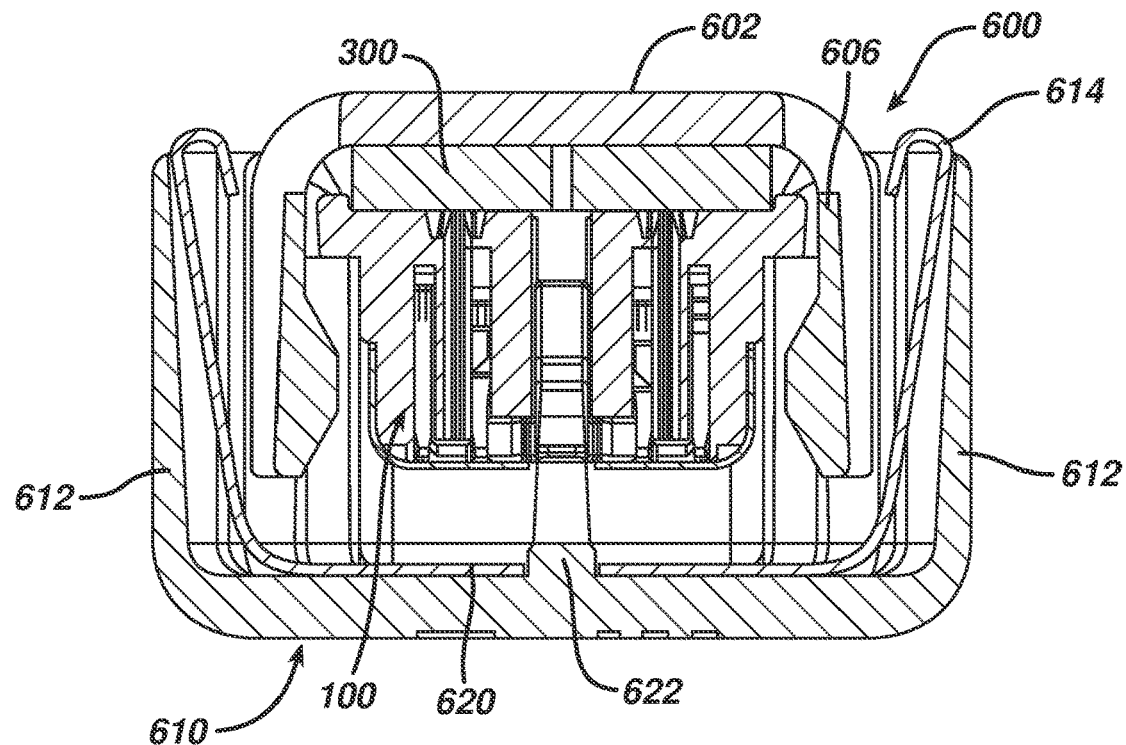
FIG. 6F is a cutaway view of the staple cartridge retainer and pan cover shown in FIGS. 6A-6E in a second position, according to aspects of the present disclosure.

Turning now to FIGS. 6D, 6E, and 6F, the operation of the hooks 614 is further described. As shown, the pan protector 610 can be attached to a spring 620 that is integrated with or otherwise attached to the hooks 614. The spring 620, for example, can be a leaf spring. In some examples, the spring 620 and the hooks 614 can be a single continuous material that is formed into the shape shown. The spring 620 can be made from a resilient or otherwise elastically deformable material that can be biased to naturally move to the position shown in FIG. 6F. The spring 620 can be attached to the pan cover 610 via a spring attachment 622. The spring attachment 622 can be a rivet, a fastener, adhesive, or any other suitable type of attachment device that is configured to attach at least a portion of the spring 620 to the pan cover 610.

As shown in FIG. 6D, the retainer 600 can include one or more apertures 606 that extend through the retainer 600 and are each aligned with, and configured to receive, the hooks 614. To attach the retainer 600 and the pan cover 610 to each other, the retainer 600 can be moved toward the pan cover 610 and the hooks 614 can be moved to align with the apertures 606. The hooks 614 can then be moved into the apertures 606 as the retainer 600 is naturally pushed upward by the implantable adjunct 300 when the implantable adjunct 300 expands or goes back to its natural uncompressed state (as shown in FIG. 6E). When the hooks 614 are attached around the retainer 600 through the apertures 606, the retainer 600 is secured to the pan cover 610.

As shown in FIG. 6F, when the retainer 600 is pushed toward the pan cover 610 and the implantable adjunct 300 is compressed, the hooks 614 will naturally spring outwardly when the hooks 614 are removed from the apertures 606 and are no longer contacting the retainer 600. Because the spring 620 naturally causes the hooks 614 to bias outwardly, the hooks 614 move out of a pathway of the retainer 600 and the retainer 600 can then be removed from the pan cover 610.

Figure 6G:
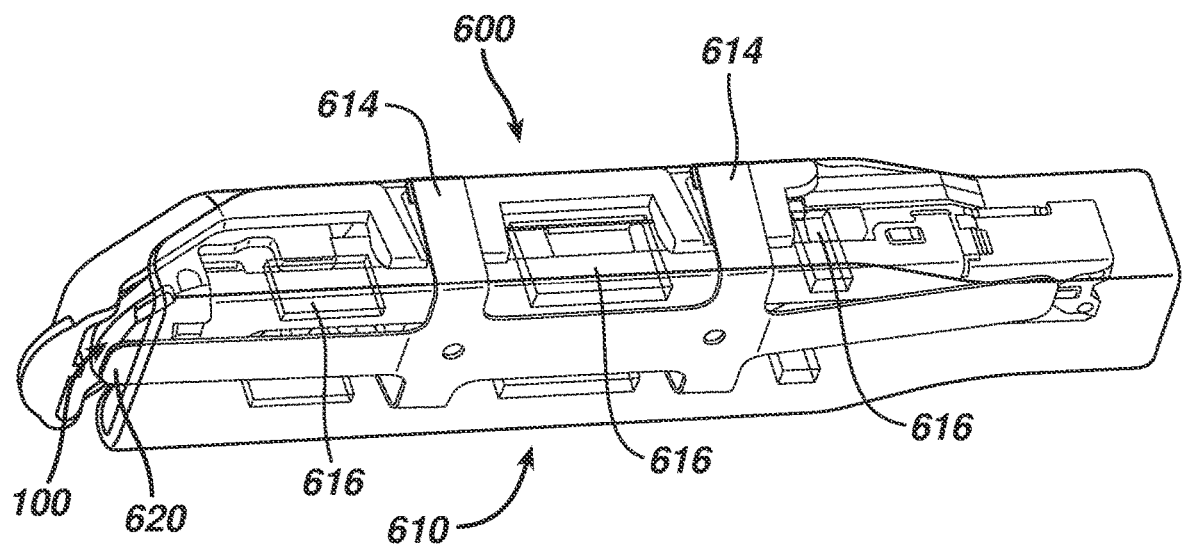
FIG. 6G is a bottom perspective view of the staple cartridge retainer and pan cover shown in FIGS. 6A-6F, according to aspects of the present disclosure.

FIG. 6G shows the retainer 600 and pan cover 610 attached to each other around the cartridge 100. The pan cover 610 is shown as semi-transparent so that the spring 620 is visible. As shown, the spring 620 can be configured to extend along the pan cover 610 and to near a proximal and a distal end of the pan cover 610. In this way, the spring 620 can be configured to push against the cartridge 100 near the proximal and the distal end as the retainer 600 is pushed inwardly toward the pan cover 610. The spring 620 can be configured to bias the hooks 614 outwardly when the cartridge 100 contacts the spring 620. Furthermore, as shown in FIG. 6G, the pan cover 610 can include pan cover stops 616 that can be configured to contact the retainer 600 and prevent over-compression of the implantable adjunct 300.

Figure 6H:
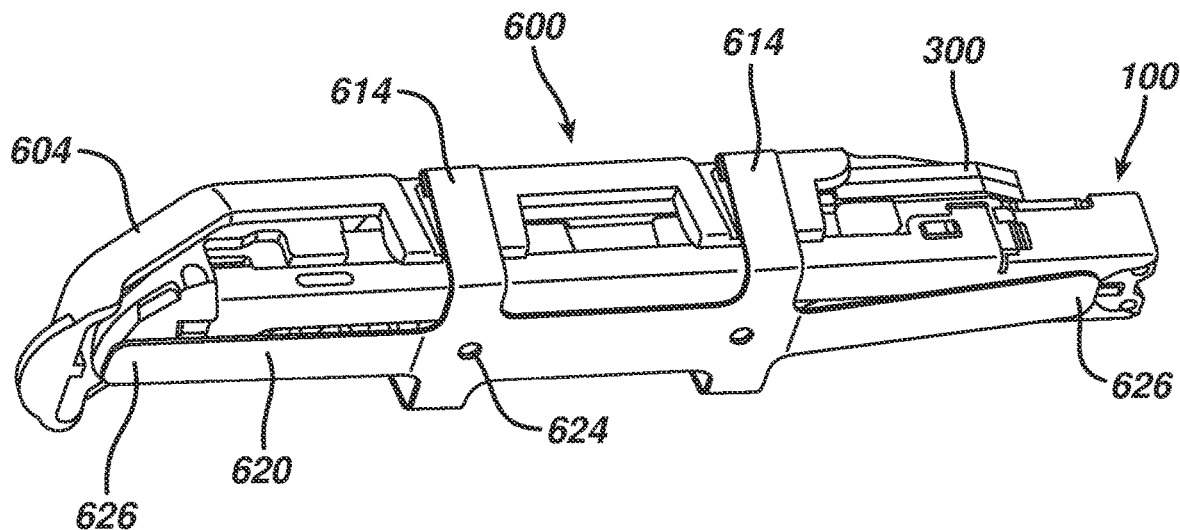
FIG. 6H is a bottom perspective view of the staple cartridge retainer shown in FIGS. 6A-6G with the pan cover removed, according to aspects of the present disclosure.
Figure 6I:
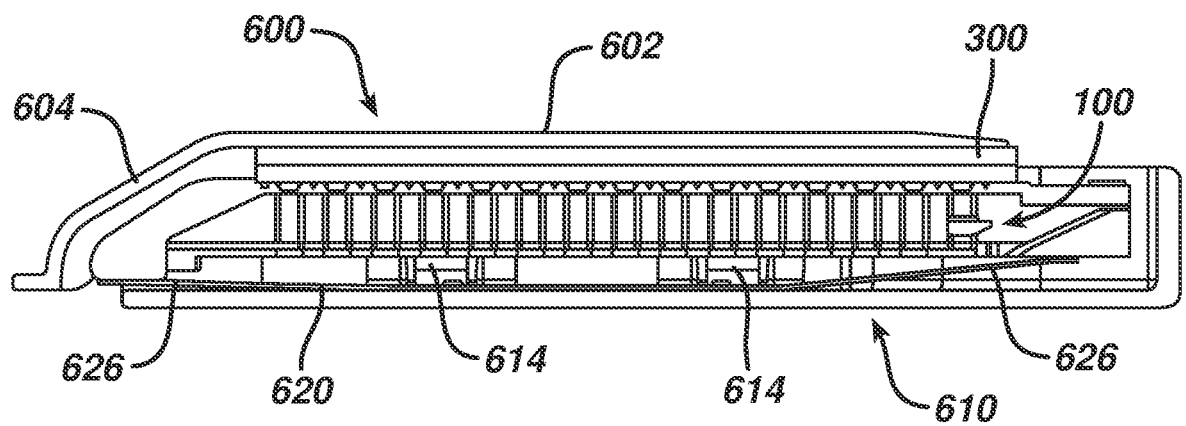
FIG. 6I is a section view of the staple cartridge retainer and pan cover shown in FIGS. 6A-6H, according to aspects of the present disclosure.
Figure 6J:
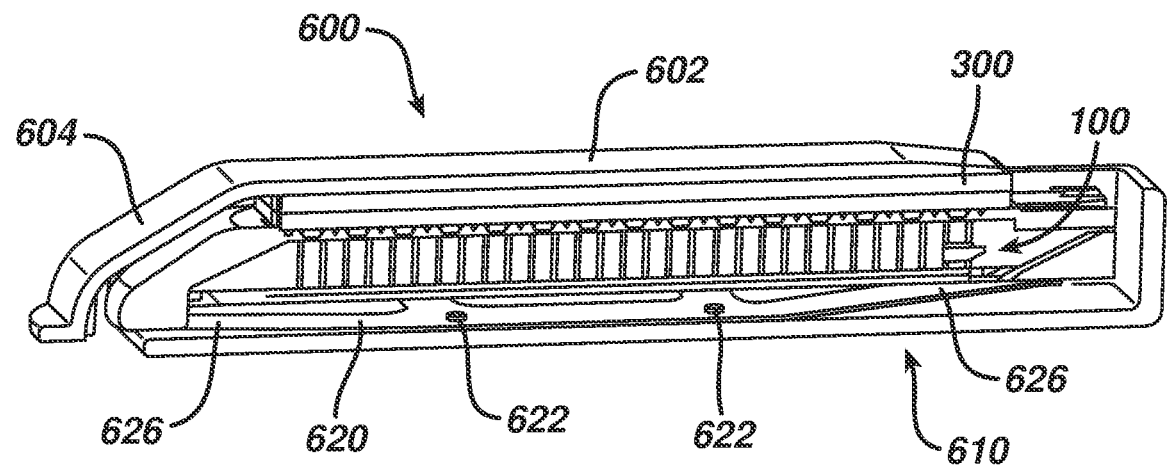
FIG. 6J is another section view of the staple cartridge retainer and pan cover shown in FIGS. 6A-6I, according to aspects of the present disclosure.

FIG. 6H offers another view of the spring 620 with the pan cover 610 removed. As shown in FIG. 6H, the spiring 620 can further include one or more apertures 624 configured to receive the spring attachment 622 and one or more bent ends 626 that can be configured to contact the cartridge 100 to push against the cartridge 100 and cause the spring 620 to cause the hooks 614 to bias outwardly. FIGS. 6I and 6J are cutaway views showing the retainer 600, the pan cover 610, the implantable adjunct 300, the cartridge 100, and the spring 620. As shown, the bent ends 626 contact the cartridge 100 as the cartridge is moved toward the pan cover 610 as a result of the retainer 600 being pushed toward the pan cover 600. As the spring 620 contacts the cartridge 100, the spring force is distributed along the spring 620 to the hooks 614 to bias the hooks outwardly. In this way, the hooks 614 can be configured to disengage from the retainer 600 and move out of a pathway of the retainer 600 to allow for removal of the retainer 600 from the pan cover 610. It will also be appreciated that the disclosed technology shown and described in relation to FIGS. 6A-6J is configured to ensure the implantable adjunct 300 is properly compressed prior to use.

Turning now to FIGS. 7A-7E, another example of a retainer 700 and pan cover 710 are shown and described. The retainer 700 can b substantially similar to the retainer 600 just described and can include a retainer body 702, a retainer lever 704, and one or more apertures 706. The pan cover 710, however, can include a spring 720 that is integrated into the pan cover 710 as will be described in greater detail herein.

As shown in FIGS. 7A-7E, the pan cover 610 can include raised edges 712 and the springs 714 and pan cover stops 718 can be formed into the body of the pan cover 610. Similar to the example shown and described in relation to FIGS. 6A-6I, the hooks 714 can be configured to extend into apertures 706 formed in the retainer 700 to attached the retainer 700 to the pan cover 710. The hooks 714 and the spring 720 can be integrally formed into the pan cover 710 such that the hooks 714 are formed into the raised edges 712 and are configured to bias outwardly. For example, the spring 720 and hooks 714 can be heat formed to naturally move to a state in which the hooks are biased outwardly from the retainer 700 to permit removal of the retainer 700 from the pan cover 710 after moving the retainer 700 toward the pan cover 710 to compress the implantable adjunct 300. In this way, the hooks 714 can be configured to bias outwardly without the need for the bent ends as previously described (bent ends 626).

Figure 7A:
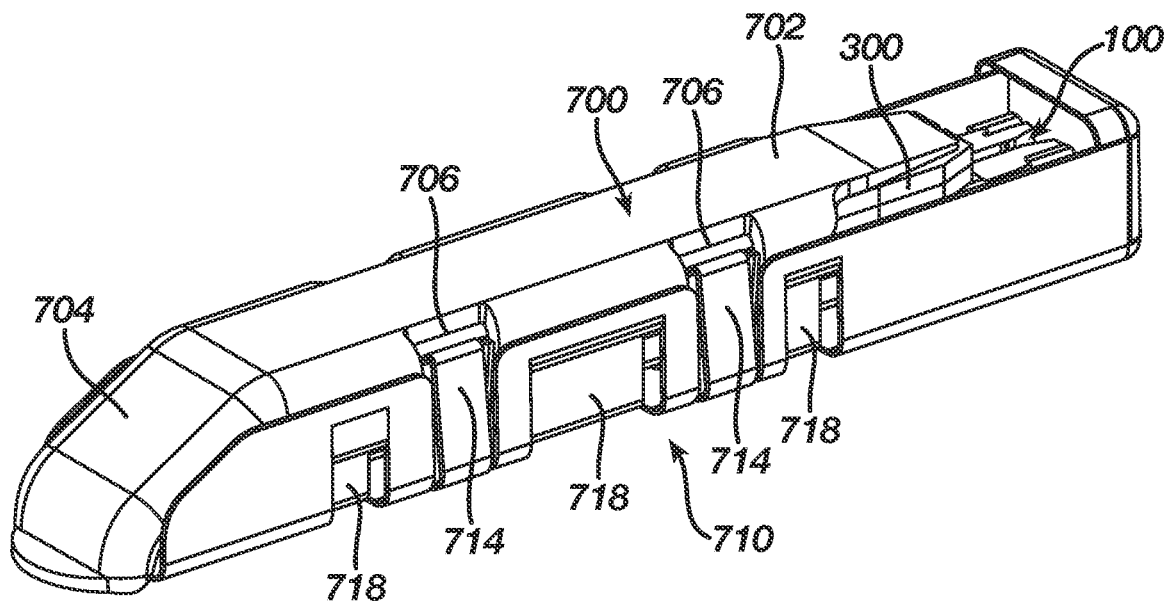
FIG. 7A is a top perspective view of yet another example staple cartridge retainer and a pan cover, according to aspects of the present disclosure.
Figure 7B:
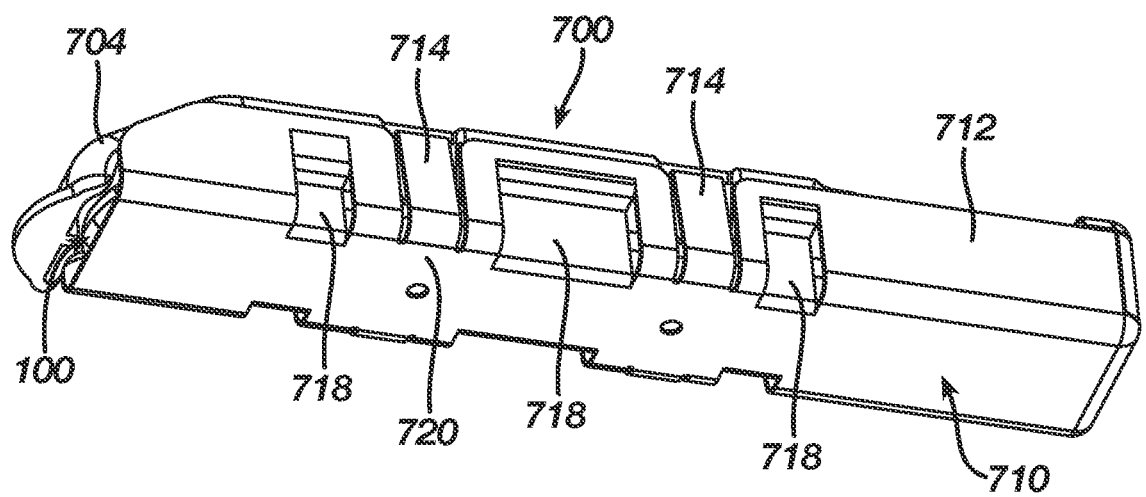
FIG. 7B is a bottom perspective view of the example staple cartridge retainer and pan cover shown in FIG. 7A, according to aspects of the present disclosure.
Figure 7C:
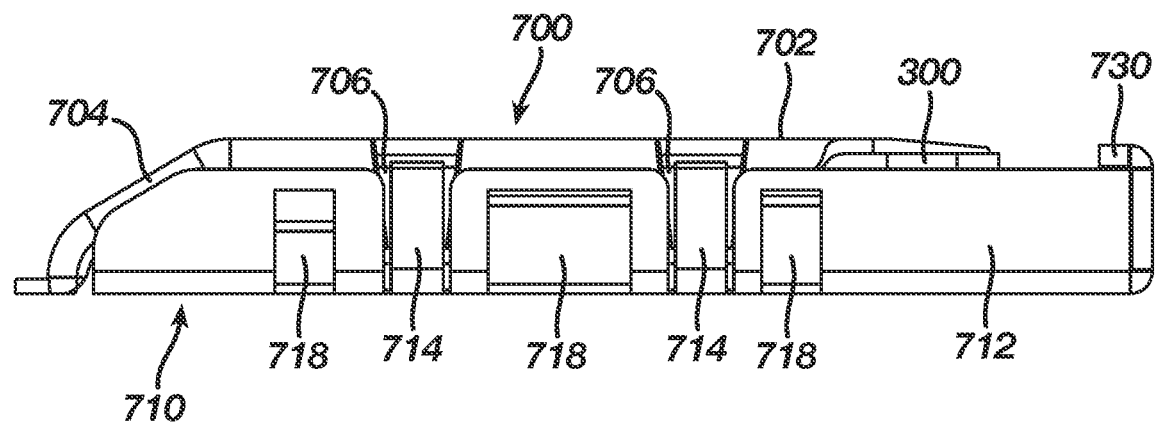
FIG. 7C is a side view of the example staple cartridge retainer and pan cover shown in FIGS. 7A and 7B, according to aspects of the present disclosure.
Figure 7D:
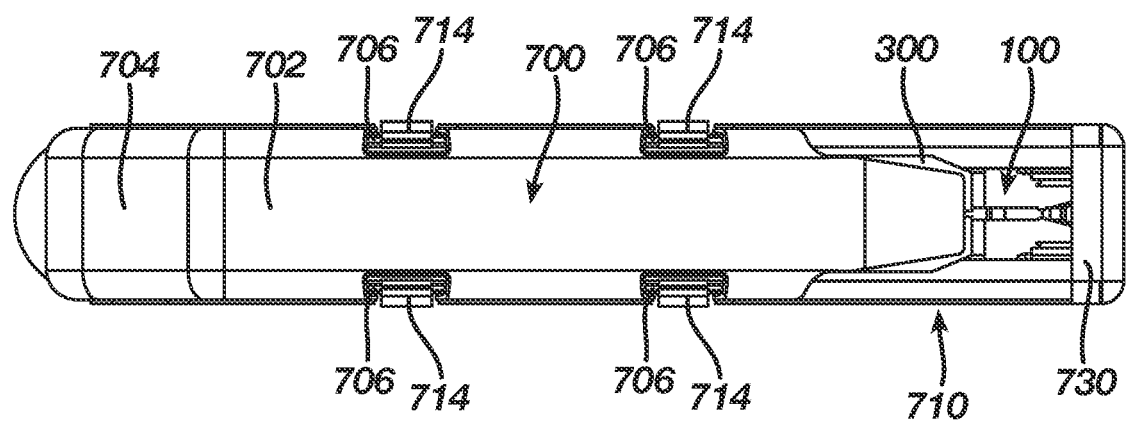
FIG. 7D is a cutaway view of the pan cover shown in FIGS. 7A-7C, according to aspects of the present disclosure.
Figure 7E:
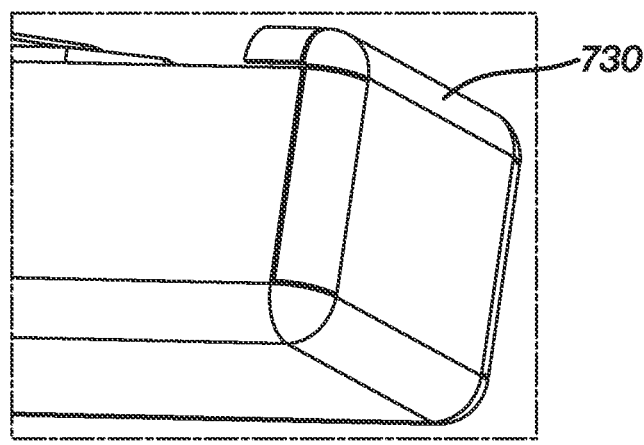
FIG. 7E is a detail view of an end of the pan cover shown in FIGS. 7A-7D, according to aspects of the present disclosure.

As shown best shown in FIG. 7E but also shown in FIGS. 7A-7D, the pan cover 710 can include a closed end 730 that can help to provide further protection to the cartridge 100 when assembled with the cartridge 100. As will be appreciated, the example just shown and described in relation to FIGS. 7A-7E can be configured to protect the implantable adjunct 300 and the cartridge 100 during shipment and prior to use while also being configured to ensure a user must compress the implantable adjunct 300 prior to use. As before, it be appreciated that the disclosed technology shown and described in relation to FIGS. 7A-7E is configured to ensure the implantable adjunct 300 is properly compressed prior to use.

Figure 8A:
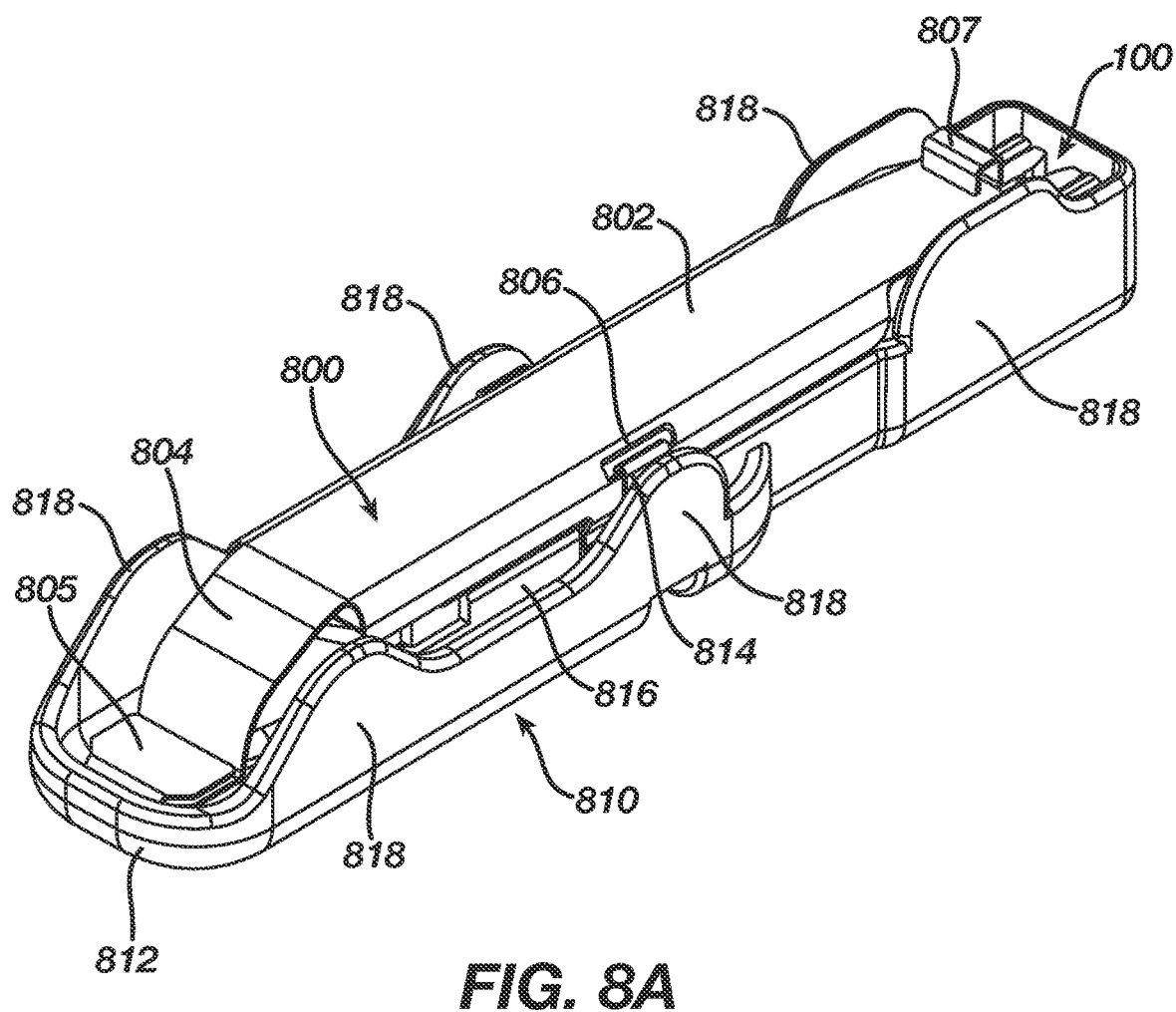
FIG. 8A is a top perspective view of still another example staple cartridge retainer and a pan cover, according to aspects of the present disclosure.
Figure 8B:
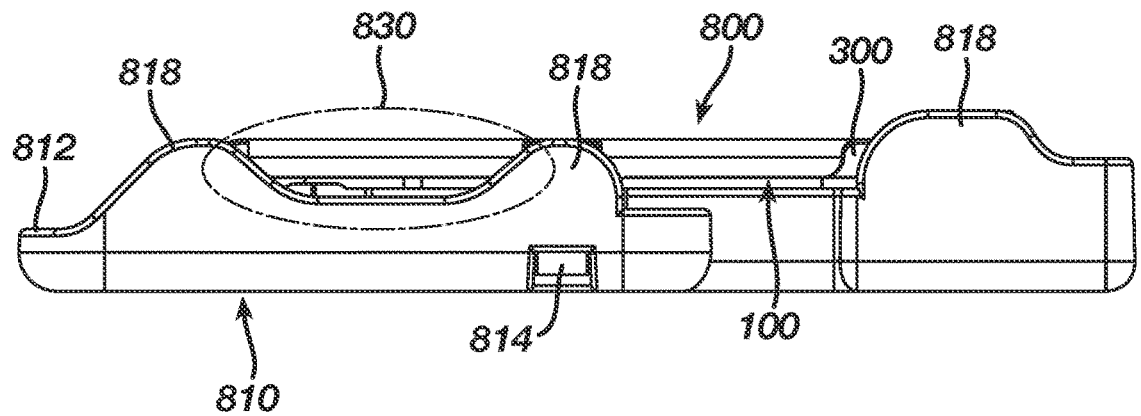
FIG. 8B is a side view of the example staple cartridge retainer and pan cover shown in FIG. 8A, according to aspects of the present disclosure.
Figure 8C:
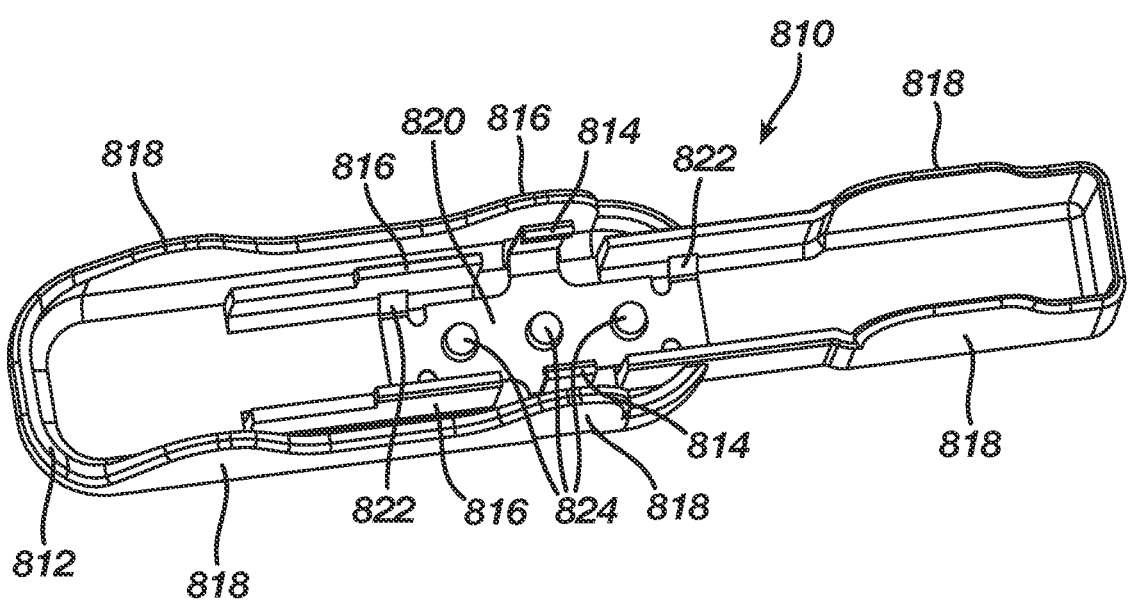
FIG. 8C is a top perspective view of the example pan cover shown in FIGS. 8A and 8B, according to aspects of the present disclosure.

Turning now to FIGS. 8A-8C, another example retainer 800, pan cover 810, implantable adjunct 300, and cartridge 100 are shown. The retainer 800 can be similar to the retainers 600 and 700 in that the retainer 800 can include a retainer body 802, a retainer lever 804, and one or more apertures 806. The retainer 800, however, can further include a retainer distal tab 805 and a retainer proximal tab 807. The retainer distal tab 805 and the retainer proximal tab 807 can each be configured to be gripped or otherwise used by the user to remove the retainer 800 from the pan cover 810.

The pan cover 810 can include a raised edge 812 that can extend around the distal end or around the entire pan cover 810 to help protect the cartridge 100. The pan cover 810 can further include one or more pan cover stops 816 that can prevent the retainer 800 from coming too close to the pan cover 810 and over-compressing the implantable adjunct 300. The pan cover 810 can further include finger guides 818 that can extend upwardly from the raised edge 812 or otherwise be integrally formed into the raised edge 812 to form one or more finger cut-outs 830 as illustrated in FIG. 8B. The finger cut-outs 830 can enable a user to place his or her fingers across the retainer 800 and push downward on the retainer 800 in a direction transverse to a length of the retainer 800. In other words, by having the finger cut-out 828, it can be easier for a user to pinch the retainer 800 toward the pan cover 810 because the user's fingers do not contact the raised edge 812.

FIG. 8C illustrates the pan cover 810 and shows the spring 820. As shown, the spring 820 can be attached to the pan cover 810 via one or more spring attachments 824. The spring 820 can further include one or more spring engagement features 822 that can be configured to engage the pan cover 810 and, when pinched or crimped against the pan cover 810, can help to cause the spring 820 to bend slightly and cause the hooks 814 to bias outwardly. As before, it be appreciated that the disclosed technology shown and described in relation to FIGS. 8A-8C is configured to ensure the implantable adjunct 300 is properly compressed prior to use.

Turning now to FIGS. 9A-9D, another example of the disclosed technology that is configured to protect the cartridge 100 and implantable adjunct 300 is shown and described. Rather than including a pan protector like described in previous examples, the example shown in FIGS. 9A-9D can include a first retainer 900 and a second retainer 910. The first retainer 900 can be positioned nearest the implantable adjunct 300 and the second retainer 910 ca be positioned at least partially over the first retainer 900.

Figure 9A:
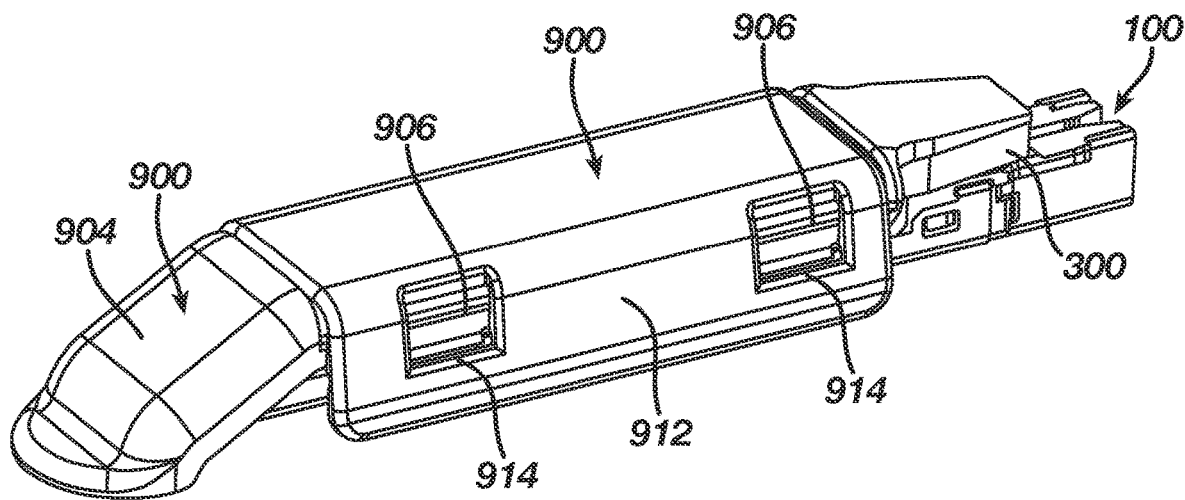
FIG. 9A is a top perspective view of a first and second retainer, according to aspects of the present disclosure.
Figure 9B:
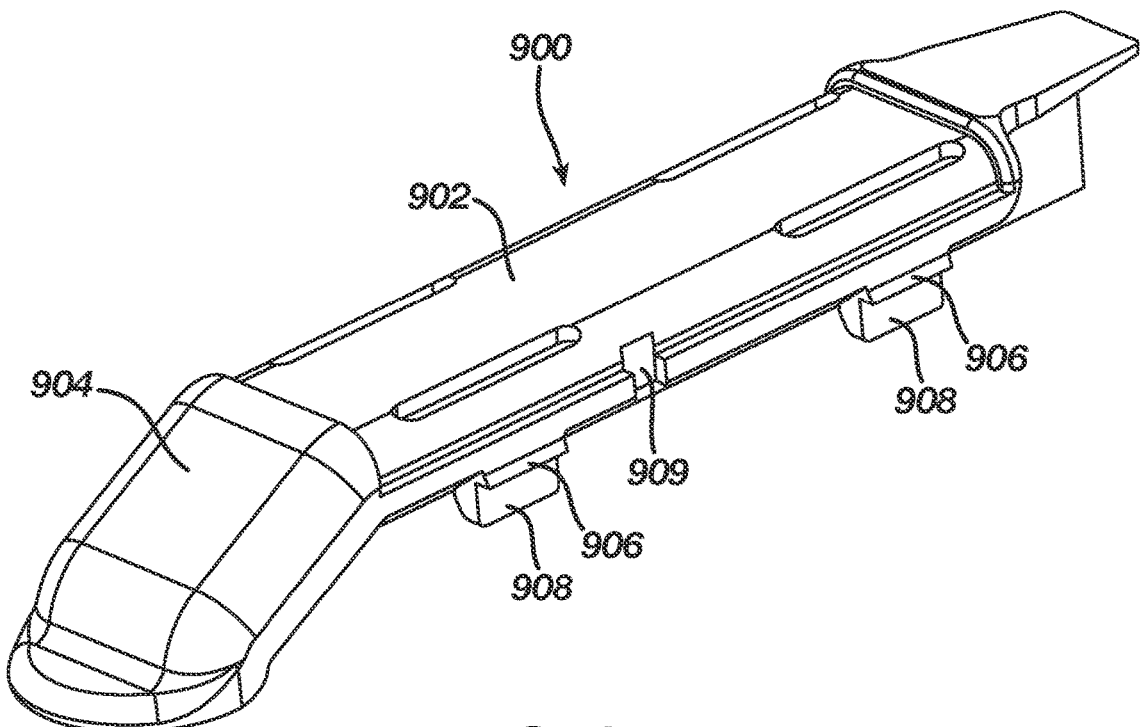
FIG. 9B is a top perspective view of the first retainer shown in FIG. 9A, according to aspects of the present disclosure.
Figure 9C:
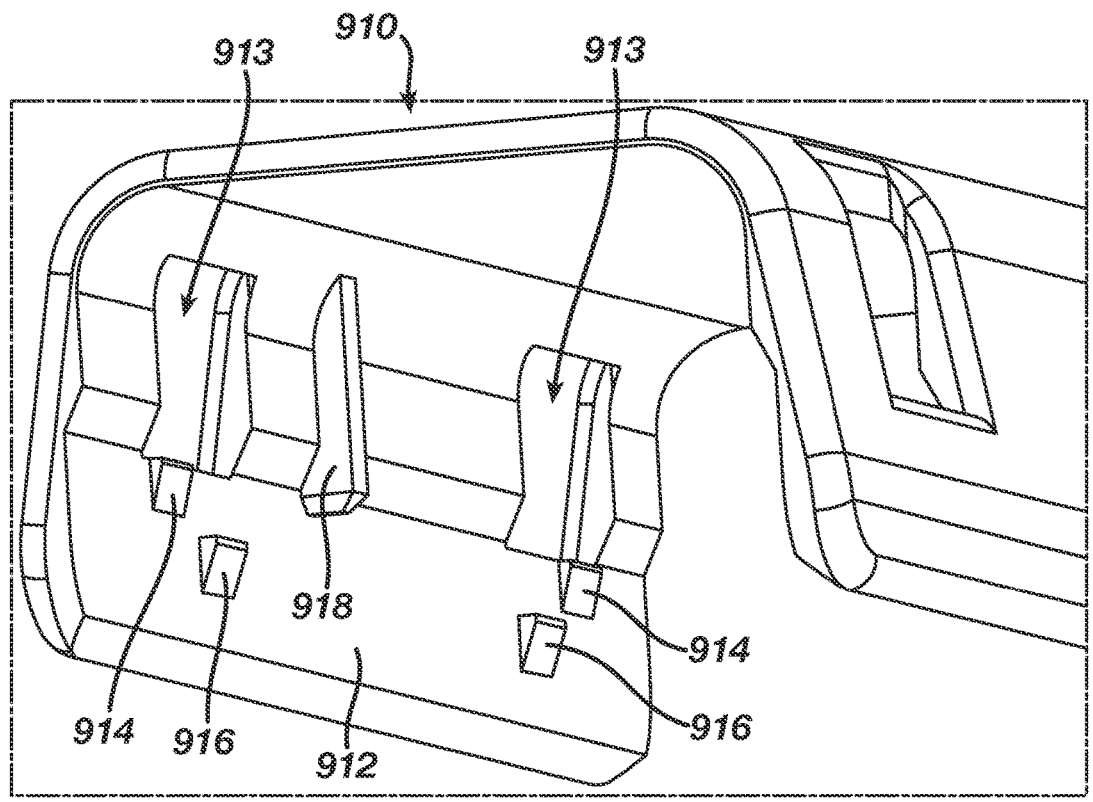
FIG. 9C is a perspective view of the second retainer shown in FIG. 9A, according to aspects of the present disclosure.

To ensure the implantable adjunct 300 is sufficiently compressed between the cartridge 100 and the first retainer 900, the first retainer 900 and the second retainer 910 can include features that provide feedback to a user indicating that the implantable adjunct 300 is sufficiently compressed. For example, the first retainer can include a first retainer protrusion 906 that extends outwardly from the first retainer 900 on a first retainer tab 908 and is configured to engage a second retainer lower protrusion 916 during shipping and prior to compression of the adjunct 300. As shown in FIG. 9C, the second retainer 910 can further include a second retainer upper protrusion 914 that can be configured to engage with the first retainer protrusion when the second retainer 910 is compressed against the first retainer 900 and the first retainer 900 receives a sufficient opposite force provided by the adjunct 300 (e.g., when the adjunct 300 is sufficiently compressed). When the first retainer protrusion 906 engages with the second retainer upper protrusions 914, the user will hear an audible click and may feel a sudden jerk in first retainer 900 and/or the second retainer 910 indicating that the adjunct 300 has been sufficiently compressed. In this way, the user can know when the adjunct 300 has been sufficiently compressed and the first retainer 900 can be removed. The second retainer 910 can further include a second retainer alignment tab 918 that can be configured to extend at least partially into a first retainer recess 909 to help ensure the second retainer 910 is properly aligned with the first retainer 900 so the first retainer protrusions 906 properly align with the second retainer upper protrusions 914 and second retainer lower protrusions 916.

Figure 9D:
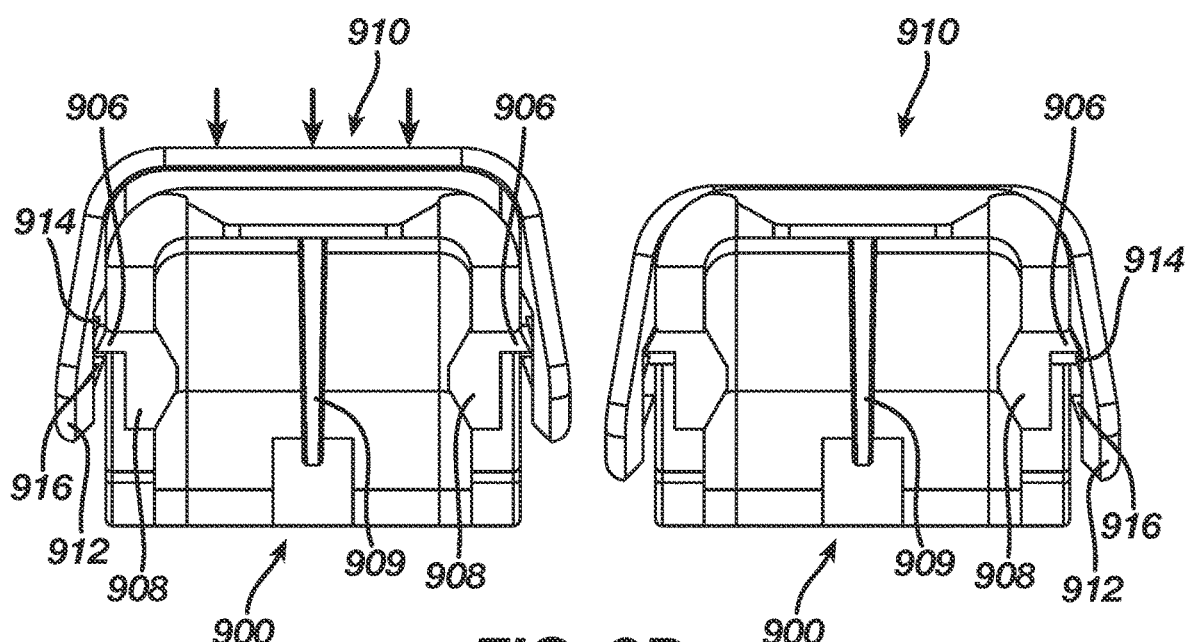
FIG. 9D is a front view of the first retainer and second retainers shown in FIGS. 9A-9C, according to aspects of the present disclosure.

The first retainer 900 and the second retainer 910 can be packaged and shipped to the user in the configuration shown on the left in which the first retainer protrusions 906 are engaged with the second retainer lower protrusions 916 but not the second retainer upper protrusions 914. As shown in FIG. 9D, the second retainer 910 can be pushed against the first retainer 900 to cause the first retainer protrusions 906 to engage with the second retainer upper protrusions 914. Once the first retainer protrusions 906 to engage with the second retainer upper protrusions 914 and the audible click is heard (or felt), the user can know that the adjunct 300 is sufficiently compressed and the first retainer 900 and the second retainer 910 can then be removed from the cartridge 100 via the first retainer lever 904.

Turning now to FIGS. 10A-10F another example of a first retainer 1000 and second retainer 1010 are shown and described. Similar to the example shown and described in relation to FIGS. 9A-9D, the example shown in FIGS. 10A-10F can include a first retainer 1000 and a second retainer 1010 configured to engage with the first retainer 1010 and to provide an audible click once the second retainer 1010 has been sufficiently pushed against the first retainer 1000 to sufficiently compress the adjunct 300.

The first retainer 1000 can include a first retainer body 1002 that has a first retainer alignment tab 1004. The first retainer alignment tab 1004 can be configured to extend at least partially into the implantable adjunct 300 and the cartridge 100. The first retainer 1000 further includes a first retainer protrusion 1006 that can extend outwardly from the first retainer 1000 and be configured to engage with a second retainer upper protrusion 1014 and a second retainer upper protrusion 1016.

The second retainer 1010 includes a second retainer body 1012, a second retainer upper protrusion 1014, and a second retainer lower protrusion 1016. The first retainer 1000 can be attached to the second retainer 1010 be having the first retainer protrusions 1006 engage with the second retainer lower protrusions 1016. As before, the second retainer 1010 can be pushed against the first retainer 1000 until the first retainer protrusions 1006 engage with the second retainer upper protrusions 1014 such that an audible click is heard. At this point, the user can know that the adjunct 300 has been sufficiently compressed.

The second retainer 1010 can further include a second retainer sloped end 1020, a second retainer lever 1022 extending outwardly from the second retainer sloped end 1020, and a second retainer lever tab 1024. The second retainer lever tab 1024 can be configured to extend at least partially around the cartridge 100 such that the first retainer 1000 and second retainer 1010 are prevented from being removed from the cartridge until the second retainer lever 1022 is actuated and the second retainer sloped end 1020 bends outwardly, thereby causing the second retainer lever tab 1024 to move away from the cartridge 100 to release the cartridge 100.

Figure 10A:
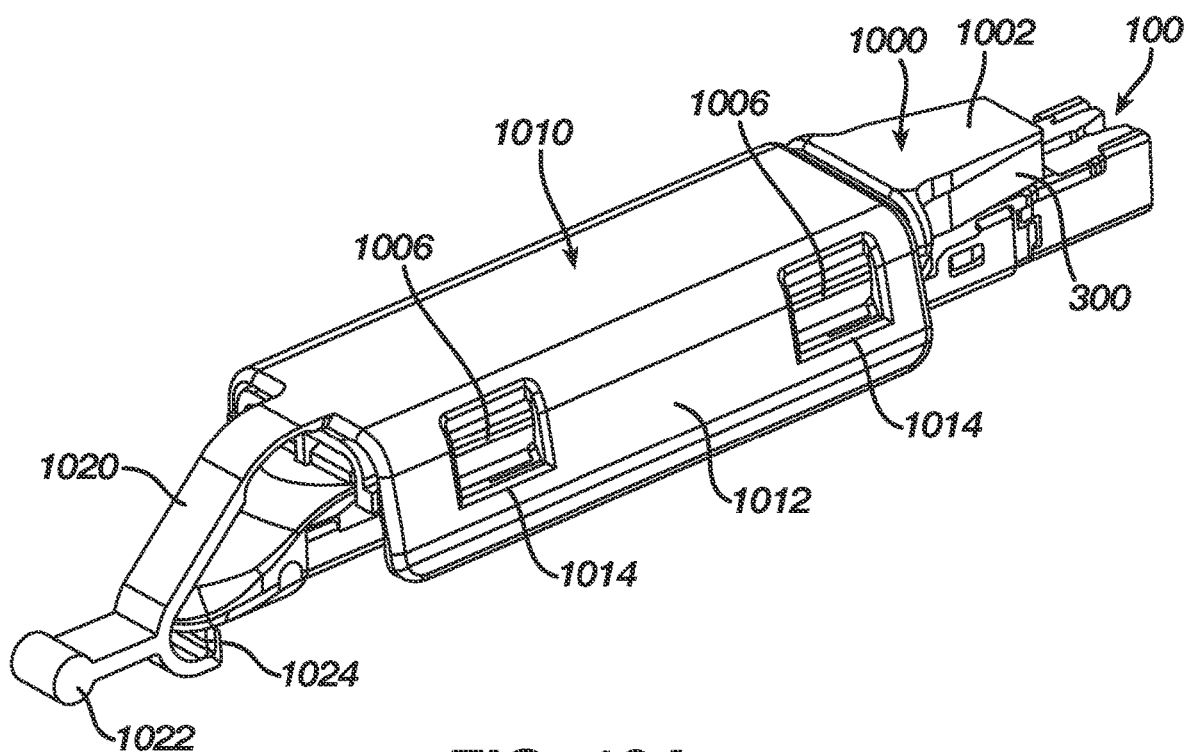
FIG. 10A is a top perspective view of another example first and second retainer with a staple cartridge, according to aspects of the present disclosure.
Figure 10B:
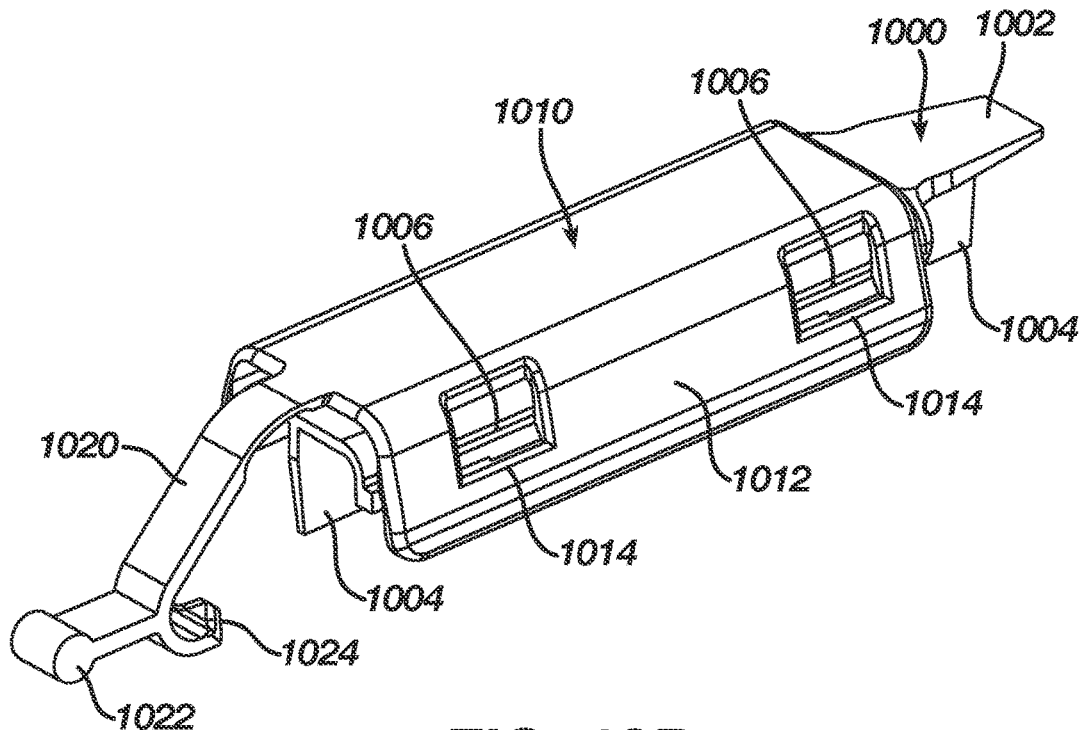
FIG. 10B is a top perspective view of first and second retainer shown in FIG. 10A with the staple cartridge removed, according to aspects of the present disclosure.
Figure 10C:
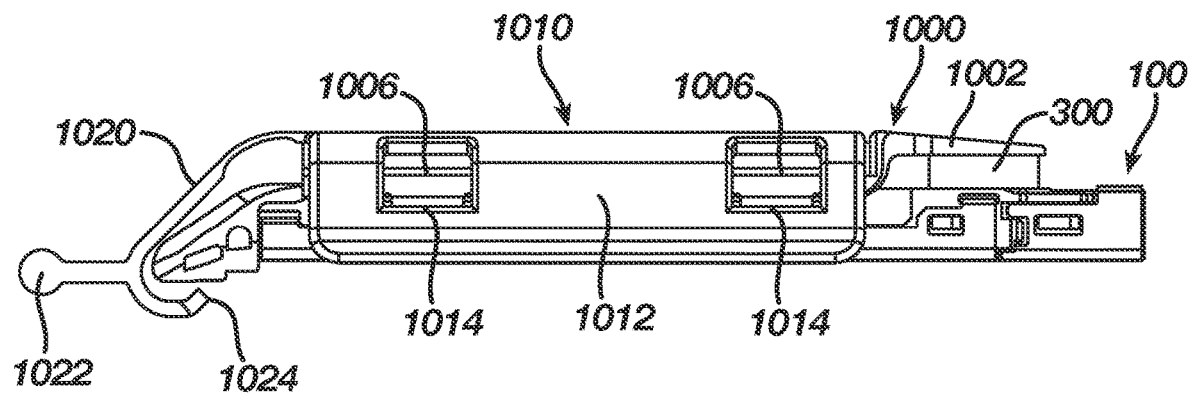
FIG. 10C is a side view of the first and second retainer shown in FIGS. 10A and 10B with the staple cartridge, according to aspects of the present disclosure.
Figure 10D:
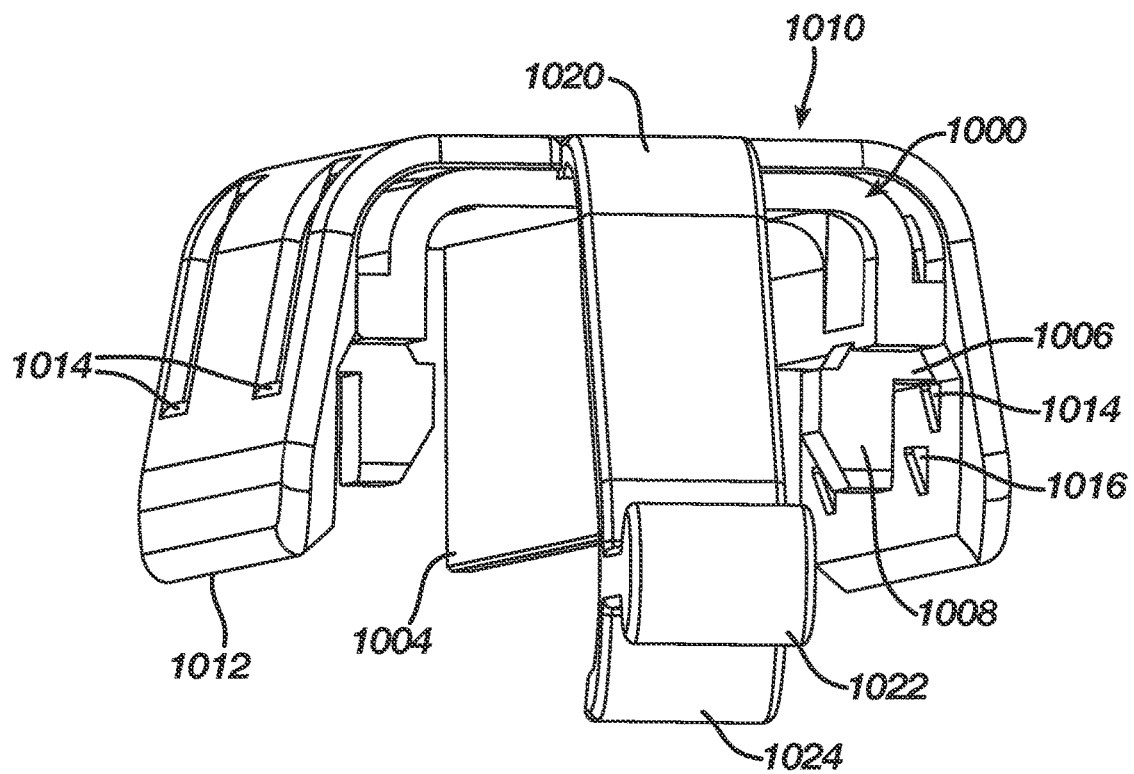
FIG. 10D is a front perspective view of first and second retainer shown in FIGS. 10A-10C with the staple cartridge removed, according to aspects of the present disclosure.
Figure 10E:
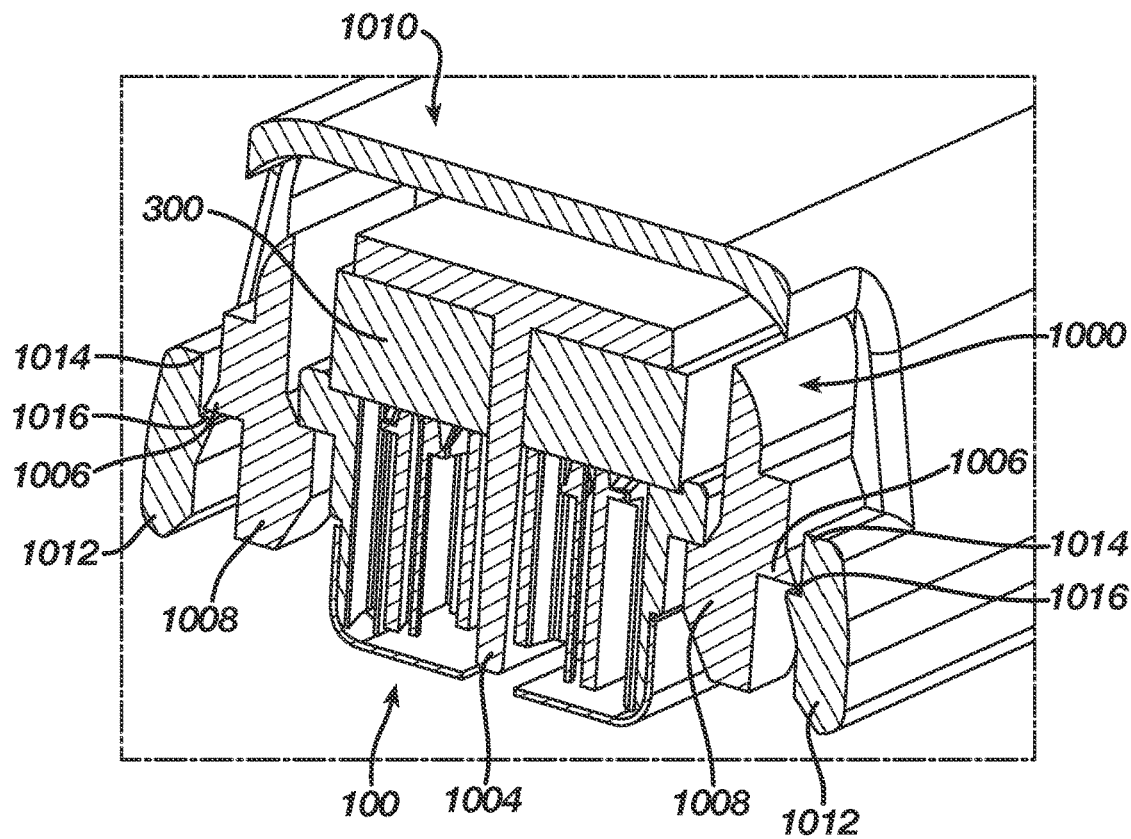
FIG. 10E is a perspective view of the first and second retainer shown in FIGS. 10A-10D with the staple cartridge, according to aspects of the present disclosure.
Figure 10F:
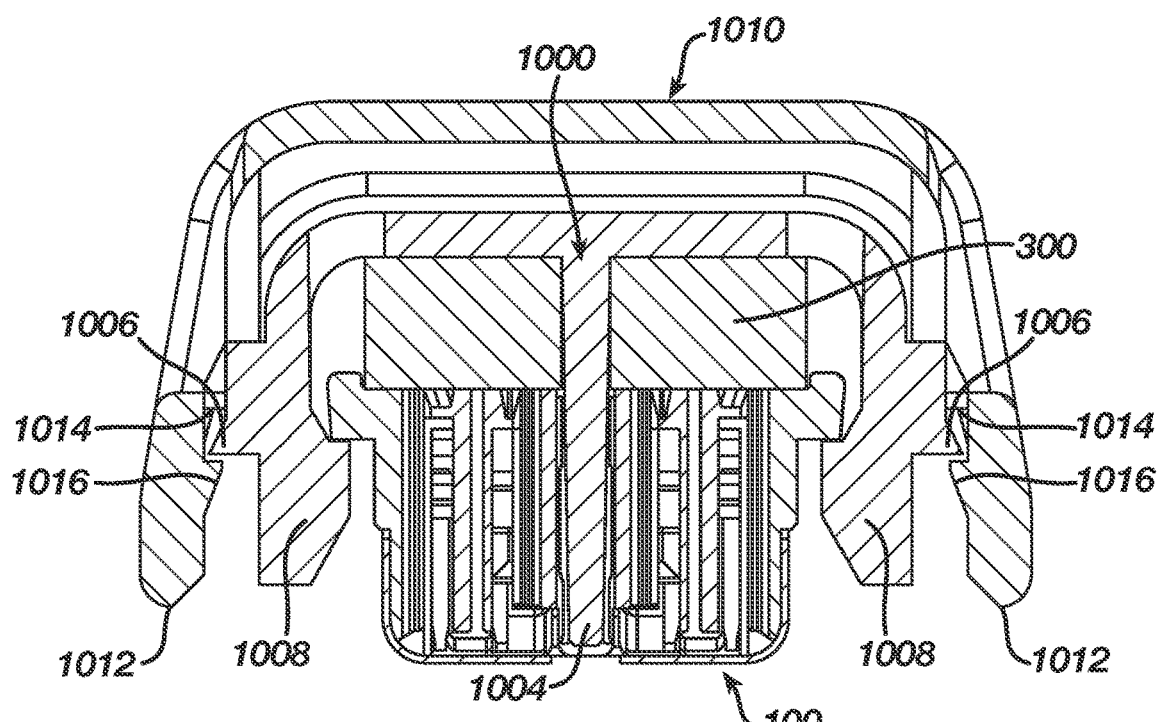
FIG. 10F is a front view of the first and second retainer shown in FIGS. 10A-10E with the staple cartridge, according to aspects of the present disclosure.

Turning now to FIGS. 10E and 10F, the features just described (the first retainer protrusion 1006, the second retainer upper protrusion 1014, and the second retainer lower protrusion 1016) are shown in greater detail. Furthermore, as shown, the first retainer 1008 can further include a first retainer sloped edge 1008. The first retainer sloped edge 1008 can enable easier assembly of the first retainer 1000 to the cartridge 100. For example, the sloped edge 1008 can be configured to slide along an outer edge of the cartridge 100 until the first retainer 1000 is attached to the cartridge 100. The first retainer sloped edge 1008 can be further configured to engage with the channel 206 when the cartridge 100 is inserted in the channel 206. For instance, the sloped edge 1008 can slide over an outer edge of the channel 206 and splay outer walls of the first retainer 1000 until the first retainer 1000 can be removed from the cartridge 100. The first retainer 1000 and second retainer 1010 can be removed from the cartridge 100 once the outer walls of the first retainer 1000 splay outwardly by using the retainer lever 1022.

Turning now to FIGS. 11A-11D, another example of a first retainer 1100 and a second retainer 1110 are shown and described. The first retainer 1100 and second retainer 1110 are shown attached to the adjunct 300 and cartridge 100 with the cartridge 100 inserted into the first jaw frame 204 (the anvil 210 is also shown). The first retainer 1100 can include a first retainer body 1102 that is attached to the second retainer 1110 via a hinge 1104. The second retainer 1110 can be configured to pivot around the hinge 1104 to transfer a force applied to the second retainer 1110 to the first retainer 1100.

The second retainer 1110 can include a second retainer sloped end 1120, a second retainer lever 1122, and a second retainer lever tab 1124. As before, the second retainer lever tab 1124 can be configured to extend at least partially around the cartridge 100 to attach the first retainer 1100 and the second retainer 1110 to the cartridge 100. Similarly, the second retainer lever 1122 can be pulled or pushed by a user to bend the second retainer sloped end 1120 and move the second retainer lever tab 1124 away from the cartridge 100 to permit removal of the first retainer 1100 and the second retainer 1110 from the cartridge 100.

Figure 11A:
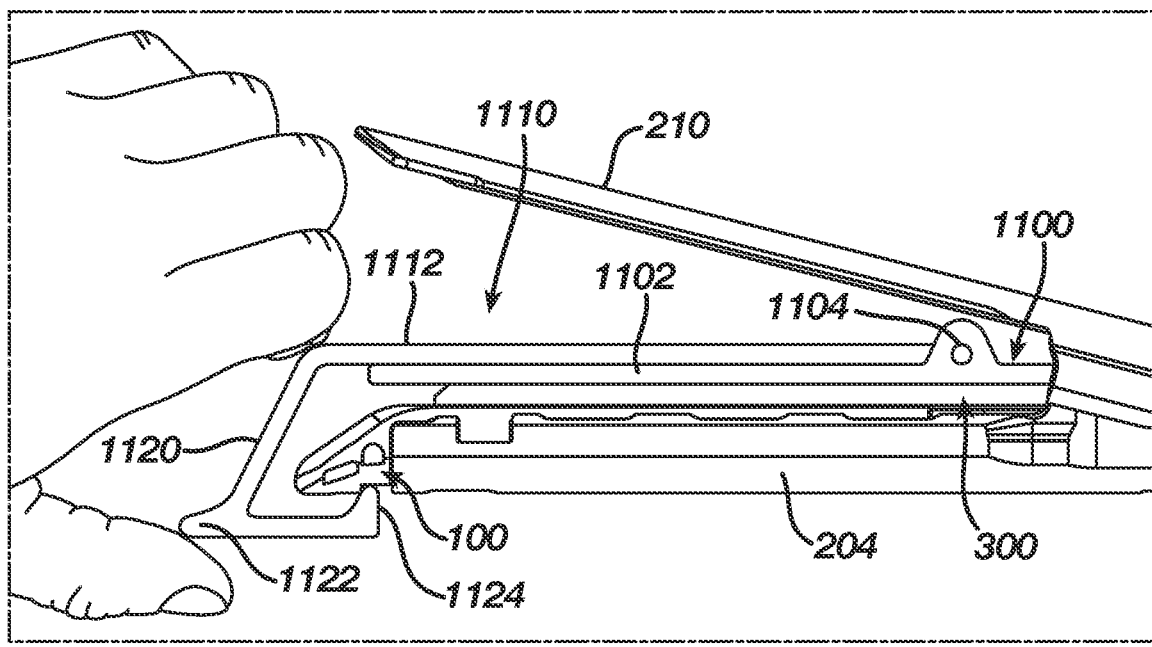
FIG. 11A is a schematic view of another example retainer and a cam with a staple cartridge, according to aspects of the present disclosure.
Figure 11B:
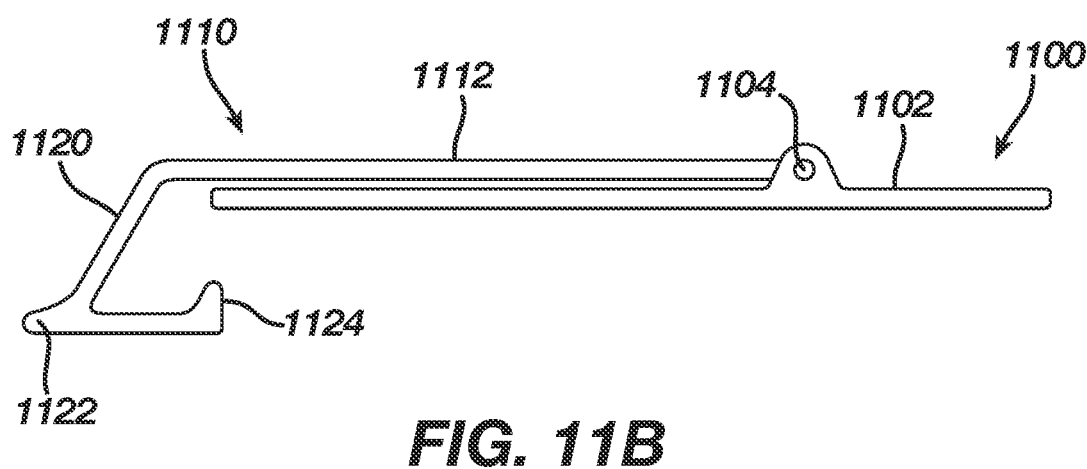
FIG. 11B is a side view of the retainer and a cam of FIG. 11A in a first position with the staple cartridge removed, according to aspects of the present disclosure.
Figure 11C:
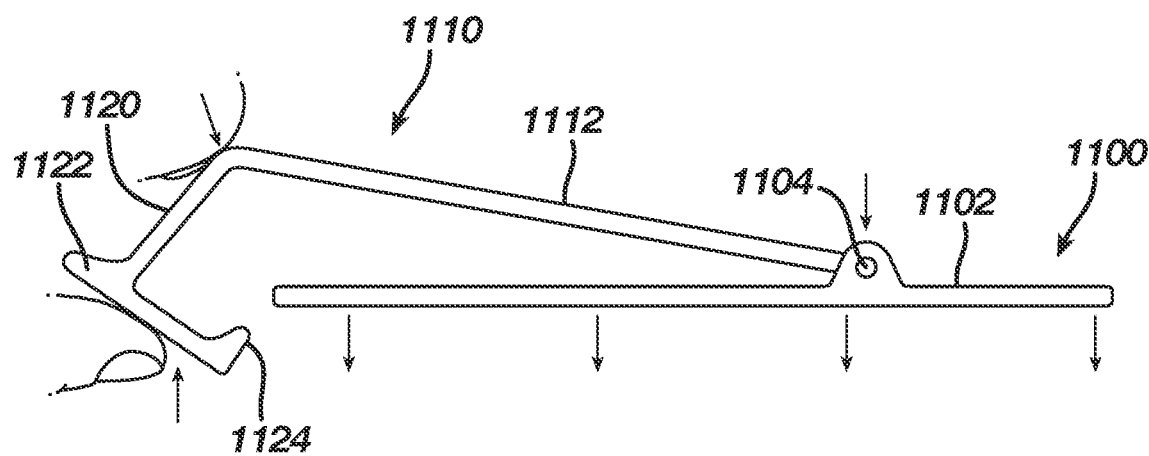
FIG. 11C is a side view of the retainer and the cam of FIGS. 11A and 11B in a second position with the staple cartridge removed, according to aspects of the present disclosure.

As shown in FIGS. 11B and 11C, a user can push up on the second retainer lever 1122 can cause the second retainer 1110 to pivot about the hinge 1104. Since the second retainer lever tab 1124 will also push up on the cartridge 100 when the second retainer lever 1122 is actuated, the force applied to the second retainer lever 1122 will be transferred to the first retainer 1100 and, consequently, the implantable adjunct 300 to compress the implantable adjunct 300. In this way, the implantable adjunct 300 can be secured to the deck 108.

Figure 11D:
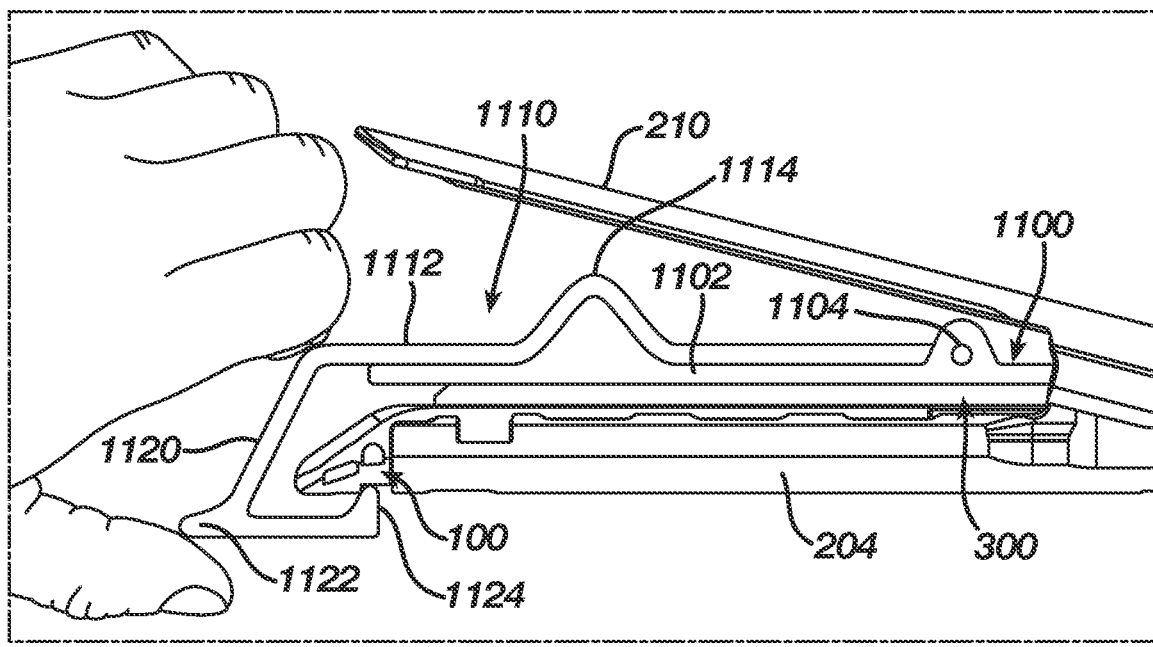
FIG. 11D is a schematic view of a variation of the retainer and cam with a staple cartridge shown in FIGS. 11A, according to aspects of the present disclosure.

FIG. 11D illustrates an alternate example of the second retainer 1110 shown in FIGS. 11A-11C. As shown the second retainer 1110 can further include a second retainer bend 1114 formed into the body of the second retainer 1110. The second retainer bend 1114 can help to better transfer the force applied to the second retainer lever 1122 to the first retainer 1100. Furthermore, the second retainer bend 1114 can be clamped by the anvil 210 to compress the adjunct 300 prior to removal of the first retainer 1100 and the second retainer 1110 from the cartridge 100.

Figure 12A:
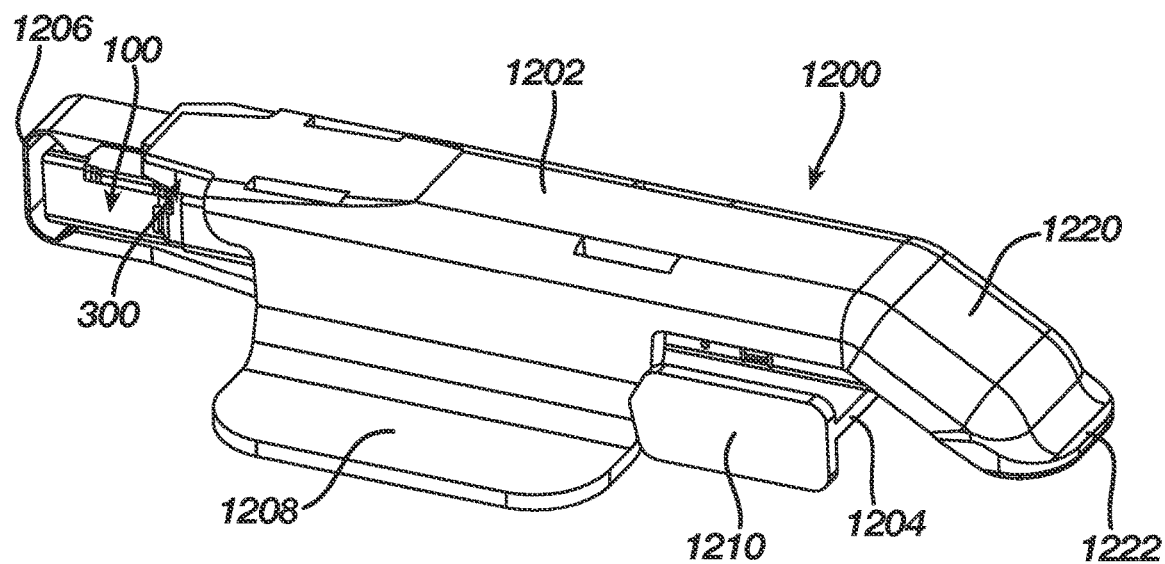
FIG. 12A is a top perspective view of a retainer with a living hinge in a first configuration, according to aspects of the present disclosure.
Figure 12B:
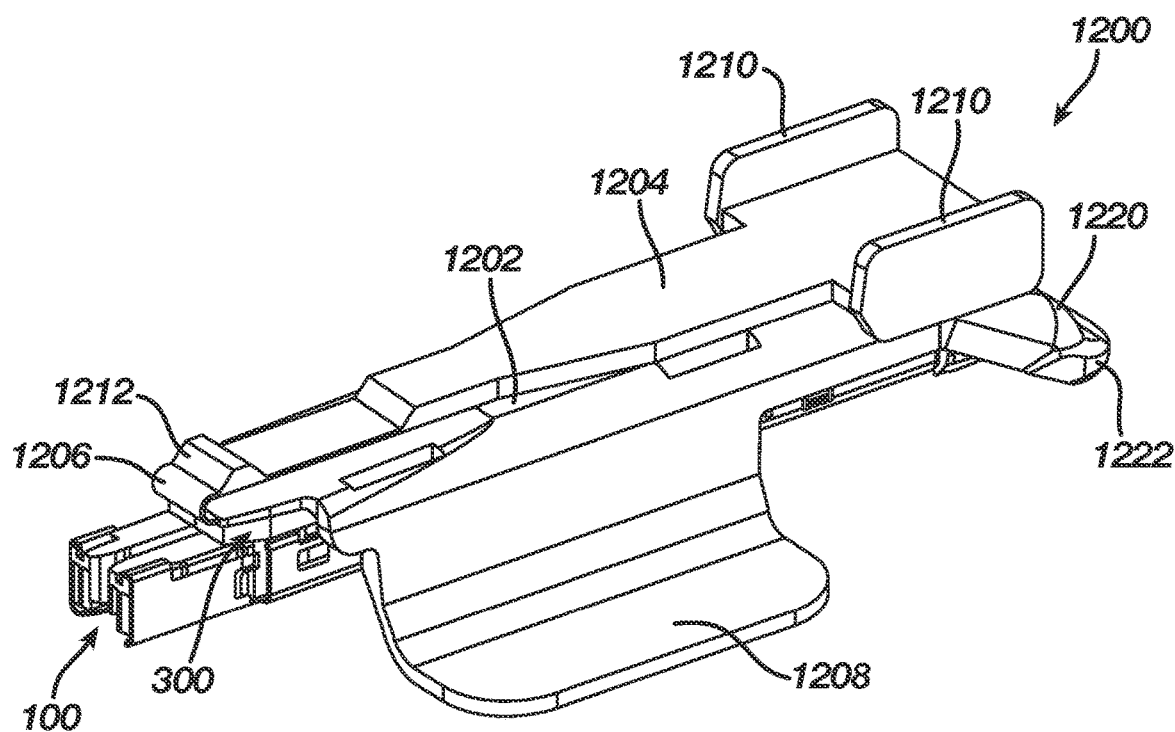
FIG. 12B is a top perspective view of the retainer with a living hinge shown in FIG. 12A in a second configuration, according to aspects of the present disclosure.
Figure 12C:
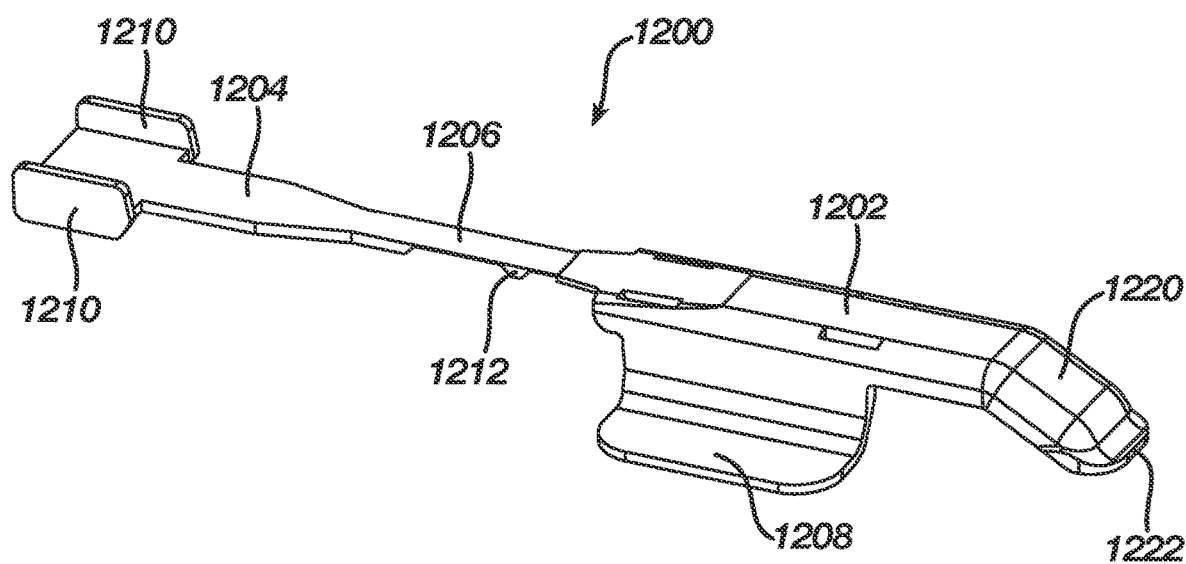
FIG. 12C is another perspective view of the retainer with the living hinge, according to aspects of the present disclosure.
Figure 13A:
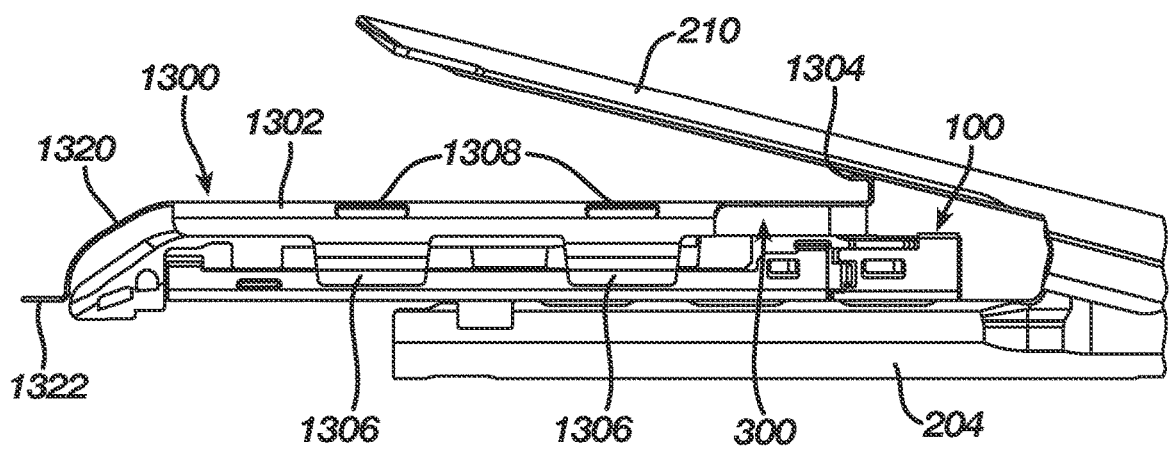
FIG. 13A is a schematic view of another retainer with a staple cartridge and an end effector, according to aspects of the present disclosure.
Figure 13B:
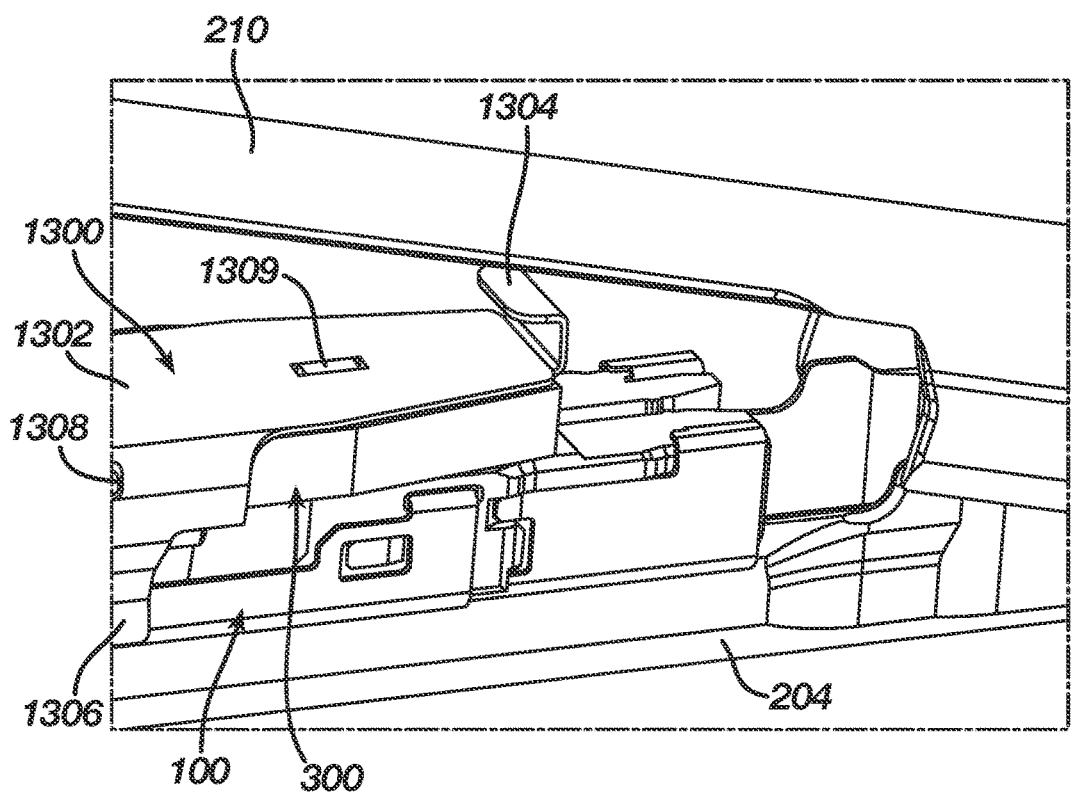
FIG. 13B is a detail view of the retainer with the staple cartridge and the end effector shown in FIG. 13A, according to aspects of the present disclosure.
Figure 13C:
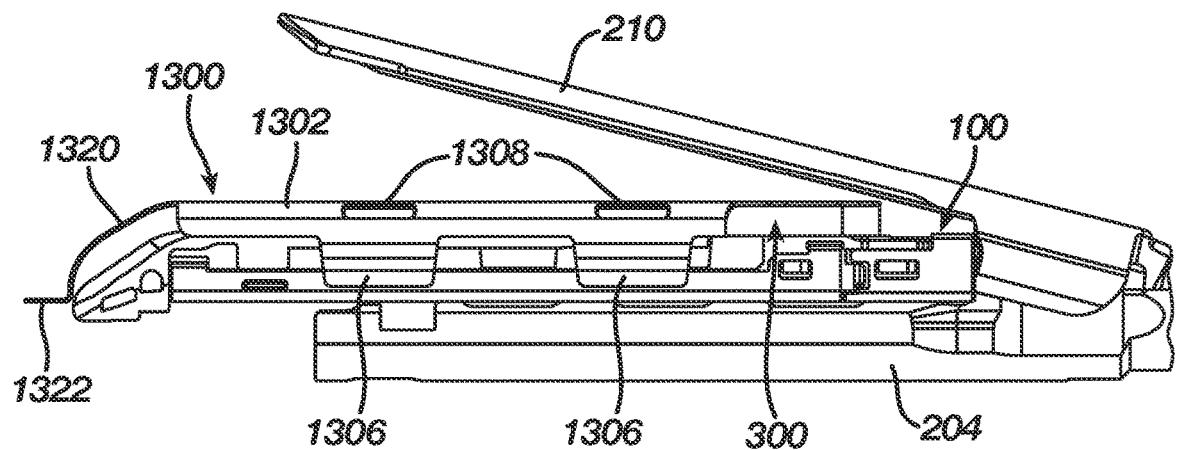
FIG. 13C is a side view of an alternative version of the retainer shown in FIGS. 13A and 13B, according to aspects of the present disclosure.
Figure 13D:
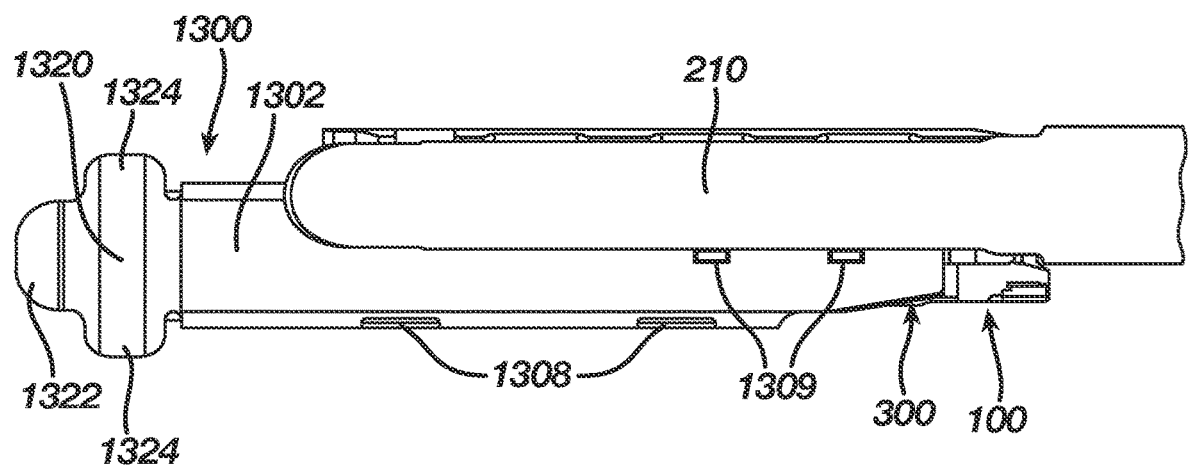
FIG. 13D is a top view of the retainer shown in FIG. 13C, according to aspects of the present disclosure.

As shown in FIGS. 12A-12C, the disclosed technology can further include a retainer 1200 that has a first retainer portion 1202 and a second retainer portion 1204 attached to each other via a living hinge 1206. During packaging, shipping, and prior to use, the first retainer portion 1202 can be positioned on a first side of the cartridge 100 and adjunct 300 and the second retainer portion 1204 can be bent (via the living hinge 12016) around the cartridge 100 to an opposite side of the cartridge 100 as shown in FIG. 12A. The retainer 1200 can further include a retainer flange 1208 that can engage with a retainer latch 1210 to secure the retainer 1200 around the cartridge 100. Because the retainer 1200 can be bent around the cartridge 100 to protect the cartridge 100, the cartridge 100 can be shipped in a foil-lined packaging rather than requiring a hard container.

The user can detach the retainer latch 1210 from the retainer flange 1208 and bend the second retainer portion 1204 around the cartridge 100 to remove the retainer 100 from the cartridge 100. Before entirely removing the retainer 1200 from the cartridge 100, the retainer 1200 can remain attached to the cartridge 100 via the retainer flange 1208 and the cartridge 100 and retainer 1200 can be inserted into the channel 206 together. The retainer 1200 can further include a protrusion 1212 that can be configured to engage with the anvil 1210 to help ensure the proximal end of the cartridge 100 is pushed down into the channel 208. The user can further push the cartridge 100 downward into the channel 208 by pushing on the retainer latch 1210 which can protrusion outwardly and provide a surface that the user can push against. As the user pushes against the retainer 1200, the retainer 1200 will compress the adjunct 300 to ensure the adjunct 300 is properly secured.

As shown in FIGS. 13A-13D, the disclosed technology can include a retainer 1300 that can be configured to protect the implantable adjunct 300 and the cartridge 100 and be used to ensure the implantable adjunct 300 is sufficiently compressed against the cartridge 100 prior to use. As shown, the retainer 1300 can include a retainer body 1302, a proximal protrusion 1304, one or more retainer tabs 1306, one or more aperture 1308, and a retainer alignment protrusion 1309. The proximal protrusion 1304 can be configured to extend upwardly to engage with the anvil 210 such that the proximal portion of the retainer 1300 can be caused to compress the proximal end of the adjunct 300. The retainer tabs 1306 can be configured to extend at least partially around the cartridge 100 and attach the retainer 1300 to the cartridge 100. Although most of the retainer alignment protrusion 1309 is not shown, the retainer alignment protrusion 1309 can be configured to extend downward from the retainer 1300 and at least partially into the adjunct 300 and the cartridge 100 similar to the retainer alignment protrusion 505 previously described.

The retainer 1300 can further include a retainer sloped end 1320 and a retainer lever 1322 that can be pushed or pulled by a user to remove the retainer 1300 from the adjunct 300 and the cartridge 100. The retainer sloped end 1320 can further include one or more wings 1324 extending outwardly that can also be gripped and pulled or pushed by a user to remove the retainer 1300 from the cartridge 100.

In some examples, the user can simply push the retainer 1300 against the adjunct 300 to compress the adjunct 300, while in other examples the user can clamp down on the retainer 1300 with the anvil 210 to compress the adjunct 300.

Figure 14A:
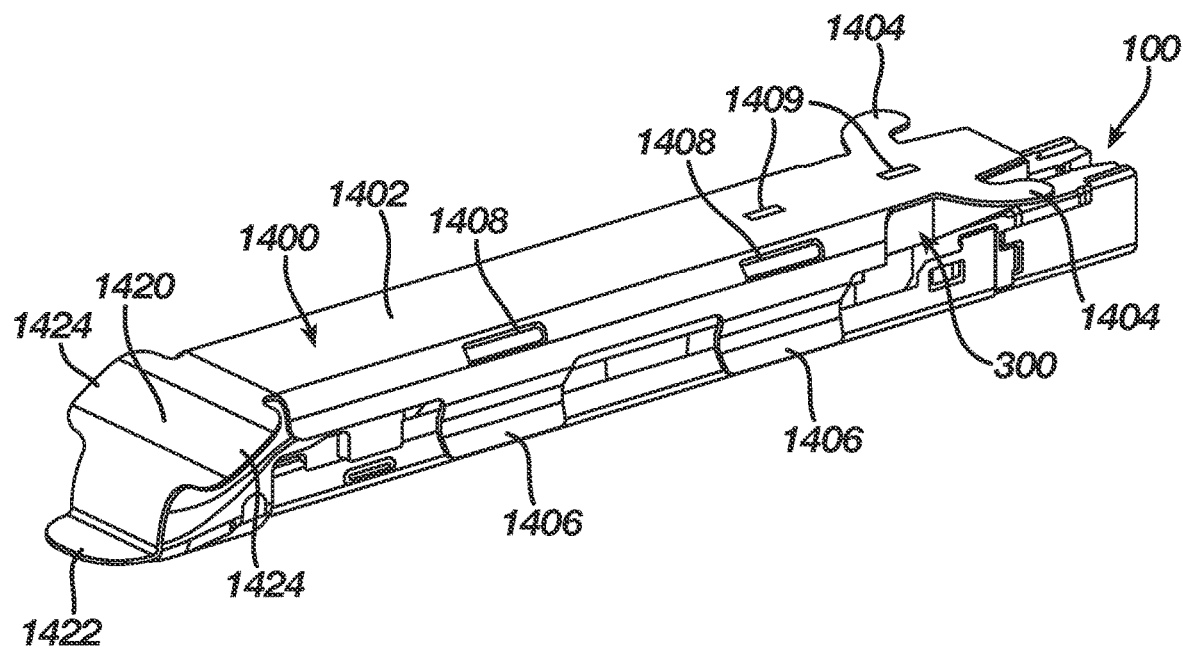
FIG. 14A is a perspective view of another example retainer and staple cartridge, according to aspects of the present disclosure.
Figure 14B:
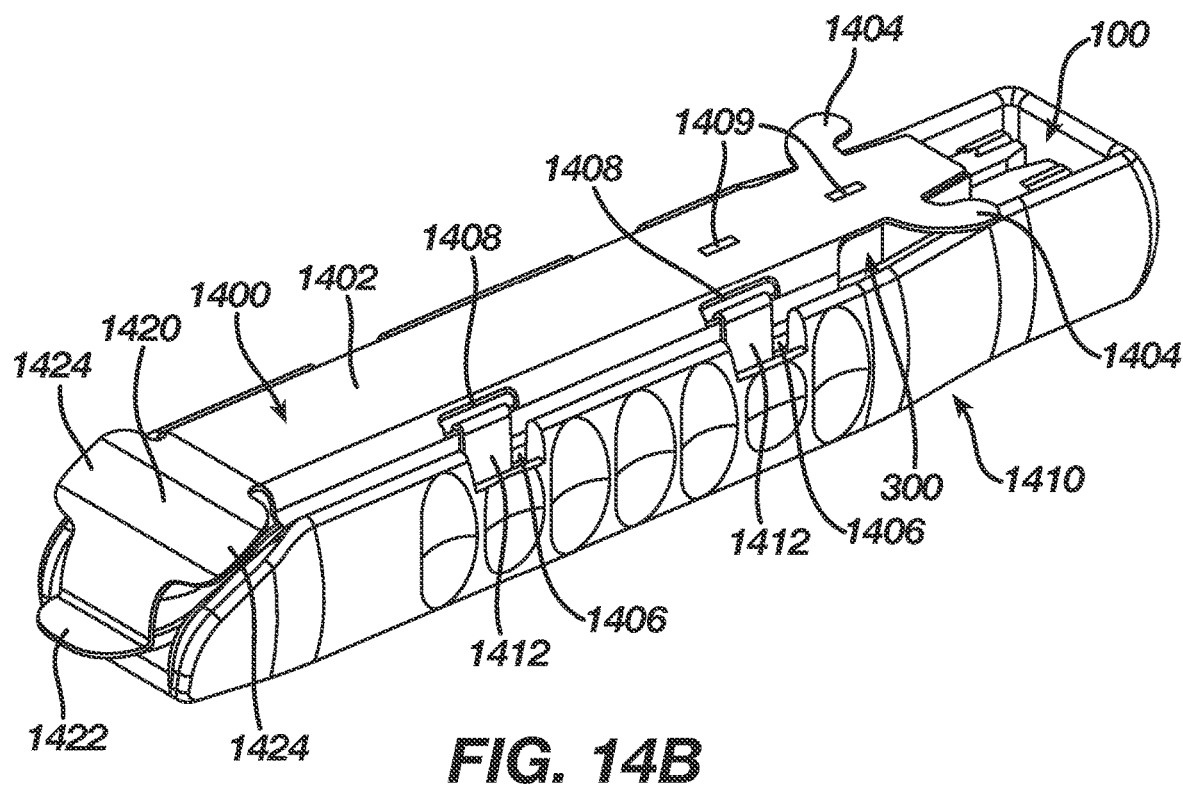
FIG. 14B is a perspective view of the retainer and staple cartridge shown in FIG. 14A with a pan cover, according to aspects of the present disclosure.
Figure 14C:
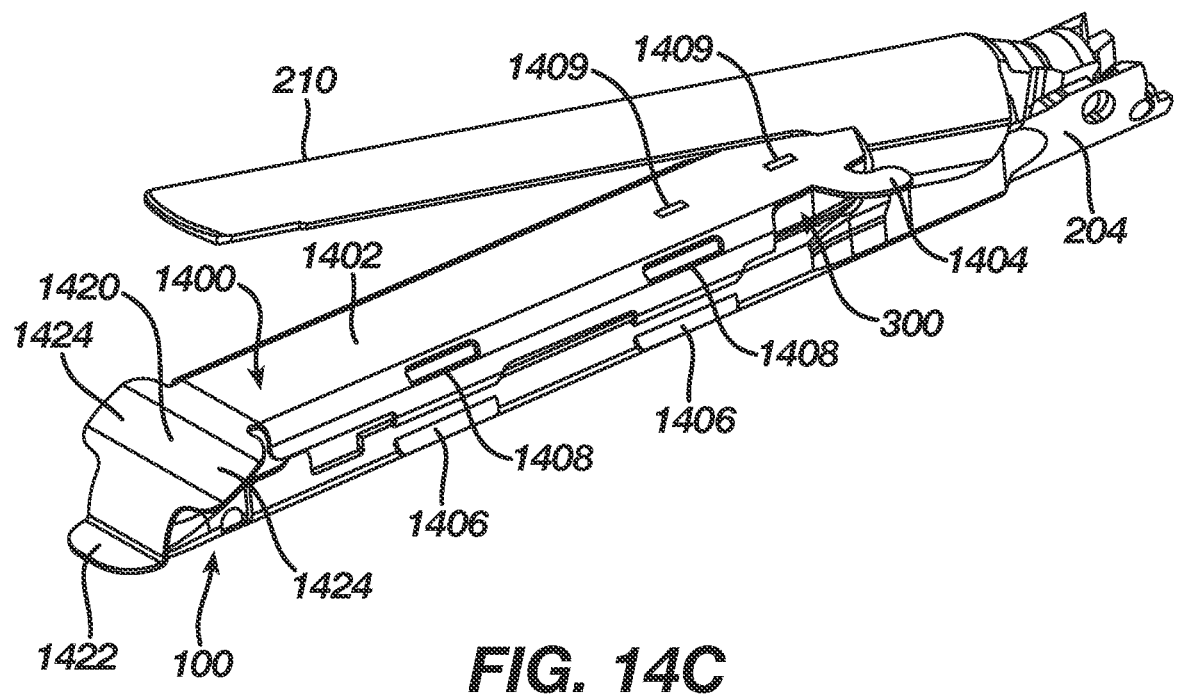
FIG. 14C is a perspective view of the retainer shown in FIGS. 14A and 14B and an end effector, according to aspects of the present disclosure.
Figure 14D:
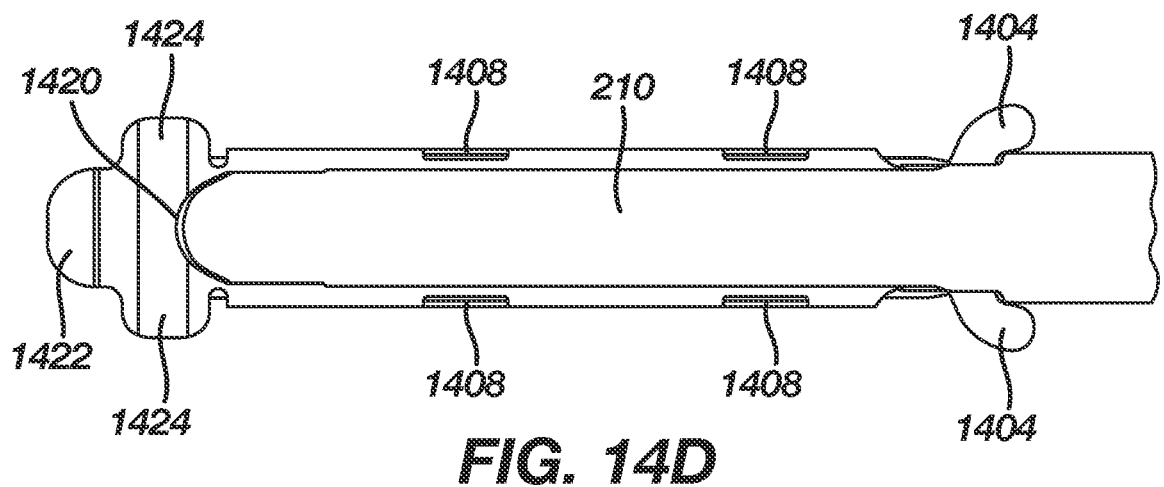
FIG. 14D is a top view of the retainer and end effector shown in FIG. 14C, according to aspects of the present disclosure.
Figure 14E:
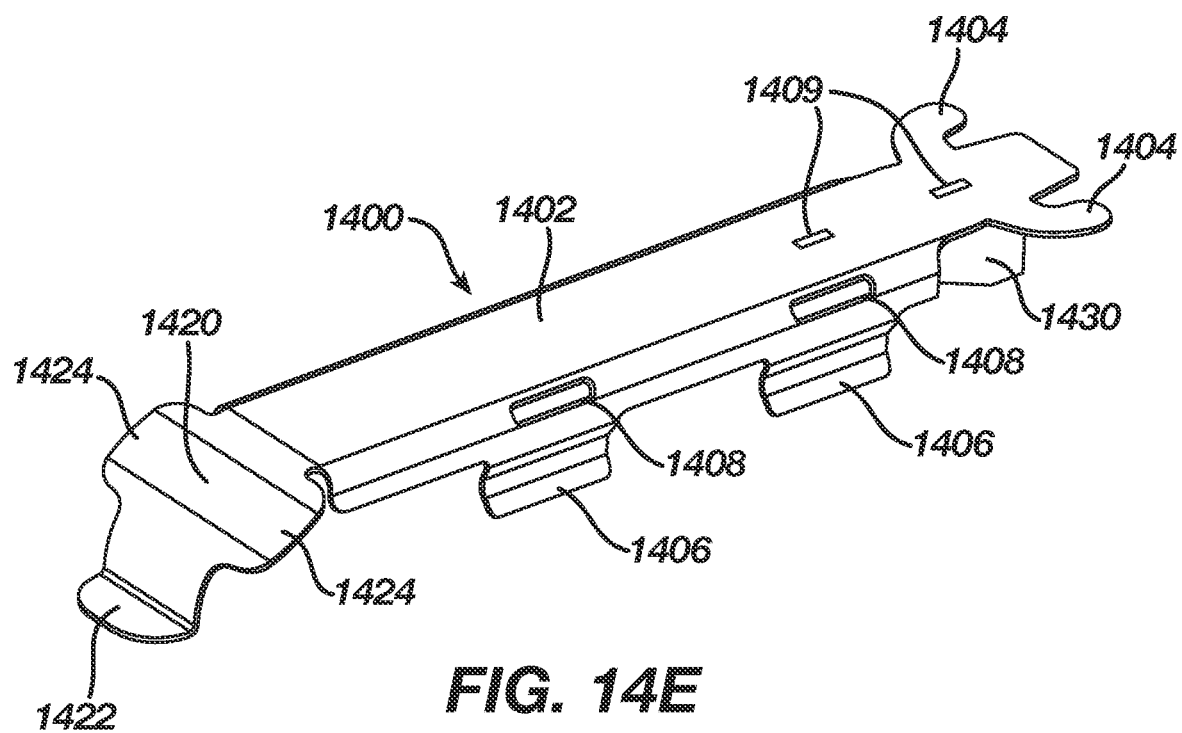
FIG. 14E is a perspective view of the retainer shown in FIGS. 14A-14D, according to aspects of the present disclosure.
Figure 14F:
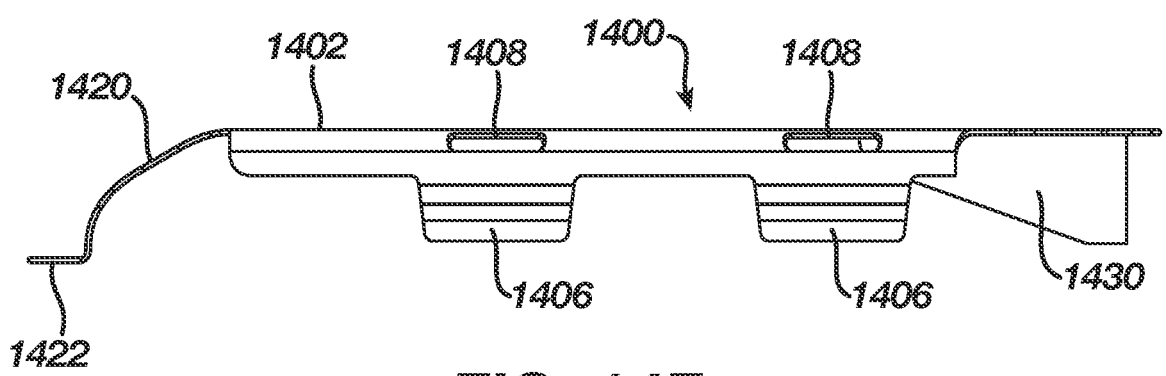
FIG. 14F is a side view of the retainer shown in FIGS. 14A-14E, according to aspects of the present disclosure.
Figure 14G:
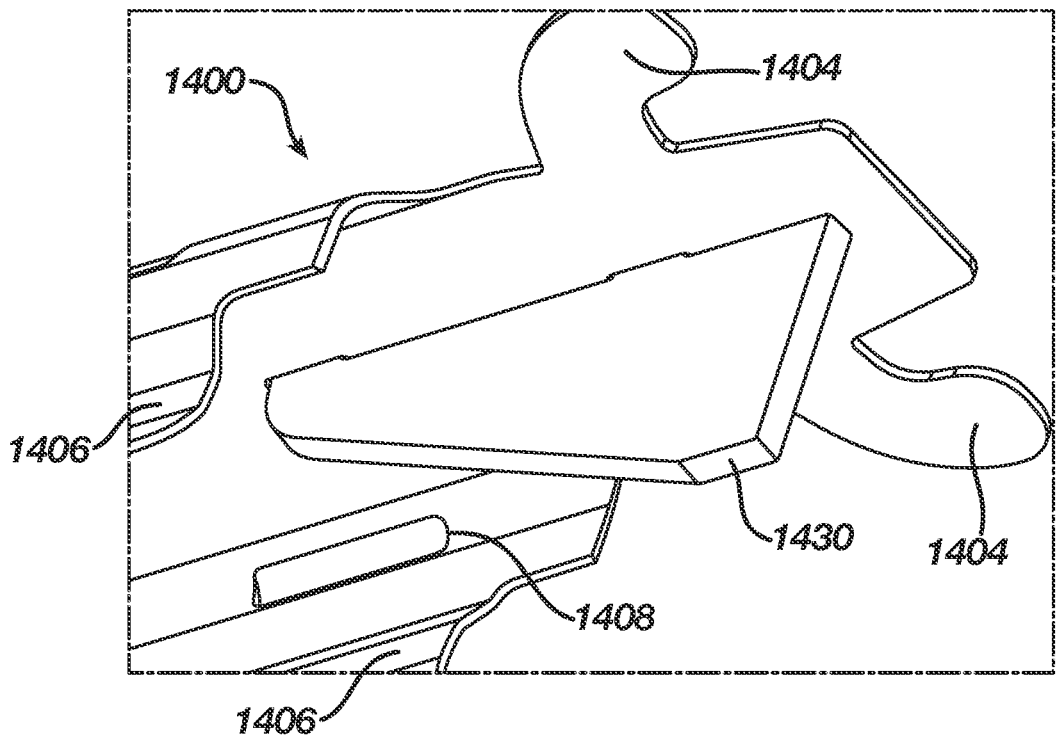
FIG. 14G is a detail view of the retainer shown in FIGS. 14A-14F, according to aspects of the present disclosure.
Figure 14H:
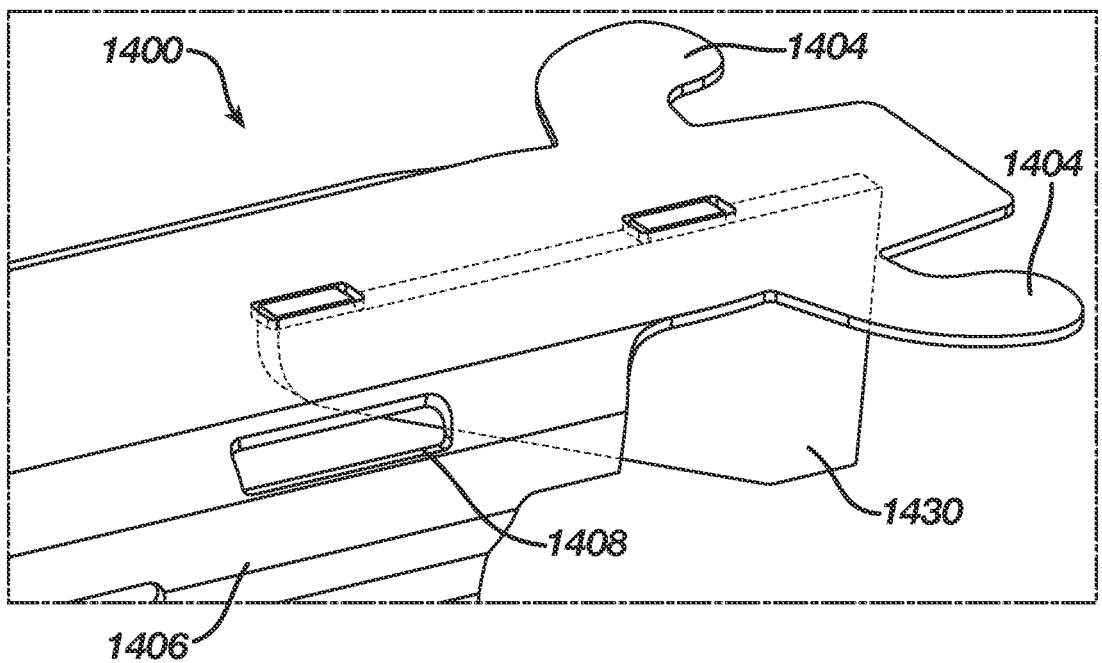
FIG. 14H is another detail view of the retainer shown in FIGS. 14A-14G, according to aspects of the present disclosure.

FIGS. 14A-14H illustrate another example of a retainer 1400 and a pan protector 1410 according to the disclosed technology. The retainer 1400 can be similar to the retainer 1300 just described in that the retainer 1400 can include a retainer body 1402, one or more retainer tabs 1406, one or more aperture 1408, a retainer alignment protrusion 1409 (shown in FIGS. 14E-14H), a retainer sloped end 1420, a retainer lever 1422, and one or more wings 1424 extending outwardly from the retainer sloped end. The retainer 1400 can further include proximal wings 1404 rather than the proximal protrusion 1304. The proximal wings 1404 can serve a similar purpose in that the proximal wings 1404 can be configured to engage with the anvil 210 to cause the proximal end of the retainer 1400 to compress the adjunct 300 (as shown in FIGS. 14C and 14D). Furthermore, the proximal wings 1404 can help to prevent misalignment of the cartridge 100 in the channel 208 and prevent sled bumping. Although the proximal wings 1404 are shown as extending out from the retainer 1400 horizontally, it will be appreciated that the proximal wings 1404 can comprise other configurations to help prevent misalignment of the cartridge 100 in the channel 208. For example, the proximal wings 1404 can comprise different shapes and extend out from the retainer 1400 at different angles relative to the top of the retainer 1400 (e.g., +/−30 degrees, +/−45 degrees, +/−60 degrees, +/−90 degrees, etc.).

As shown, the pan protector 1420 can further include hooks 1412 that can be configured to engage with the apertures 1408 of the retainer 1400. The hooks 1412 can be similar to the hooks 614, 714, and 814 previously shown and described. Although not shown, it will also be appreciated that the pan cover 1410 can include a spring to cause the hooks 1412 to bias outwardly. Similar to the examples previously described, the hooks 1412 can bias outwardly when the user pushes down on the retainer 1400 and causes the hooks 1412 to come out of the apertures 1408 formed in the retainer 1400. In this way, the user can ensure the adjunct 300 has been sufficiently compressed and can then remove the pan cover 1410 from the cartridge 100.

Figure 15:
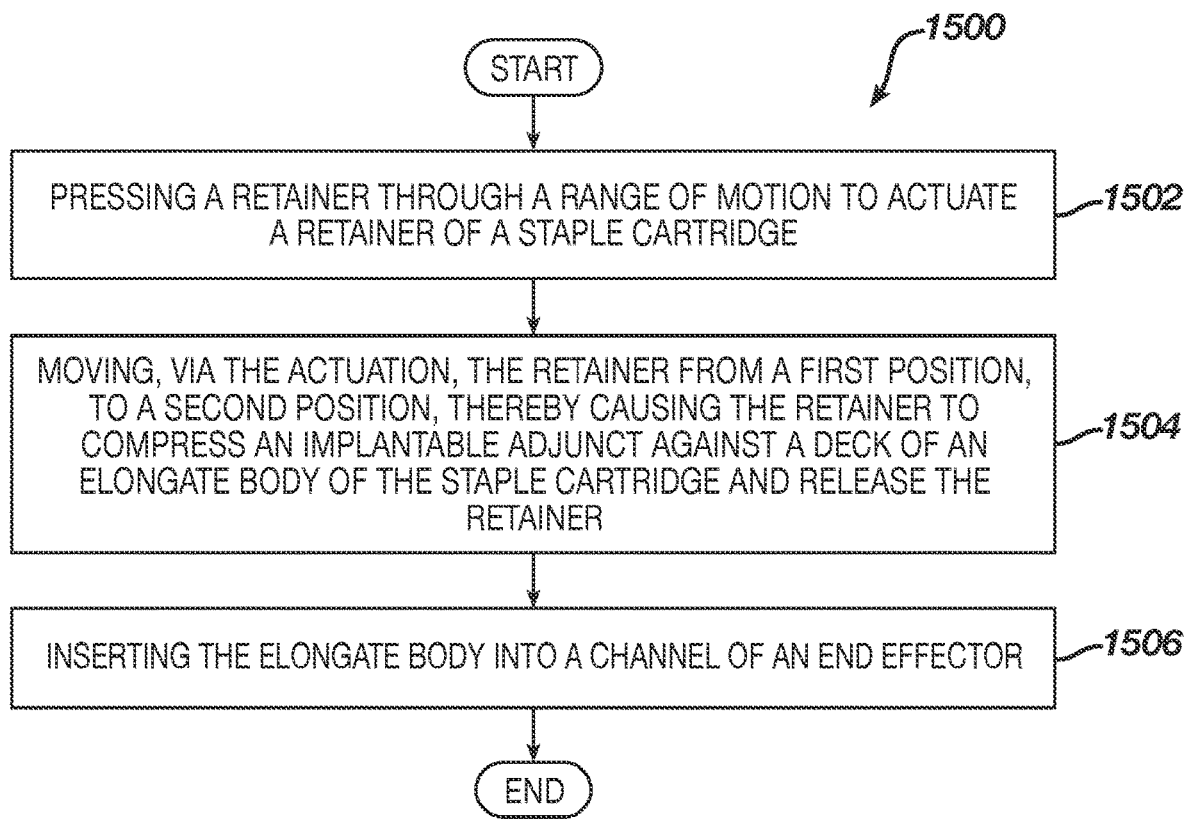
FIG. 15 is a flow chart illustrating a method of causing a retainer to compress an implantable adjunct against a deck of a staple cartridge, according to aspects of the present disclosure.

FIG. 15 is a flowchart for an example method 1500 of loading a staple cartridge 100 onto an end effector 202, according to aspects of the present disclosure. Method 1500 can be performed to ensure the implantable adjunct 300 is sufficiently compressed against the cartridge 100 according to the many examples shown and described herein. The method 1500 includes pressing 1502 a retainer through a range of motion to actuate a retainer of a staple cartridge. The method 1500 includes moving, 1504, via the actuation, the retainer from a first position, to a second position, thereby causing the retainer to compress an implantable adjunct against a deck of an elongate body of the staple cartridge and release the retainer from the staple cartridge. The method 1500 further includes inserting 1506 the elongate body into a channel of an end effector.

The method just described can be used with any of the examples shown and described in relation to FIGS. 4A-14H. That is, the method 1500 should be understood in the context of the many examples described herein. Furthermore, the method just described is not limited to the specific steps described herein but can include other elements described in relation to any of the examples given herein. Accordingly, the method 1500 should not be construed as limited to just the features explicitly described in the preceding paragraph.

Examples of the present disclosure can be implemented by any of the following numbered clauses:

Clause 1: A staple cartridge (100), comprising: an elongate body (101), the elongate body (101) comprising a deck (108), the elongate body (101) defining a plurality of staple pockets (110), each of the staple pockets (110) accessible via an opening (112) defined by the deck (108); an implantable adjunct (300) removably secured to the deck (108); and a retainer (400-1400) removably securable to the elongate body (101), the retainer (400-1400) moveable through a range of motion from a first position to a second position relative to the elongate body (101) while the retainer (400-1400) is secured to the elongate body (101), with the retainer (400-1400) secured to the elongate body (101), the implantable adjunct (300) positioned intermediate the retainer (400-1400) and the elongate body (101), a movement of the retainer (400-1400) through at least a portion of the range of motion compressing the implantable adjunct (300) against the deck (108) of the elongate body (101); and a latch (412, 512, 614, 714, 814, 914, 1014, 1124, 1210, 1306, 1412) configured to secure the retainer to the elongate body when the retainer (400-1400) is in the first position and to automatically release the retainer from securement via the latch to the elongate body when the retainer (400-1400) is in the second position.

Clause 2: The staple cartridge (100) of claim 1, further comprising a pan protector (410, 510, 610, 710, 810), the elongate body (101) and the implantable adjunct (300) being positioned intermediate the retainer (400-800) and the pan protector (410, 510, 610, 710, 810), the latch (412, 512, 614, 714, 814) configured to secure the pan protector (410, 510, 610, 710, 810) to the retainer (400-800) when the retainer (400-800) is in the first position and to release the pan protector (410, 510, 610, 710, 810) from the retainer (400-800) when the retainer (400-800) is in the second position.

Clause 3: The staple cartridge (100) of claim 2, wherein the retainer (400, 500) comprises a track (408, 508) and the pan protector (410, 510) comprises a protrusion (412, 512) configured to slide along the track (408, 508), the track and the protrusion defining the latch.

Clause 4: The staple cartridge (100) of claim 3, wherein the retainer (400, 500) further comprises a recess (409, 509), the recess (409, 509) configured to retain the protrusion (412, 512) when the retainer (400, 500) is in the first position and to release the pan protector (410, 510) from the retainer (400, 500) when the retainer (400, 500) is in the second position.

Clause 5: The staple cartridge (100) of claim 4, wherein the protrusion (412, 512) is configured to slide out of the recess (409, 509) and into and along the track (408, 508) when the retainer (400, 500) is actuated from the first position to the second position.

Clause 6: The staple cartridge (100) of any one of claims 3-5, the pan protector (410, 510) further comprising a retainer stop (514, 515) configured to contact the retainer (400, 500) and prevent the retainer (400, 500) from moving to a position beyond the second position when moving in the direction from the first position to the second position.

Clause 7: The staple cartridge (100) of claim 2, the pan protector (610, 710, 810) further comprising a hook (614, 714, 814) and the retainer (600-800) further comprising an aperture (606, 706, 806) configured to receive at least a portion of the hook (614, 714, 814), the hook and the aperture defining the latch.

Clause 8: The staple cartridge (100) of claim 7, the pan protector (610, 710, 810) further comprising a spring (620, 720, 820) configured to cause the hook (614, 714, 814) to move outwardly when the retainer (600-800) is in the second position.

Clause 9: The staple cartridge (100) of claim 7 or claim 8, the pan protector (610, 710, 810) further comprising a retainer stop (718) configured to contact the retainer (610, 710, 810) and prevent the retainer (600-800) from moving to a position beyond the second position when moving in the direction from the first position to the second position.

Clause 10: The staple cartridge (100) of claim 1, the retainer comprising a first retainer body (900, 1000) and a second retainer body (910, 1010), the second retainer body configured to move through a range of motion relative to the first retainer body.

Clause 11: The staple cartridge (100) of claim 10, the second retainer body (910, 1010) comprising a first protrusion (914, 1014) and a second protrusion (916, 1016), and the first retainer body (900, 1000) comprising a third protrusion (906, 1006), the third protrusion configured to slide along the first protrusion and the second protrusion in a first direction and to be prevented from sliding in a second direction opposite the first direction.

Clause 12: The staple cartridge (100) of claim 11, wherein, when the third protrusion is slid in the first direction over the first protrusion and the second protrusion, the first retainer body (900, 1000) is caused to compress the implantable adjunct (300) against the deck (108) of the elongate body (101) along approximately an entire length of the implantable adjunct (300).

Clause 13: The staple cartridge (100) of any one of claims 10-12, the second retainer body comprising a retention member (908, 1008) configured to attach the first retainer body (900, 1000) and the second retainer body (910, 1010) to the elongate body (101).

Clause 14: The staple cartridge (100) of any of the preceding claims, the retainer (400-1400) further comprising a lever (404, 504, 604, 704, 804, 904, 1022, 1122, 1222, 1322) disposed at a distal end of the retainer (400-1400), the lever configured to distribute a force to the retainer to detach the retainer from the elongate body (101) when the force is applied to the lever.

Clause 15: The staple cartridge (100) of claim 14, wherein the lever further comprises a lever tab (1024, 1124) configured to prevent the retainer (400-1400) from detaching from the elongate body (101).

Clause 16: The staple cartridge (100) of claim 14, wherein the lever (1122) is attached to a retainer body (1102) by a hinge (1104), the hinge (1104) configured to permit the lever (1122) to rotate relative the retainer body (1102).

Clause 17: A method of causing a retainer (400, 500, 600, 700) to compress an implantable adjunct (300) against a deck (108) of an elongated body (120), the method comprising: actuating a retainer (400-1400) through a range of motion from a first position to a second position relative the elongate body (101) while the retainer (400-1400) is secured to the elongate body (101); compressing the implantable adjunct (300) against the deck (108) when actuating the retainer from the first position to the second position; releasing the retainer (400-1400) from the elongate body (101); and inserting the elongate body (101) into a channel (206) of an end effector (202).

Clause 18: The method of claim 17, wherein compressing the implantable adjunct (300) against the deck comprises compressing the implantable adjunct (300) along approximately the entire length of the implantable adjunct (300).

Clause 19: The method of claim 17 or claim 18 further comprising a pan protector (410, 510, 610, 710, 810), the elongate body (101) and the implantable adjunct (300) being positioned intermediate the retainer (400-800) and the pan protector (410, 510, 610, 710, 810), wherein actuating the retainer (400-800) from the first position to the second position further causes the pan protector (410, 510, 610, 710, 810) to be released from the retainer (400-800).

Clause 20: The method of claim 19, wherein the retainer (400, 500) comprises a track (408, 508) and the pan protector (410, 510) comprises a protrusion (412, 512) configured to slide along the track (408, 508).

Clause 21: The method of claim 19, wherein the pan protector (610, 710, 810) further comprises a hook (614, 714, 814) and the retainer (600-800) further comprises an aperture (606, 706, 806) configured to receive at least a portion of the hook (614, 714, 814), the hook configured to detach from the aperture when the retainer is actuated from the first position to the second position.

In describing example embodiments, terminology has been resorted to for the sake of clarity. As a result, not all possible combinations have been listed, and such variants are often apparent to those of skill in the art and are intended to be within the scope of the claims which follow. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Similarly, some steps of a method can be performed in a different order than those described herein without departing from the scope of the disclosed technology.

What is claimed is:

1. A staple cartridge, comprising:
    an elongate body, the elongate body comprising a deck, the elongate body defining a plurality of staple pockets, each of the staple pockets accessible via an opening defined by the deck;
    an implantable adjunct removably secured to the deck; and
    a retainer removably securable to the elongate body, the retainer moveable through a range of motion from a first position to a second position relative to the elongate body while the retainer is secured to the elongate body,
        with the retainer secured to the elongate body, the implantable adjunct positioned intermediate the retainer and the elongate body,
        a movement of the retainer through at least a portion of the range of motion compressing the implantable adjunct against the deck of the elongate body; and
    a latch configured to secure the retainer to the elongate body when the retainer is in the first position and to automatically release the retainer from securement via the latch to the elongate body when the retainer is in the second position.

2. The staple cartridge of claim 1, further comprising a pan protector, the elongate body and the implantable adjunct being positioned intermediate the retainer and the pan protector, the latch configured to secure the pan protector to the retainer when the retainer is in the first position and to release the pan protector from the retainer when the retainer is in the second position.

3. The staple cartridge of claim 2, wherein the retainer comprises a track and the pan protector comprises a protrusion configured to slide along the track, the track and the protrusion defining the latch.

4. The staple cartridge of claim 3, wherein the retainer further comprises a recess, the recess configured to retain the protrusion when the retainer is in the first position and to release the pan protector from the retainer when the retainer is in the second position.

5. The staple cartridge of claim 4, wherein the protrusion is configured to slide out of the recess and into and along the track when the retainer is actuated from the first position to the second position.

6. The staple cartridge of claim 3, the pan protector further comprising a retainer stop configured to contact the retainer and prevent the retainer from moving to a position beyond the second position when moving in the direction from the first position to the second position.

7. The staple cartridge of claim 2, the pan protector further comprising a hook and the retainer further comprising an aperture configured to receive at least a portion of the hook, the hook and the aperture defining the latch.

8. The staple cartridge of claim 7, the pan protector further comprising a spring configured to cause the hook to move outwardly when the retainer is in the second position.

9. The staple cartridge of claim 7, the pan protector further comprising a retainer stop configured to contact the retainer and prevent the retainer from moving to a position beyond the second position when moving in the direction from the first position to the second position.

10. The staple cartridge of claim 1, the retainer comprising a first retainer body and a second retainer body, the second retainer body configured to move through a range of motion relative to the first retainer body.

11. The staple cartridge of claim 10, the second retainer body comprising a first protrusion and a second protrusion, and the first retainer body comprising a third protrusion, the third protrusion configured to slide along the first protrusion and the second protrusion in a first direction and to be prevented from sliding in a second direction opposite the first direction.

12. The staple cartridge of claim 11, wherein, when the third protrusion is slid in the first direction over the first protrusion and the second protrusion, the first retainer body is caused to compress the implantable adjunct against the deck of the elongate body along approximately an entire length of the implantable adjunct.

13. The staple cartridge of claim 10, the second retainer body comprising a retention member configured to attach the first retainer body and the second retainer body to the elongate body.

14. The staple cartridge of claim 1, the retainer further comprising a lever disposed at a distal end of the retainer, the lever configured to distribute a force to the retainer to detach the retainer from the elongate body when the force is applied to the lever.

15. The staple cartridge of claim 14, wherein the lever further comprises a lever tab configured to prevent the retainer from detaching from the elongate body.

16. The staple cartridge of claim 14, wherein the lever is attached to a retainer body by a hinge, the lever configured to permit the lever to rotate relative the retainer body.

17. A method of causing a retainer to compress an implantable adjunct against a deck of an elongated body, the method comprising:
   actuating a retainer through a range of motion from a first position to a second position relative the elongate body while the retainer is secured to the elongate body;
   compressing the implantable adjunct against the deck when actuating the retainer from the first position to the second position;
   releasing the retainer from the elongate body; and
   inserting the elongate body into a channel of an end effector.

18. The method of claim 17, wherein compressing the implantable adjunct against the deck comprises compressing the implantable adjunct along approximately the entire length of the implantable adjunct.

19. The method of claim 17 further comprising a pan protector, the elongate body and the implantable adjunct being positioned intermediate the retainer and the pan protector,
   wherein actuating the retainer from the first position to the second position further causes the pan protector to be released from the retainer.

20. The method of claim 19, wherein the retainer comprises a track and the pan protector comprises a protrusion configured to slide along the track.

* * * * *